(12) United States Patent
Godowski et al.

(10) Patent No.: US 6,551,822 B1
(45) Date of Patent: *Apr. 22, 2003

(54) NL4 TIE LIGAND HOMOLOGUE

(75) Inventors: Paul J. Godowski, Burlingame, CA (US); Austin L. Gurney, Belmont, CA (US); Kenneth Hillan, San Francisco, CA (US); David Botstein, Belmont, CA (US); Audrey Goddard, San Francisco, CA (US); Margaret Roy, San Francisco, CA (US); Napoleone Ferrara, San Francisco, CA (US); Daniel Tumas, Orinda, CA (US); Ralph Schwall, Pacifica, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/202,088

(22) PCT Filed: Sep. 14, 1998

(86) PCT No.: PCT/US98/19093

§ 371 (c)(1),
(2), (4) Date: Dec. 8, 1998

(87) PCT Pub. No.: WO99/15653

PCT Pub. Date: Apr. 1, 1999

Related U.S. Application Data

(63) Continuation-in-part of application No. 08/960,507, filed on Oct. 29, 1997, now Pat. No. 6,057,435, which is a continuation-in-part of application No. 08/933,821, filed on Sep. 19, 1997, now Pat. No. 5,972,338.

(51) Int. Cl.[7] .................. C07K 14/475; C12N 5/10; C12N 15/12
(52) U.S. Cl. .................. 435/325; 530/300; 530/350; 530/402; 424/192.1; 536/23.1; 536/23.5; 435/69.1; 435/69.7; 435/320.1; 435/252.3; 435/254.11; 514/2
(58) Field of Search .................. 530/300, 350, 530/402; 536/23.1, 23.5, 23.4; 435/69.1, 6, 69.7, 325, 320.1, 252.3, 254.11; 514/2; 424/192.1

(56) References Cited

U.S. PATENT DOCUMENTS

| | | | |
|---|---|---|---|
| 5,447,860 A | 9/1995 | Ziegler | |
| 5,521,073 A | 5/1996 | Davis et al. | |
| 5,643,755 A | 7/1997 | Davis et al. | |
| 5,650,490 A | 7/1997 | Davis et al. | |
| 5,972,338 A | 10/1999 | Godowski et al. | |
| 6,030,831 A | * 2/2000 | Godowski et al. | |
| 6,057,435 A | 5/2000 | Godowski et al. | |

FOREIGN PATENT DOCUMENTS

| WO | WO 93/14124 | 7/1993 |
|---|---|---|
| WO | WO 95/13387 | 5/1995 |
| WO | WO 95/21866 | 8/1995 |
| WO | WO 95/26364 | 10/1995 |
| WO | WO 96/09381 | 3/1996 |
| WO | WO 96/11269 | 4/1996 |
| WO | WO 96/31598 | 10/1996 |
| WO | WO 97/48804 | 12/1997 |

OTHER PUBLICATIONS

GenBank Accession No. Y16132.1, Homo sapiens mRNA for angiopoietin–like factor, Jun. 1 1998.*
EMBL Accession No. CAA76078.1, CDT6, Jun. 1, 1998.*
Peek et al., Molecular cloning of a new angiopoietin–like factro from the human cornea, Invest. Ophthalmol. Vis. Sci., 39(10):1782–1788 (Sep. 1998).*
Stratagene Cloning Systems 1994 Catalog, Stratagene: California, pp. 22 and 43 (1994).*
Davis et al., "Isolation of angiopoietin–1, a ligand for the TIE2 receptor, by secretion–trap expression cloning" *Cell* 85(7):1161–1169 (Dec. 27, 1996).
Dumont et al., "The endothelial–specific receptor tyrosine kinase, tek, is a member of a new subfamily of receptors" *Oncogene*8(5):1293–1301 (May 1993).
Hanahan, D., "Signaling vascular morphogenesis and maintenance" *Science* 277:48–50 (1997).
Kaipainen et al., "Enhanced expression of the tie receptor tyrosine kinase messenger RNA in the vascular endothelium of metastatic melanomas" *Cancer Research* 54(24):6571–6577 (Dec 15, 1994).
Korkonen et al. "Enhanced expression of the tie receptor tyrosine kinase in endothelial cells during neovascularization" *Blood* 80(10):2548–2555 (Nov. 15, 1992).
Maisonpierre et al., "Distinct rat genes with related profiles of expression define a TIE receptor tyrosine kinase family" *Oncogene* 8(6):1631–1637 (Jun. 1993).
Partanen et al., "Putative Tyrosine Kinases Expressed in K–562 Human Leukemia Cells" *Proc. Natl. Acad. Sci.* 87:8913–8917 (1990).
Suri et al., "Requisite role of angiopoietin–1, a ligand for the TIE2 receptor, during embryonic angionesis" *Cell*87(7):1171–1180 (Dec. 27, 1996).
GenBank Accession No. T11442, CHR90008 Homo sapiens genomic clone 14C–1 5' and 3' similar to fibrogen–like domain, accessed Jan. 7, 1999 (Nov. 1993).
Maisonpierre et al., "Angiopoietin–2, a Natural Antagonist for Tie2 That Disrupts in vivo Angiogenesis" *Science*, 277:55–60 (Jul. 4, 1997).

* cited by examiner

Primary Examiner—Lorraine Spector
Assistant Examiner—Claire M. Kaufman
(74) Attorney, Agent, or Firm—Knobbe, Martens, Olson & Bear LLP

(57) ABSTRACT

The present invention concerns isolated nucleic acid molecules encoding the novel TIE ligands NL1, NL5, NL8, and NL4, the proteins encoded by such nucleic acid molecules, as well as methods and means for making and using such nucleic acid and protein molecules.

18 Claims, 32 Drawing Sheets

```
GCGGACGCGT GGGTGAAATT GAAAATCAAG ATAAAAATGT TCACAATTAA   50
GCTCCTTCTT TTTATTGTTC CTCTAGTTAT TTCCTCCAGA ATTGATCAAG  100
ACAATTCATC ATTTGATTCT CTATCTCCAG AGCCAAAATC AAGATTTGCT  150
ATGTTAGACG ATGTAAAAAT TTTAGCCAAT GGCCTCCTTC AGTTGGGACA  200
TGGTCTTAAA GACTTTGTCC ATAAGACGAA GGGCCAAATT AATGACATAT  250
TTCAAAAACT CAACATATTT GATCAGTCTT TTTATGATCT ATCGCTGCAA  300
ACCAGTGAAA TCAAAGAAGA AGAAAAGGAA CTGAGAAGAA CTACATATAA  350
ACTACAAGTC AAAAATGAAG AGGTAAAGAA TATGTCACTT GAACTCAACT  400
CAAAACTTGA AAGCCTCCTA GAAGAAAAAA TTCTACTTCA ACAAAAAGTG  450
AAATATTTAG AAGAGCAACT AACTAACTTA ATTCAAAATC AACCTGAAAC  500
TCCAGAACAC CCAGAAGTAA CTTCACTTAA AACTTTTGTA GAAAAACAAG  550
ATAATAGCAT CAAAGACCTT CTCCAGACCG TGGAAGACCA ATATAAACAA  600
TTAAACCAAC AGCATAGTCA AATAAAAGAA ATAGAAAATC AGCTCAGAAG  650
GACTAGTATT CAAGAACCCA CAGAAATTTC TCTATCTTCC AAGCCAAGAG  700
CACCAAGAAC TACTCCCTTT CTTCAGTTGA ATGAAATAAG AAATGTAAAA  750
CATGATGGCA TTCCTGCTGA ATGTACCACC ATTTATAACA GAGGTGAACA  800
TACAAGTGGC ATGTATGCCA TCAGACCCAG CAACTCTCAA GTTTTTCATG  850
TCTACTGTGA TGTTATATCA GGTAGTCCAT GGACATTAAT TCAACATCGA  900
ATAGATGGAT CACAAAACTT CAATGAAACG TGGGAGAACT ACAAATATGG  950
TTTTGGGAGG CTTGATGGAG AATTTTGGTT GGGCCTAGAG AAGATATACT 1000
CCATAGTGAA GCAATCTAAT TATGTTTTAC GAATTGAGTT GGAAGACTGG 1050
AAAGACAACA AACATTATAT TGAATATTCT TTTTACTTGG AAATCACGA  1100
AACCAACTAT ACGCTACATC TAGTTGCGAT TACTGGCAAT GTCCCCAATG 1150
CAATCCCGGA AAACAAAGAT TGGTGTTTT CTACTTGGGA TCACAAAGCA 1200
AAAGGACACT TCAACTGTCC AGAGGGTTAT TCAGGAGGCT GGTGGTGGCA 1250
```

FIG. 1A-1

```
TGATGAGTGT GGAGAAAACA ACCTAAATGG TAAATATAAC AAACCAAGAG 1300

CAAAATCTAA GCCAGAGAGG AGAAGAGGAT TATCTTGGAA GTCTCAAAAT 1350

GGAAGGTTAT ACTCTATAAA ATCAACCAAA ATGTTGATCC ATCCAACAGA 1400

TTCAGAAAGC TTTGAATGAA CTGAGGCAAT TTAAAGGCAT ATTTAACCAT 1450

TAACTCATTC CAAGTTAATG TGGTCTAATA ATCTGGTATA AATCCTTAAG 1500

AGAAAGCTTG AGAAATAGAT TTTTTTTATC TTAAAGTCAC TGTCTATTTA 1550

AGATTAAACA TACAATCACA TAACCTTAAA GAATACCGTT TACATTTCTC 1600

AATCAAAATT CTTATAATAC TATTTGTTTT AAATTTTGTG ATGTGGGAAT 1650

CAATTTTAGA TGGTCACAAT CTAGATTATA ATCAATAGGT GAACTTATTA 1700

AATAACTTTT CTAAATAAAA AATTTAGAGA CTTTTATTTT AAAAGGCATC 1750

ATATGAGCTA ATATCACAAC TTTCCCAGTT TAAAAAACTA GTACTCTTGT 1800

TAAAACTCTA AACTTGACTA AATACAGAGG ACTGGTAATT GTACAGTTCT 1850

TAAATGTTGT AGTATTAATT TCAAAACTAA AAATCGTCAG CACAGAGTAT 1900

GTGTAAAAAT CTGTAATACA AATTTTTAAA CTGATGCTTC ATTTTGCTAC 1950

AAAATAATTT GGAGTAAATG TTTGATATGA TTTATTTATG AAACCTAATG 2000

AAGCAGAATT AAATACTGTA TTAAAATAAG TTCGCTGTCT TT 2042
```

FIG. 1A-2

```
Met Phe Thr Ile Lys Leu Leu Leu Phe Ile Val Pro Leu Val Ile
 1               5                   10                  15

Ser Ser Arg Ile Asp Gln Asp Asn Ser Ser Phe Asp Ser Leu Ser
                 20                  25                  30

Pro Glu Pro Lys Ser Arg Phe Ala Met Leu Asp Asp Val Lys Ile
                 35                  40                  45

Leu Ala Asn Gly Leu Leu Gln Leu Gly His Gly Leu Lys Asp Phe
                 50                  55                  60

Val His Lys Thr Lys Gly Gln Ile Asn Asp Ile Phe Gln Lys Leu
                 65                  70                  75

Asn Ile Phe Asp Gln Ser Phe Tyr Asp Leu Ser Leu Gln Thr Ser
                 80                  85                  90

Glu Ile Lys Glu Glu Glu Lys Glu Leu Arg Arg Thr Thr Tyr Lys
                 95                 100                 105

Leu Gln Val Lys Asn Glu Glu Val Lys Asn Met Ser Leu Glu Leu
                110                 115                 120

Asn Ser Lys Leu Glu Ser Leu Leu Glu Glu Lys Ile Leu Leu Gln
                125                 130                 135

Gln Lys Val Lys Tyr Leu Glu Glu Gln Leu Thr Asn Leu Ile Gln
                140                 145                 150

Asn Gln Pro Glu Thr Pro Glu His Pro Glu Val Thr Ser Leu Lys
                155                 160                 165

Thr Phe Val Glu Lys Gln Asp Asn Ser Ile Lys Asp Leu Leu Gln
                170                 175                 180

Thr Val Glu Asp Gln Tyr Lys Gln Leu Asn Gln Gln His Ser Gln
                185                 190                 195

Ile Lys Glu Ile Glu Asn Gln Leu Arg Arg Thr Ser Ile Gln Glu
                200                 205                 210

Pro Thr Glu Ile Ser Leu Ser Ser Lys Pro Arg Ala Pro Arg Thr
                215                 220                 225

Thr Pro Phe Leu Gln Leu Asn Glu Ile Arg Asn Val Lys His Asp
                230                 235                 240
```

FIG. 1B-1

Gly Ile Pro Ala Glu Cys Thr Thr Ile Tyr Asn Arg Gly Glu His
                245                     250                     255

Thr Ser Gly Met Tyr Ala Ile Arg Pro Ser Asn Ser Gln Val Phe
                260                     265                     270

His Val Tyr Cys Asp Val Ile Ser Gly Ser Pro Trp Thr Leu Ile
                275                     280                     285

Gln His Arg Ile Asp Gly Ser Gln Asn Phe Asn Glu Thr Trp Glu
                290                     295                     300

Asn Tyr Lys Tyr Gly Phe Gly Arg Leu Asp Gly Glu Phe Trp Leu
                305                     310                     315

Gly Leu Glu Lys Ile Tyr Ser Ile Val Lys Gln Ser Asn Tyr Val
                320                     325                     330

Leu Arg Ile Glu Leu Glu Asp Trp Lys Asp Asn Lys His Tyr Ile
                335                     340                     345

Glu Tyr Ser Phe Tyr Leu Gly Asn His Glu Thr Asn Tyr Thr Leu
                350                     355                     360

His Leu Val Ala Ile Thr Gly Asn Val Pro Asn Ala Ile Pro Glu
                365                     370                     375

Asn Lys Asp Leu Val Phe Ser Thr Trp Asp His Lys Ala Lys Gly
                380                     385                     390

His Phe Asn Cys Pro Glu Gly Tyr Ser Gly Gly Trp Trp Trp His
                395                     400                     405

Asp Glu Cys Gly Glu Asn Asn Leu Asn Gly Lys Tyr Asn Lys Pro
                410                     415                     420

Arg Ala Lys Ser Lys Pro Glu Arg Arg Arg Gly Leu Ser Trp Lys
                425                     430                     435

Ser Gln Asn Gly Arg Leu Tyr Ser Ile Lys Ser Thr Lys Met Leu
                440                     445                     450

Ile His Pro Thr Asp Ser Glu Ser Phe Glu
                455                     460

FIG. 1B-2

```
GGCTGAGGGG AGGCCCGGAG CCTTTCTGGG GCCTGGGGGA TCCTCTTGCA  50
CTGGTGGGTG GAGAGAAGCG CCTGCAGCCA ACCAGGGTCA GGCTGTGCTC 100
ACAGTTTCCT CTGGCGGCAT GTAAAGGCTC CACAAAGGAG TTGGGAGTTC 150
AAATGAGGCT GCTGCGGACG GCCTGAGGAT GGACCCCAAG CCCTGGACCT 200
GCCGAGCGTG GCACTGAGGC AGCGGCTGAC GCTACTGTGA GGGAAAGAAG 250
GTTGTGAGCA GCCCCGCAGG ACCCCTGGCC AGCCCTGGCC CCAGCCTCTG 300
CCGGAGCCCT CTGTGGAGGC AGAGCCAGTG GAGCCCAGTG AGGCAGGGCT 350
GCTTGGCAGC CACCGGCCTG CAACTCAGGA ACCCCTCCAG AGGCCATGGA 400
CAGGCTGCCC CGCTGACGGC CAGGGTGAAG CATGTGAGGA GCCGCCCCGG 450
AGCCAAGCAG GAGGGAAGAG GCTTTCATAG ATTCTATTCA CAAAGAATAA 500
CCACCATTTT GCAAGGACCA TGAGGCCACT GTGCGTGACA TGCTGGTGGC 550
TCGGACTGCT GGCTGCCATG GGAGCTGTTG CAGGCCAGGA GGACGGTTTT 600
GAGGGCACTG AGGAGGGCTC GCCAAGAGAG TTCATTTACC TAAACAGGTA 650
CAAGCGGGCG GGCGAGTCCC AGGACAAGTG CACCTACACC TTCATTGTGC 700
CCCAGCAGCG GGTCACGGGT GCCATCTGCG TCAACTCCAA GGAGCCTGAG 750
GTGCTTCTGG AGAACCGAGT GCATAAGCAG GAGCTAGAGC TGCTCAACAA 800
TGAGCTGCTC AAGCAGAAGC GGCAGATCGA GACGCTGCAG CAGCTGGTGG 850
AGGTGGACGG CGGCATTGTG AGCGAGGTGA AGCTGCTGCG CAAGGAGAGC 900
CGCAACATGA ACTCGCGGGT CACGCAGCTC TACATGCAGC TCCTGCACGA 950
GATCATCCGC AAGCGGGACA ACGCGTTGGA GCTCTCCCAG CTGGAGAACA 1000
GGATCCTGAA CCAGACAGCC GACATGCTGC AGCTGGCCAG CAAGTACAAG 1050
GACCTGGAGC ACAAGTACCA GCACCTGGCC ACACTGGCCC ACAACCAATC 1100
AGAGATCATC GCGCAGCTTG AGGAGCACTG CCAGAGGGTG CCCTCGGCCA 1150
GGCCCGTCCC CCAGCCACCC CCCGCTGCCC CGCCCCGGGT CTACCAACCA 1200
```

FIG. 2A

```
CCCACCTACA ACCGCATCAT CAACCAGATC TCTACCAACG AGATCCAGAG 1250
TGACCAGAAC CTGAAGGTGC TGCCACCCCC TCTGCCCACT ATGCCCACTC 1300
TCACCAGCCT CCCATCTTCC ACCGACAAGC CGTCGGGCCC ATGGAGAGAC 1350
TGCCTGCAGG CCCTGGAGGA TGGCCACGAC ACCAGCTCCA TCTACCTGGT 1400
GAAGCCGGAG AACACCAACC GCCTCATGCA GGTGTGGTGC GACCAGAGAC 1450
ACGACCCCGG GGGCTGGACC GTCATCCAGA GACGCCTGGA TGGCTCTGTT 1500
AACTTCTTCA GGAACTGGGA GACGTACAAG CAAGGGTTTG GAACATTGA 1550
CGGCGAATAC TGGCTGGGCC TGGAGAACAT TTACTGGCTG ACGAACCAAG 1600
GCAACTACAA ACTCCTGGTG ACCATGGAGG ACTGGTCCGG CCGCAAAGTC 1650
TTTGCAGAAT ACGCCAGTTT CCGCCTGGAA CCTGAGAGCG AGTATTATAA 1700
GCTGCGGCTG GGGCGCTACC ATGGCAATGC GGGTGACTCC TTTACATGGC 1750
ACAACGGCAA GCAGTTCACC ACCCTGGACA GAGATCATGA TGTCTACACA 1800
GGAAACTGTG CCCACTACCA GAAGGGAGGC TGGTGGTATA ACGCCTGTGC 1850
CCACTCCAAC CTCAACGGGG TCTGGTACCG CGGGGGCCAT TACCGGAGCC 1900
GCTACCAGGA CGGAGTCTAC TGGGCTGAGT TCCGAGGAGG CTCTTACTCA 1950
CTCAAGAAAG TGGTGATGAT GATCCGACCG AACCCCAACA CCTTCCACTA 2000
AGCCAGCTCC CCCTCCTGAC CTCTCGTGGC CATTGCCAGG AGCCCACCCT 2050
GGTCACGCTG GCCACAGCAC AAAGAACAAC TCCTCACCAG TTCATCCTGA 2100
GGCTGGGAGG ACCGGGATGC TGGATTCTGT TTTCCGAAGT CACTGCAGCG 2150
GATGATGGAA CTGAATCGAT ACGGTGTTTT CTGTCCCTCC TACTTTCCTT 2200
CACACCAGAC AGCCCCTCAT GTCTCCAGGA CAGGACAGGA CTACAGACAA 2250
CTCTTTCTTT AAATAAATTA AGTCTCTACA ATAAAAAAAA 2290
```

FIG. 2B

| | | | | | | | | | | | | | | |
|---|---|---|---|---|---|---|---|---|---|---|---|---|---|---|
| Met | Arg | Pro | Leu | Cys | Val | Thr | Cys | Trp | Trp | Leu | Gly | Leu | Leu | Ala |
| 1 | | | | 5 | | | | | 10 | | | | | 15 |
| Ala | Met | Gly | Ala | Val | Ala | Gly | Gln | Glu | Asp | Gly | Phe | Glu | Gly | Thr |
| | | | | 20 | | | | | 25 | | | | | 30 |
| Glu | Glu | Gly | Ser | Pro | Arg | Glu | Phe | Ile | Tyr | Leu | Asn | Arg | Tyr | Lys |
| | | | | 35 | | | | | 40 | | | | | 45 |
| Arg | Ala | Gly | Glu | Ser | Gln | Asp | Lys | Cys | Thr | Tyr | Thr | Phe | Ile | Val |
| | | | | 50 | | | | | 55 | | | | | 60 |
| Pro | Gln | Gln | Arg | Val | Thr | Gly | Ala | Ile | Cys | Val | Asn | Ser | Lys | Glu |
| | | | | 65 | | | | | 70 | | | | | 75 |
| Pro | Glu | Val | Leu | Leu | Glu | Asn | Arg | Val | His | Lys | Gln | Glu | Leu | Glu |
| | | | | 80 | | | | | 85 | | | | | 90 |
| Leu | Leu | Asn | Asn | Glu | Leu | Leu | Lys | Gln | Lys | Arg | Gln | Ile | Glu | Thr |
| | | | | 95 | | | | | 100 | | | | | 105 |
| Leu | Gln | Gln | Leu | Val | Glu | Val | Asp | Gly | Gly | Ile | Val | Ser | Glu | Val |
| | | | | 110 | | | | | 115 | | | | | 120 |
| Lys | Leu | Leu | Arg | Lys | Glu | Ser | Arg | Asn | Met | Asn | Ser | Arg | Val | Thr |
| | | | | 125 | | | | | 130 | | | | | 135 |
| Gln | Leu | Tyr | Met | Gln | Leu | Leu | His | Glu | Ile | Ile | Arg | Lys | Arg | Asp |
| | | | | 140 | | | | | 145 | | | | | 150 |
| Asn | Ala | Leu | Glu | Leu | Ser | Gln | Leu | Glu | Asn | Arg | Ile | Leu | Asn | Gln |
| | | | | 155 | | | | | 160 | | | | | 165 |
| Thr | Ala | Asp | Met | Leu | Gln | Leu | Ala | Ser | Lys | Tyr | Lys | Asp | Leu | Glu |
| | | | | 170 | | | | | 175 | | | | | 180 |
| His | Lys | Tyr | Gln | His | Leu | Ala | Thr | Leu | Ala | His | Asn | Gln | Ser | Glu |
| | | | | 185 | | | | | 190 | | | | | 195 |
| Ile | Ile | Ala | Gln | Leu | Glu | Glu | His | Cys | Gln | Arg | Val | Pro | Ser | Ala |
| | | | | 200 | | | | | 205 | | | | | 210 |
| Arg | Pro | Val | Pro | Gln | Pro | Pro | Pro | Ala | Ala | Pro | Pro | Arg | Val | Tyr |
| | | | | 215 | | | | | 220 | | | | | 225 |
| Gln | Pro | Pro | Thr | Tyr | Asn | Arg | Ile | Ile | Asn | Gln | Ile | Ser | Thr | Asn |
| | | | | 230 | | | | | 235 | | | | | 240 |
| Glu | Ile | Gln | Ser | Asp | Gln | Asn | Leu | Lys | Val | Leu | Pro | Pro | Pro | Leu |
| | | | | 245 | | | | | 250 | | | | | 255 |

FIG. 3A

Pro Thr Met Pro Thr Leu Thr Ser Leu Pro Ser Ser Thr Asp Lys
                    260             265             270

Pro Ser Gly Pro Trp Arg Asp Cys Leu Gln Ala Leu Glu Asp Gly
                275             280             285

His Asp Thr Ser Ser Ile Tyr Leu Val Lys Pro Glu Asn Thr Asn
                290             295             300

Arg Leu Met Gln Val Trp Cys Asp Gln Arg His Asp Pro Gly Gly
                305             310             315

Trp Thr Val Ile Gln Arg Arg Leu Asp Gly Ser Val Asn Phe Phe
                320             325             330

Arg Asn Trp Glu Thr Tyr Lys Gln Gly Phe Gly Asn Ile Asp Gly
                335             340             345

Glu Tyr Trp Leu Gly Leu Glu Asn Ile Tyr Trp Leu Thr Asn Gln
                350             355             360

Gly Asn Tyr Lys Leu Leu Val Thr Met Glu Asp Trp Ser Gly Arg
                365             370             375

Lys Val Phe Ala Glu Tyr Ala Ser Phe Arg Leu Glu Pro Glu Ser
                380             385             390

Glu Tyr Tyr Lys Leu Arg Leu Gly Arg Tyr His Gly Asn Ala Gly
                395             400             405

Asp Ser Phe Thr Trp His Asn Gly Lys Gln Phe Thr Thr Leu Asp
                410             415             420

Arg Asp His Asp Val Tyr Thr Gly Asn Cys Ala His Tyr Gln Lys
                425             430             435

Gly Gly Trp Trp Tyr Asn Ala Cys Ala His Ser Asn Leu Asn Gly
                440             445             450

Val Trp Tyr Arg Gly Gly His Tyr Arg Ser Arg Tyr Gln Asp Gly
                455             460             465

Val Tyr Trp Ala Glu Phe Arg Gly Gly Ser Tyr Ser Leu Lys Lys
                470             475             480

Val Val Met Met Ile Arg Pro Asn Pro Asn Thr Phe His
                485             490         493

FIG. 3B

```
GCAGCTGGTT ACTGCATTTC TCCATGTGGC AGACAGAGCA AAGCCACAAC  50
GCTTTCTCTG CTGGATTAAA GACGGCCCAC AGACCAGAAC TTCCACTATA 100
CTACTTAAAA TTACATAGGT GGCTTGTCAA ATTCAATTGA TTAGTATTGT 150
AAAAGGAAAA AGAAGTTCCT TCTTACAGCT TGGATTCAAC GGTCCAAAAC 200
AAAAATGCAG CTGCCATTAA AGTCTCAGAT GAACAAACTT CTACACTGAT 250
TTTTAAAATC AAGAATAAGG GCAGCAAGTT TCTGGATTCA CTGAATCAAC 300
AGACACAAAA AGCTGGCAAT ATAGCAACTA TGAAGAGAAA AGCTACTAAT 350
AAAATTAACC CAACGCATAG AAGACTTTTT TTTCTCTTCT AAAAACAACT 400
AAGTAAAGAC TTAAATTTAA ACACATCATT TTACAACCTC ATTTCAAAAT 450
GAAGACTTTT ACCTGGACCC TAGGTGTGCT ATTCTTCCTA CTAGTGGACA 500
CTGGACATTG CAGAGGTGGA CAATTCAAAA TTAAAAAAAT AAACCAGAGA 550
AGATACCCTC GTGCCACAGA TGGTAAAGAG GAAGCAAAGA AATGTGCATA 600
CACATTCCTG GTACCTGAAC AAAGAATAAC AGGGCCAATC TGTGTCAACA 650
CCAAGGGGCA AGATGCAAGT ACCATTAAAG ACATGATCAC CAGGATGGAC 700
CTTGAAAACC TGAAGGATGT GCTCTCCAGG CAGAAGCGGG AGATAGATGT 750
TCTGCAACTG GTGGTGGATG TAGATGGAAA CATTGTGAAT GAGGTAAAGC 800
TGCTGAGAAA GGAAAGCCGT AACATGAACT CTCGTGTTAC TCAACTCTAT 850
ATGCAATTAT TACATGAGAT TATCCGTAAG AGGGATAATT CACTTGAACT 900
TTCCCAACTG GAAAACAAAA TCCTCAATGT CACCACAGAA ATGTTGAAGA 950
TGGCAACAAG ATACAGGGAA CTAGAGGTGA AATACGCTTC CTTGACTGAT 1000
CTTGTCAATA ACCAATCTGT GATGATCACT TTGTTGGAAG AACAGTGCTT 1050
GAGGATATTT TCCCGACAAG ACACCCATGT GTCTCCCCA CTTGTCCAGG 1100
TGGTGCCACA ACATATTCCT AACAGCCAAC AGTATACTCC TGGTCTGCTG 1150
GGAGGTAACG AGATTCAGAG GGATCCAGGT TATCCCAGAG ATTTAATGCC 1200
```

FIG. 4A

```
ACCACCTGAT CTGGCAACTT CTCCCACCAA AAGCCCTTTC AAGATACCAC 1250
CGGTAACTTT CATCAATGAA GGACCATTCA AAGACTGTCA GCAAGCAAAA 1300
GAAGCTGGGC ATTCGGTCAG TGGGATTTAT ATGATTAAAC CTGAAAACAG 1350
CAATGGACCA ATGCAGTTAT GGTGTGAAAA CAGTTTGGAC CCTGGGGGTT 1400
GGACTGTTAT TCAGAAAAGA ACAGACGGCT CTGTCAACTT CTTCAGAAAT 1450
TGGGAAAATT ATAAGAAGG GTTTGGAAAC ATTGACGGAG AATACTGGCT 1500
TGGACTGGAA AATATCTATA TGCTTAGCAA TCAAGATAAT TACAAGTTAT 1550
TGATTGAATT AGAAGACTGG AGTGATAAAA AAGTCTATGC AGAATACAGC 1600
AGCTTTCGTC TGGAACCTGA AAGTGAATTC TATAGACTGC GCCTGGGAAC 1650
TTACCAGGGA AATGCAGGGG ATTCTATGAT. GTGGCATAAT GGTAAACAAT 1700
TCACCACACT GGACAGAGAT AAAGATATGT ATGCAGGAAA CTGCGCCCAC 1750
TTTCATAAAG GAGGCTGGTG GTACAATGCC TGTGCACATT CTAACCTAAA 1800
TGGAGTATGG TACAGAGGAG CCATTACAG AAGCAAGCAC CAAGATGGAA 1850
TTTTCTGGGC CGAATACAGA GGCGGGTCAT ACTCCTTAAG AGCAGTTCAG 1900
ATGATGATCA AGCCTATTGA CTGAAGAGAG ACACTCGCCA ATTTAAATGA 1950
CACAGAACTT TGTACTTTTC AGCTCTTAAA AATGTAAATG TTACATGTAT 2000
ATTACTTGGC ACAATTTATT TCTACACAGA AAGTTTTTAA AATGAATTTT 2050
ACCGTAACTA TAAAAGGGAA CCTATAAATG TAGTTTCATC TGTCGTCAAT 2100
TACTGCAGAA AATTATGTGT ATCCACAACC TAGTTATTTT AAAAATTATG 2150
TTGACTAAAT ACAAAGTTTG TTTTCTAAAA TGTAAATATT TGCCACAATG 2200
TAAAGCAAAT CTTAGCTATA TTTTAAATCA TAAATAACAT GTTCAAGATA 2250
CTTAACAATT TATTTAAAAT CTAAGATTGC TCTAACGTCT AGTGAAAAAA 2300
ATATTTTTTA AATTTCAGCC AAATAATGCA TTTTATTTTA TAAAAATACA 2350
GACAGAAAAT TAGGGAGAAA CTTCTAGTTT TGCCAATAGA AAATGTTCTT 2400
```

FIG. 4B

```
CCATTGAATA AAAGTTATTT CAAATTGAAT TTGTGCCTTT CACACGTAAT 2450

GATTAAATCT GAATTCTTAA TAATATATCC TATGCTGATT TTCCCAAAAC 2500

ATGACCCATA GTATTAAATA CATATCATTT TTAAAAATAA AAAAAAACCC 2550

AAAAATAATG CATGCATAAT TTAAATGGTC AATTTATAAA GACAAATCTA 2600

TGAATGAATT TTTCAGTGTT ATCTTCATAT GATATGCTGA ACACCAAAAT 2650

CTCCAGAAAT GCATTTTATG TAGTTCTAAA ATCAGCAAAA TATTGGTATT 2700

ACAAAAATGC AGAATATTTA GTGTGCTACA GATCTGAATT ATAGTTCTAA 2750

TTTATTATTA CTTTTTTTCT AATTTACTGA TCTTACTACT ACAAAGAAAA 2800

AAAAACCCAA CCCATCTGCA ATTCAAATCA GAAAGTTTGG ACAGCTTTAC 2850

AAGTATTAGT GCATGCTCAG AACAGGTGGG ACTAAAACAA ACTCAAGGAA 2900

CTGTTGGCTG TTTTCCCGAT ACTGAGAATT CAACAGCTCC AGAGCAGAAG 2950

CCACAGGGGC ATAGCTTAGT CCAAACTGCT AATTTCATTT TACAGTGTAT 3000

GTAACGCTTA GTCTCACAGT GTCTTTAACT CATCTTTGCA ATCAACAACT 3050

TTACTAGTGA CTTTCTGGAA CAATTTCCTT TCAGGAATAC ATATTCACTG 3100

CTTAGAGGTG ACCTTGCCTT AATATATTTG TGAAGTTAAA ATTTTAAAGA 3150

TAGCTCATGA AACTTTTGCT TAAGCAAAAA GAAAACCTCG AATTGAAATG 3200

TGTGAGGCAA ACTATGCATG GAATAGCTT AATGTGAAGA TAATCATTTG 3250

GACAACTCAA ATCCATCAAC ATGACCAATG TTTTTCATCT GCCACATCTC 3300

AAAATAAAAC TTCTGGTGAA ACAAATTAAA CAAAATATCC AAACCTCAAA 3350

AAAAA 3355
```

FIG. 4C

Met Lys Thr Phe Thr Trp Thr Leu Gly Val Leu Phe Phe Leu Leu
1               5                   10                  15

Val Asp Thr Gly His Cys Arg Gly Gly Gln Phe Lys Ile Lys Lys
                20                  25                  30

Ile Asn Gln Arg Arg Tyr Pro Arg Ala Thr Asp Gly Lys Glu Glu
                35                  40                  45

Ala Lys Lys Cys Ala Tyr Thr Phe Leu Val Pro Glu Gln Arg Ile
                50                  55                  60

Thr Gly Pro Ile Cys Val Asn Thr Lys Gly Gln Asp Ala Ser Thr
                65                  70                  75

Ile Lys Asp Met Ile Thr Arg Met Asp Leu Glu Asn Leu Lys Asp
                80                  85                  90

Val Leu Ser Arg Gln Lys Arg Glu Ile Asp Val Leu Gln Leu Val
                95                  100                 105

Val Asp Val Asp Gly Asn Ile Val Asn Glu Val Lys Leu Leu Arg
                110                 115                 120

Lys Glu Ser Arg Asn Met Asn Ser Arg Val Thr Gln Leu Tyr Met
                125                 130                 135

Gln Leu Leu His Glu Ile Ile Arg Lys Arg Asp Asn Ser Leu Glu
                140                 145                 150

Leu Ser Gln Leu Glu Asn Lys Ile Leu Asn Val Thr Thr Glu Met
                155                 160                 165

Leu Lys Met Ala Thr Arg Tyr Arg Glu Leu Glu Val Lys Tyr Ala
                170                 175                 180

Ser Leu Thr Asp Leu Val Asn Asn Gln Ser Val Met Ile Thr Leu
                185                 190                 195

Leu Glu Glu Gln Cys Leu Arg Ile Phe Ser Arg Gln Asp Thr His
                200                 205                 210

Val Ser Pro Pro Leu Val Gln Val Val Pro Gln His Ile Pro Asn
                215                 220                 225

Ser Gln Gln Tyr Thr Pro Gly Leu Leu Gly Gly Asn Glu Ile Gln
                230                 235                 240

Arg Asp Pro Gly Tyr Pro Arg Asp Leu Met Pro Pro Pro Asp Leu
                245                 250                 255

FIG. 5A

```
Ala Thr Ser Pro Thr Lys Ser Pro Phe Lys Ile Pro Pro Val Thr
            260             265             270
Phe Ile Asn Glu Gly Pro Phe Lys Asp Cys Gln Gln Ala Lys Glu
            275             280             285
Ala Gly His Ser Val Ser Gly Ile Tyr Met Ile Lys Pro Glu Asn
            290             295             300
Ser Asn Gly Pro Met Gln Leu Trp Cys Glu Asn Ser Leu Asp Pro
            305             310             315
Gly Gly Trp Thr Val Ile Gln Lys Arg Thr Asp Gly Ser Val Asn
            320             325             330
Phe Phe Arg Asn Trp Glu Asn Tyr Lys Lys Gly Phe Gly Asn Ile
            335             340             345
Asp Gly Glu Tyr Trp Leu Gly Leu Glu Asn Ile Tyr Met Leu Ser
            350             355             360
Asn Gln Asp Asn Tyr Lys Leu Leu Ile Glu Leu Glu Asp Trp Ser
            365             370             375
Asp Lys Lys Val Tyr Ala Glu Tyr Ser Ser Phe Arg Leu Glu Pro
            380             385             390
Glu Ser Glu Phe Tyr Arg Leu Arg Leu Gly Thr Tyr Gln Gly Asn
            395             400             405
Ala Gly Asp Ser Met Met Trp His Asn Gly Lys Gln Phe Thr Thr
            410             415             420
Leu Asp Arg Asp Lys Asp Met Tyr Ala Gly Asn Cys Ala His Phe
            425             430             435
His Lys Gly Gly Trp Trp Tyr Asn Ala Cys Ala His Ser Asn Leu
            440             445             450
Asn Gly Val Trp Tyr Arg Gly Gly His Tyr Arg Ser Lys His Gln
            455             460             465
Asp Gly Ile Phe Trp Ala Glu Tyr Arg Gly Gly Ser Tyr Ser Leu
            470             475             480
Arg Ala Val Gln Met Met Ile Lys Pro Ile Asp
            485             490 491
```

FIG. 5B

```
GGCTCAGAGG CCCCACTGGA CCCTCGGCTC TTCCTTGGAC TTCTTGTGTG  50

TTCTGTGAGC TTCGCTGGAT TCAGGGTCTT GGGCATCAGA GGTGAGAGGG 100

TGGGAAGGTC CGCCGCGATG GGGAAGCCCT GGCTGCGTGC GCTACAGCTG 150

CTGCTCCTGC TGGGCGCGTC GTGGGCGCGG GCGGGCGCCC CGCGCTGCAC 200

CTACACCTTC GTGCTGCCCC CGCAGAAGTT CACGGGCGCT GTGTGCTGGA 250

GCGGCCCCGC ATCCACGCGG GCGACGCCCG AGGCCGCCAA CGCCAGCGAG 300

CTGGCGGCGC TGCGCATGCG CGTCGGCCGC CACGAGGAGC TGTTACGCGA 350

GCTGCAGAGG CTGGCGGCGG CCGACGGCGC CGTGGCCGGC GAGGTGCGCG 400

CGCTGCGCAA GGAGAGCCGC GGCCTGAGCG CGCGCCTGGG CCAGTTGCGC 450

GCGCAGCTGC AGCACGAGGC GGGGCCCGGG GCGGGCCCGG GGCGGATCT 500

GGGGGCGGAG CCTGCCGCGG CGCTGGCGCT GCTCGGGGAG CGCGTGCTCA 550

ACGCGTCCGC CGAGGCTCAG CGCGCAGCCG CCCGGTTCCA CCAGCTGGAC 600

GTCAAGTTCC GCGAGCTGGC GCAGCTCGTC ACCCAGCAGA GCAGTCTCAT 650

CGCCCGCCTG GAGCGCCTGT GCCCGGGAGG CGCGGGCGGG CAGCAGCAGG 700

TCCTGCCGCC ACCCCCACTG GTGCCTGTGG TTCCGGTCCG TCTTGTGGGT 750

AGCACCAGTG ACACCAGTAG GATGCTGGAC CCAGCCCCAG AGCCCCAGAG 800

AGACCAGACC CAGAGACAGC AGGAGCCCAT GGCTTCTCCC ATGCCTGCAG 850

GTCACCCTGC GGTCCCCACC AAGCCTGTGG GCCCGTGGCA GGATTGTGCA 900

GAGGCCCGCC AGGCAGGCCA TGAACAGAGT GGAGTGTATG AACTGCGAGT 950

GGGCCGTCAC GTAGTGTCAG TATGGTGTGA GCAGCAACTG GAGGGTGGAG 1000

GCTGGACTGT GATCCAGCGG AGGCAAGATG GTTCAGTCAA CTTCTTCACT 1050

ACCTGGCAGC ACTATAAGGC GGGCTTTGGG CGGCCAGACG GAGAATACTG 1100

GCTGGGCCTT GAACCCGTGT ATCAGCTGAC CAGCCGTGGG GACCATGAGC 1150

TGCTGGTTCT CCTGGAGGAC TGGGGGGGCC GTGGAGCACG TGCCCACTAT 1200
```

FIG. 6A

```
GATGGCTTCT CCCTGGAACC CGAGAGCGAC CACTACCGCC TGCGGCTTGG 1250

CCAGTACCAT GGTGATGCTG GAGACTCTCT TTCCTGGCAC AATGACAAGC 1300

CCTTCAGCAC CGTGGATAGG GACCGAGACT CCTATTCTGG TAACTGTGCC 1350

CTGTACCAGC GGGGAGGCTG GTGGTACCAT GCCTGTGCCC ACTCCAACCT 1400

CAACGGTGTG TGGCACCACG GCGGCCACTA CCGAAGCCGC TACCAGGATG 1450

GTGTCTACTG GGCTGAGTTT CGTGGTGGGG CATATTCTCT CAGGAAGGCC 1500

GCCATGCTCA TTCGGCCCCT GAAGCTGTGA CTCTGTGTTC CTCTGTCCCC 1550

TAGGCCCTAG AGGACATTGG TCAGCAGGAG CCCAAGTTGT TCTGGCCACA 1600

CCTTCTTTGT GGCTCAGTGC CAATGTGTCC CACAGAACTT CCCACTGTGG 1650

ATCTGTGACC CTGGGCGCTG AAAATGGGAC CCAGGAATCC CCCCGTCAA 1700

TATCTTGGCC TCAGATGGCT CCCCAAGGTC ATTCATATCT CGGTTTGAGC 1750

TCATATCTTA TAATAACACA AAGTAGCCAC 1780
```

FIG. 6B

| | | | | | | | | | | | | | | |
|---|---|---|---|---|---|---|---|---|---|---|---|---|---|---|
|Met|Gly|Lys|Pro|Trp|Leu|Arg|Ala|Leu|Gln|Leu|Leu|Leu|Leu|Leu|
|1| | | |5| | | | |10| | | | |15|
|Gly|Ala|Ser|Trp|Ala|Arg|Ala|Gly|Ala|Pro|Arg|Cys|Thr|Tyr|Thr|
| | | | |20| | | | |25| | | | |30|
|Phe|Val|Leu|Pro|Pro|Gln|Lys|Phe|Thr|Gly|Ala|Val|Cys|Trp|Ser|
| | | | |35| | | | |40| | | | |45|
|Gly|Pro|Ala|Ser|Thr|Arg|Ala|Thr|Pro|Glu|Ala|Ala|Asn|Ala|Ser|
| | | | |50| | | | |55| | | | |60|
|Glu|Leu|Ala|Ala|Leu|Arg|Met|Arg|Val|Gly|Arg|His|Glu|Glu|Leu|
| | | | |65| | | | |70| | | | |75|
|Leu|Arg|Glu|Leu|Gln|Arg|Leu|Ala|Ala|Ala|Asp|Gly|Ala|Val|Ala|
| | | | |80| | | | |85| | | | |90|
|Gly|Glu|Val|Arg|Ala|Leu|Arg|Lys|Glu|Ser|Arg|Gly|Leu|Ser|Ala|
| | | | |95| | | | |100| | | | |105|
|Arg|Leu|Gly|Gln|Leu|Arg|Ala|Gln|Leu|Gln|His|Glu|Ala|Gly|Pro|
| | | | |110| | | | |115| | | | |120|
|Gly|Ala|Gly|Pro|Gly|Ala|Asp|Leu|Gly|Ala|Glu|Pro|Ala|Ala|Ala|
| | | | |125| | | | |130| | | | |135|
|Leu|Ala|Leu|Leu|Gly|Glu|Arg|Val|Leu|Asn|Ala|Ser|Ala|Glu|Ala|
| | | | |140| | | | |145| | | | |150|
|Gln|Arg|Ala|Ala|Ala|Arg|Phe|His|Gln|Leu|Asp|Val|Lys|Phe|Arg|
| | | | |155| | | | |160| | | | |165|
|Glu|Leu|Ala|Gln|Leu|Val|Thr|Gln|Gln|Ser|Ser|Leu|Ile|Ala|Arg|
| | | | |170| | | | |175| | | | |180|
|Leu|Glu|Arg|Leu|Cys|Pro|Gly|Gly|Ala|Gly|Gly|Gln|Gln|Gln|Val|
| | | | |185| | | | |190| | | | |195|
|Leu|Pro|Pro|Pro|Pro|Leu|Val|Pro|Val|Val|Pro|Val|Arg|Leu|Val|
| | | | |200| | | | |205| | | | |210|
|Gly|Ser|Thr|Ser|Asp|Thr|Ser|Arg|Met|Leu|Asp|Pro|Ala|Pro|Glu|
| | | | |215| | | | |220| | | | |225|
|Pro|Gln|Arg|Asp|Gln|Thr|Gln|Arg|Gln|Gln|Glu|Pro|Met|Ala|Ser|
| | | | |230| | | | |235| | | | |240|
|Pro|Met|Pro|Ala|Gly|His|Pro|Ala|Val|Pro|Thr|Lys|Pro|Val|Gly|
| | | | |245| | | | |250| | | | |255|

FIG. 7A

```
Pro Trp Gln Asp Cys Ala Glu Ala Arg Gln Ala Gly His Glu Gln
            260                 265                 270
Ser Gly Val Tyr Glu Leu Arg Val Gly Arg His Val Val Ser Val
            275                 280                 285
Trp Cys Glu Gln Gln Leu Glu Gly Gly Gly Trp Thr Val Ile Gln
            290                 295                 300
Arg Arg Gln Asp Gly Ser Val Asn Phe Phe Thr Thr Trp Gln His
            305                 310                 315
Tyr Lys Ala Gly Phe Gly Arg Pro Asp Gly Glu Tyr Trp Leu Gly
            320                 325                 330
Leu Glu Pro Val Tyr Gln Leu Thr Ser Arg Gly Asp His Glu Leu
            335                 340                 345
Leu Val Leu Leu Glu Asp Trp Gly Gly Arg Gly Ala Arg Ala His
            350                 355                 360
Tyr Asp Gly Phe Ser Leu Glu Pro Glu Ser Asp His Tyr Arg Leu
            365                 370                 375
Arg Leu Gly Gln Tyr His Gly Asp Ala Gly Asp Ser Leu Ser Trp
            380                 385                 390
His Asn Asp Lys Pro Phe Ser Thr Val Asp Arg Asp Arg Asp Ser
            395                 400                 405
Tyr Ser Gly Asn Cys Ala Leu Tyr Gln Arg Gly Gly Trp Trp Tyr
            410                 415                 420
His Ala Cys Ala His Ser Asn Leu Asn Gly Val Trp His His Gly
            425                 430                 435
Gly His Tyr Arg Ser Arg Tyr Gln Asp Gly Val Tyr Trp Ala Glu
            440                 445                 450
Phe Arg Gly Gly Ala Tyr Ser Leu Arg Lys Ala Ala Met Leu Ile
            455                 460                 465
Arg Pro Leu Lys Leu
            470
```

FIG. 7B

DNA 22779 DARK FIELD

THE WHITE SPOTS REPRESENT THE SILVER GRAINS.

DNA 28497 DARK FIELD

THE WHITE SPOTS REPRESENT THE SILVER GRAINS.

DNA 23339 DARK FIELD

THE WHITE SPOTS REPRESENT THE SILVER GRAINS.

```
GAAAGCTATA GGCTACCCAT TCAGCTCCCC TGTCAGAGAC TCAAGCTTTG   50
AGAAAGGCTA GCAAAGAGCA AGGAAAGAGA GAAAACAACA AAGTGGCGAG  100
GCCCTCAGAG TGAAAGCGTA AGGTTCAGTC AGCCTGCTGC AGCTTTGCAG  150
ACCTCAGCTG GGCATCTCCA GACTCCCTG AAGGAAGAGC CTTCCTCACC   200
CAAACCCACA AAAGATGCTG AAAAAGCCTC TCTCAGCTGT GACCTGGCTC  250
TGCATTTTCA TCGTGGCCTT TGTCAGCCAC CCAGCGTGGC TGCAGAAGCT  300
CTCTAAGCAC AAGACACCAG CACAGCCACA GCTCAAAGCG GCCAACTGCT  350
GTGAGGAGGT GAAGGAGCTC AAGGCCCAAG TTGCCAACCT TAGCAGCCTG  400
CTGAGTGAAC TGAACAAGAA GCAGGAGAGG GACTGGGTCA GCGTGGTCAT  450
GCAGGTGATG GAGCTGGAGA GCAACAGCAA GCGCATGGAG TCGCGGCTCA  500
CAGATGCTGA GAGCAAGTAC TCCGAGATGA ACAACCAAAT TGACATCATG  550
CAGCTGCAGG CAGCACAGAC GGTCACTCAG ACCTCCGCAG ATGCCATCTA  600
CGACTGCTCT TCCCTCTACC AGAAGAACTA CCGCATCTCT GGAGTGTATA  650
AGCTTCCTCC TGATGACTTC CTGGGCAGCC CTGAACTGGA GGTGTTCTGT  700
GACATGGAGA CTTCAGGCGG AGGCTGGACC ATCATCCAGA GACGAAAAAG  750
TGGCCTTGTC TCCTTCTACC GGGACTGGAA GCAGTACAAG CAGGGCTTTG  800
GCAGCATCCG TGGGGACTTC TGGCTGGGGA ACGAACACAT CCACCGGCTC  850
TCCAGACAGC CAACCCGGCT GCGTGTAGAG ATGGAGGACT GGGAGGGCAA  900
CCTGCGCTAC GCTGAGTATA GCCACTTTGT TTTGGGCAAT GAACTCAACA  950
GCTATCGCCT CTTCCTGGGG AACTACACTG GCAATGTGGG GAACGACGCC 1000
CTCCAGTATC ATAACAACAC AGCCTTCAGC ACCAAGGACA AGGACAATGA 1050
CAACTGCTTG ACAAGTGTG CACAGCTCCG CAAAGGTGGC TACTGGTACA  1100
ACTGCTGCAC AGACTCCAAC CTCAATGGAG TGTACTACCG CCTGGGTGAG 1150
CACAATAAGC ACCTGGATGG CATCACCTGG TATGGCTGGC ATGGATCTAC 1200
```

FIG. 13A

```
CTACTCCCTC AAACGGGTGG AGATGAAAAT CCGCCCAGAA GACTTCAAGC 1250
CTTAAAAGGA GGCTGCCGTG GAGCACGGAT ACAGAAACTG AGACACGTGG 1300
AGACTGGATG AGGGCAGATG AGGACAGGAA GAGAGTGTTA GAAAGGGTAG 1350
GACTGAGAAA CAGCCTATAA TCTCCAAAGA AAGAATAAGT CTCCAAGGAG 1400
CACAAAAAAA TCATATGTAC CAAGGATGTT ACAGTAAACA GGATGAACTA 1450
TTTAAACCCA CTGGGTCCTG CCACATCCTT CTCAAGGTGG TAGACTGAGT 1500
GGGGTCTCTC TGCCCAAGAT CCCTGACATA GCAGTAGCTT GTCTTTTCCA 1550
CATGATTTGT CTGTGAAAGA AAATAATTTT GAGATCGTTT TATCTATTTT 1600
CTCTACGGCT TAGGCTATGT GAGGGCAAAA CACAAATCCC TTTGCTAAAA 1650
AGAACCATAT TATTTTGATT CTCAAAGGAT AGGCCTTTGA GTGTTAGAGA 1700
AAGGAGTGAA GGAGGCAGGT GGGAAATGGT ATTTCTATTT TTAAATCCAG 1750
TGAAATTATC TTGAGTCTAC ACATTATTTT TAAAACACAA AAATTGTTCG 1800
GCTGGAACTG ACCCAGGCTG GACTTGCGGG GAGGAAACTC CAGGGCACTG 1850
CATCTGGCGA TCAGACTCTG AGCACTGCCC CTGCTCGCCT TGGTCATGTA 1900
CAGCACTGAA AGGAATGAAG CACCAGCAGG AGGTGGACAG AGTCTCTCAT 1950
GGATGCCGGC ACAAAACTGC CTTAAAATAT TCATAGTTAA TACAGGTATA 2000
TCTATTTTTA TTTACTTTGT AAGAAACAAG CTCAAGGAGC TTCCTTTTAA 2050
ATTTTGTCTG TAGGAAATGG TTGAAAACTG AAGGTAGATG GTGTTATAGT 2100
TAATAATAAA TGCTGTAAAT AAGCATCTCA CTTTGTAAAA ATAAAATATT 2150
GTGGTTTTGT TTTAAACATT CAACGTTTCT TTTCCTTCTA CAATAAACAC 2200
TTTCAAAATG TT 2212
```

FIG. 13B

| | | | | | | | | | | | | | | |
|---|---|---|---|---|---|---|---|---|---|---|---|---|---|---|
Met Leu Lys Lys Pro Leu Ser Ala Val Thr Trp Leu Cys Ile Phe
1           5                   10                  15

Ile Val Ala Phe Val Ser His Pro Ala Trp Leu Gln Lys Leu Ser
            20                  25                  30

Lys His Lys Thr Pro Ala Gln Pro Gln Leu Lys Ala Ala Asn Cys
            35                  40                  45

Cys Glu Glu Val Lys Glu Leu Lys Ala Gln Val Ala Asn Leu Ser
            50                  55                  60

Ser Leu Leu Ser Glu Leu Asn Lys Lys Gln Glu Arg Asp Trp Val
            65                  70                  75

Ser Val Val Met Gln Val Met Glu Leu Glu Ser Asn Ser Lys Arg
            80                  85                  90

Met Glu Ser Arg Leu Thr Asp Ala Glu Ser Lys Tyr Ser Glu Met
            95                  100                 105

Asn Asn Gln Ile Asp Ile Met Gln Leu Gln Ala Ala Gln Thr Val
            110                 115                 120

Thr Gln Thr Ser Ala Asp Ala Ile Tyr Asp Cys Ser Ser Leu Tyr
            125                 130                 135

Gln Lys Asn Tyr Arg Ile Ser Gly Val Tyr Lys Leu Pro Pro Asp
            140                 145                 150

Asp Phe Leu Gly Ser Pro Glu Leu Glu Val Phe Cys Asp Met Glu
            155                 160                 165

Thr Ser Gly Gly Gly Trp Thr Ile Ile Gln Arg Arg Lys Ser Gly
            170                 175                 180

Leu Val Ser Phe Tyr Arg Asp Trp Lys Gln Tyr Lys Gln Gly Phe
            185                 190                 195

Gly Ser Ile Arg Gly Asp Phe Trp Leu Gly Asn Glu His Ile His
            200                 205                 210

Arg Leu Ser Arg Gln Pro Thr Arg Leu Arg Val Glu Met Glu Asp
            215                 220                 225

Trp Glu Gly Asn Leu Arg Tyr Ala Glu Tyr Ser His Phe Val Leu
            230                 235                 240

FIG. 14A

Gly Asn Glu Leu Asn Ser Tyr Arg Leu Phe Leu Gly Asn Tyr Thr
                245             250             255

Gly Asn Val Gly Asn Asp Ala Leu Gln Tyr His Asn Asn Thr Ala
                260             265             270

Phe Ser Thr Lys Asp Lys Asp Asn Asp Asn Cys Leu Asp Lys Cys
                275             280             285

Ala Gln Leu Arg Lys Gly Gly Tyr Trp Tyr Asn Cys Cys Thr Asp
                290             295             300

Ser Asn Leu Asn Gly Val Tyr Tyr Arg Leu Gly Glu His Asn Lys
                305             310             315

His Leu Asp Gly Ile Thr Trp Tyr Gly Trp His Gly Ser Thr Tyr
                320             325             330

Ser Leu Lys Arg Val Glu Met Lys Ile Arg Pro Glu Asp Phe Lys
                335             340             345

Pro
346

FIG. 14B

| | | | | | | | | | | | |
|---|---|---|---|---|---|---|---|---|---|---|---|
| Glu | Glu | Lys | Asp | Gln | Leu | Gln | Val | Leu | Val | Ser | Lys | Gln | Asn | Ser |
| 211 | | | | 215 | | | | | 220 | | | | | 225 |

Glu Glu Lys Asp Gln Leu Gln Val Leu Val Ser Lys Gln Asn Ser
211               215               220               225

Ile Ile Glu Glu Leu Glu Lys Lys Ile Val Thr Ala Thr Val Asn
             230               235               240

Asn Ser Val Leu Gln Lys Gln Gln His Asp Leu Met Glu Thr Val
             245               250               255

Asn Asn Leu Leu Thr Met Met Ser Thr Ser Asn Ser Ala Lys Asp
             260               265               270

Pro Thr Val Ala Lys Glu Glu Gln Ile Ser Phe Arg Asp Cys Ala
             275               280               285

Glu Val Phe Lys Ser Gly His Thr Thr Asn Gly Ile Tyr Thr Leu
             290               295               300

Thr Phe Pro Asn Ser Thr Glu Glu Ile Lys Ala Tyr Cys Asp Met
             305               310               315

Glu Ala Gly Gly Gly Gly Trp Thr Ile Ile Gln Arg Arg Glu Asp
             320               325               330

Gly Ser Val Asp Phe Gln Arg Thr Trp Lys Glu Tyr Lys Val Gly
             335               340               345

Phe Gly Asn Pro Ser Gly Glu Tyr Trp Leu Gly Asn Glu Phe Val
             350               355               360

Ser Gln Leu Thr Asn Gln Gln Arg Tyr Val Leu Lys Ile His Leu
             365               370               375

Lys Asp Trp Glu Gly Asn Glu Ala Tyr Ser Leu Tyr Glu His Phe
             380               385               390

Tyr Leu Ser Ser Glu Glu Leu Asn Tyr Arg Ile His Leu Lys Gly
             395               400               405

Leu Thr Gly Thr Ala Gly Lys Ile Ser Ser Ile Ser Gln Pro Gly
             410               415               420

Asn Asp Phe Ser Thr Lys Asp Gly Asp Asn Asp Lys Cys Ile Cys
             425               430               435

Lys Cys Ser Gln Met Leu Thr Gly Gly Trp Trp Phe Asp Ala Cys
             440               445               450

Gly Pro Ser Asn Leu Asn Gly Met Tyr Tyr Pro Gln Arg Gln Asn
             455               460               465

Thr Asn Lys Phe Asn Gly Ile Lys Trp Tyr Tyr Trp Lys Gly Ser
             470               475               480

Gly Tyr Ser Leu Lys Ala Thr Thr Met Met Ile Arg Pro Ala Asp
             485               490               495

Phe
496

FIG. 15

Asp Cys Ala Asp Val Tyr Gln Ala Gly Phe Asn Lys Ser Gly Ile
285             290                 295

Tyr Thr Ile Tyr Ile Asn Asn Met Pro Glu Pro Lys Lys Val Phe
300             305                 310

Cys Asn Met Asp Val Asn Gly Gly Gly Trp Thr Val Ile Gln His
315             320                 325

Arg Glu Asp Gly Ser Leu Asp Phe Gln Arg Gly Trp Lys Glu Tyr
330             335                 340

Lys Met Gly Phe Gly Asn Pro Ser Gly Glu Tyr Trp Leu Gly Asn
345             350                 355

Glu Phe Ile Phe Ala Ile Thr Ser Gln Arg Gln Tyr Met Leu Arg
360             365                 370

Ile Glu Leu Met Asp Trp Glu Gly Asn Arg Ala Tyr Ser Gln Tyr
375             380                 385

Asp Arg Phe His Ile Gly Asn Glu Lys Gln Asn Tyr Arg Leu Tyr
390             395                 400

Leu Lys Gly His Thr Gly Thr Ala Gly Lys Gln Ser Ser Leu Ile
405             410                 415

Leu His Gly Ala Asp Phe Ser Thr Lys Asp Ala Asp Asn Asp Asn
420             425                 430

Cys Met Cys Lys Cys Ala Leu Met Leu Thr Gly Gly Trp Trp Phe
435             440                 445

Asp Ala Cys Gly Pro Ser Asn Leu Asn Gly Met Phe Tyr Thr Ala
450             455                 460

Gly Gln Asn His Gly Lys Leu Asn Gly Ile Lys Trp His Tyr Phe
465             470                 475

Lys Gly Pro Ser Tyr Ser Leu Arg Ser Thr Thr Met Met Ile Arg
480             485                 490

Pro Leu Asp Phe
495        498

FIG. 16

NL4 TIE LIGAND HOMOLOGUE

The present application was filed under 35 U.S.C. 371 of application Ser. No. PCT/US98/19093 filed on Sep. 14, 1998, which is a continuation-in-part of and claims benefit of the priority of applications of Ser. No. 08/933,821 filed on Sep. 19, 1997, now U.S. Pat. No. 5,972,338, which is a continuation-in-part Ser. No. 08/960,507 filed on Oct. 29, 1997, now U.S. Pat. No. 6,057,435.

FIELD OF THE INVENTION

The present invention concerns isolated nucleic acid molecules encoding novel TIE ligand homologues, the TIE ligand homologue proteins encoded by such nucleic acid molecules, as well as methods and means for making and using such nucleic acid and protein molecules, and antibodies binding the disclosed TIE ligand homologues.

BACKGROUND ART

The abbreviations "TIE" or "tie" are acronyms, which stand for "tyrosine kinase containing Ig and EGF homology domains" and were coined to designate a new family of receptor tyrosine kinases which are almost exclusively expressed in vascular endothelial cells and early hemopoietic cells, and are characterized by the presence of an EGF-like domain, and extracellular folding units stabilized by intra-chain disulfide bonds, generally referred to as "immunoglobulin (IG)-like" folds. A tyrosine kinase homologous cDNA fragment from human leukemia cells (tie) was described by Partanen et al., *Proc. Natl. Acad. Sci. USA* 87, 8913–8917 (1990). The mRNA of this human "tie" receptor has been detected in all human fetal and mouse embryonic tissues, and has been reported to be localized in the cardiac and vascular endothelial cells. Korhonen et al., *Blood* 80, 2548–2555 (1992); PCT Application Publication No. WO 93/14124 (published Jul. 22, 1993). The rat homolog of human tie, referred to as "tie-1", was identified by Maisonpierre et al., *Oncogene* 8, 1631–1637 (1993)). Another tie receptor, designated "tie-2" was originally identified in rats (Dumont et al., Oncogene 8, 1293–1301 (1993)), while the human homolog of tie-2, referred to as "ork" was descnbedin U.S. Pat. No. 5,447,860 (Ziegler). The murine homolog of tie-2 was originally termed "tek." The cloning of a mouse tie-2 receptor from a brain capillary cDNA library is disclosed in PCT Application Publication No. WO 95/13387 (published May 18, 1995). The TIE receptors are believed to be actively involved in angiogenesis, and may play a role in hemopoiesis as well.

The expression cloning of human TIE-2 ligands has been described in PCT Application Publication No. WO 96/11269 (published Apr. 18, 1996) and in U.S. Pat. No. 5,521,073 (published May 28, 1996). A vector designated as λgt10 encoding a TIE-2 ligand named "htie-2 ligand 1" or "hTL1" has been deposited under ATCC Accession No. 75928. A plasmid encoding another TIE-2 ligand designated "htie-2 2" or "hTL2" is available under ATCC Accession No. 75928. This second ligand has been described as an antagonist of the TAI-2 receptor. The identification of secreted human and mouse ligands for the TIE-2 receptor has been reported by Davis et al., *Cell* 87, 1161–1169 (1996). The human ligand designed "Angiopoietin-1", to reflect its role in angiogenesis and potential action during hemopoiesis, is the same ligand as the ligand variously designated as "htie-2 1" or "hTL-1" in WO 96/11269. Angiopoietin-1 has been described to play an angiogenic role later and distinct from that of VEGF (Suri et al., *Cell* 87, 1171–1180 (1996)). Since TIE-2 is apparently upregulated during the pathologic angiogenesis requisite for tumor growth (Kaipainen et al., *Cancer Res.* 54, 6571–6577 (1994)) angiopoietin-1 has been suggested to be additionally useful for specifically targeting tumor vasculature (Davis et al., supra).

SUMMARY OF THE INVENTION

The present invention concerns novel human TIE ligand homologues with powerful effects on vasculature. The invention also provides for isolated nucleic acid molecules encoding such ligand homologues or functional derivatives thereof, and vectors containing such nucleic acid molecules. The invention further concerns host cells transformed with such nucleic acid to produce the novel TIE ligand homologues or functional derivatives thereof. The novel TIE ligand homologues may be agonists or antagonists of TIE receptors, known or hereinafter discovered. Their therapeutic or diagnostic use, including the delivery of other therapeutic or diagnostic agents to cells expressing the respective TIE receptors, is also within the scope of the present invention.

The present invention further provides for agonist or antagonist antibodies specifically binding the TIE ligand homologues herein, and the diagnostic or therapeutic use of such antibodies.

In another aspect, the invention concerns compositions comprising the novel TIE ligand homologues or antibodies specifically binding such TIE ligand homologues.

In a further aspect, the invention concerns conjugates of the novel TIE ligand homologues of the present invention with other therapeutic or cytotoxic agents, and compositions comprising such conjugates. Because the TIE-2 receptor has been reported to be upregulated during the pathologic angiogenesis that is requisite for tumor growth, the conjugates of TIE ligand homologues of the present invention to cytotoxic or other anti-tumor agents may find utility in specifically targeting tumor vasculature.

In addition, it has been found that the gene encoding at least one TIE ligand homologue herein (NL8) is amplified in certain tumor cells. Accordingly, compositions and methods for the diagnosis and treatment of tumors are also within the scope of the invention.

In yet another aspect, the invention concerns a method for identifying a cell that expresses a TIE receptor, which comprises contacting a cell with a detectably labeled TIE ligand homologue of the present invention under conditions permitting the binding of such TIE ligand homologue to the TIE receptor, and determining whether such binding has indeed occurred.

In a different aspect, the invention concerns a method for measuring the amount of a TIE ligand homologue of the present invention in a biological sample by contacting the biological sample with at least one antibody specifically binding the TIE ligand homologue, and measuring the amount of the TIE ligand homologue-antibody complex formed.

In yet another embodiment, the invention concerns a method for the inhibition of endothelial cell proliferation comprising treating endothelial cells with an effective amount of a TIE ligand homologue herein.

In a still further embodiment, the invention concerns a method for the induction of endothelial cell apoptosis comprising treating endothelial cells with an effective amount of a TIE ligand homologue herein.

In another embodiment, the invention concerns a method for determining the presence of a TIE ligand homologue by exposing a cell suspected of containing such homologue to an anti-TIE ligand homologue antibody and determining the binding of the antibody to the cell.

The invention specifically concerns a method of diagnosing tumor is a mammal, comprising detecting the level of expression of a gene encoding a TIE ligand homologue herein (a) in a test sample of tissue cells obtained from the mammal, and (b) in a control sample of known normal tissue cells of the same cell type, wherein a higher expression level in the test sample indicates the presence of tumor in the mammal from which the test tissue cells were obtained. In a specific embodiment, the invention concerns a method of diagnosing tumor in a mammal by (a) contacting an anti-TIE ligand homologue antibody with a test sample of tissue cells obtained from the mammal, and (b) detecting the formation of a complex between the anti-TIE ligand homologue antibody and the TIE ligand homologue in the test sample.

The invention further concerns a method for inhibiting tumor cell growth comprising exposing a cell which overexpresses an NL8 polypeptide to an effective amount of an agent inhibiting the expression and/or activity of the NL8 polypeptide.

In a further embodiment, the invention concerns an article of manufacture, comprising: (a) a container; (b) a label on the container; and (c) a composition comprising an active agent contained within the container; wherein the composition is effective for inhibiting the growth of tumor cells, the label on the container indicates that the composition can be used for treating conditions characterized by overexpression of an NL8 polypeptide, and the active agent in the composition is an agent inhibiting the expression and/or activity of the NL8 polypeptide.

The invention further concerns a screening method for identifying polypeptide or small molecule agonists or antagonists of a TIE receptor based upon their ability to compete with a native or variant TIE ligand homologue of the present invention for binding to a corresponding TIE receptor.

The invention also concerns a method for imaging the presence of angiogenesis in wound healing, in inflammation or in tumors of human patients, which comprises administering detectably labeled TIE ligand homologues or agonist antibodies of the present invention, and detecting angiogenesis.

In another aspect, the invention concerns a method of promoting or inhibiting neovascularization in a patient by administering an effective amount of a TIE ligand homologue of the present invention in a pharmaceutically acceptable vehicle. In a preferred embodiment, the present invention concerns a method for the promotion of wound healing. In another embodiment, the invention concerns a method for promoting angiogenic processes, such as for inducing collateral vascularization in an ischemic heart or limb. In a further preferred embodiment, the invention concerns a method for inhibiting tumor growth.

In yet another aspect, the invention concerns a method of promoting bone development and/or maturation and/or growth in a patient, comprising administering to the patient an effective amount of a TIE ligand homologue of the present invention in a pharmaceutically acceptable vehicle.

In a further aspect, the invention concerns a method of promoting muscle growth and development, which comprises administering a patient in need an effective amount of a TIE ligand homologue of the present invention in a pharmaceutically acceptable vehicle.

The TIE ligand homologues of the present invention may be administered alone, or in combination with each other and/or with other therapeutic or diagnostic agents, including members of the VEGF family. Combination therapies may lead to new approaches for promoting or inhibiting neovascularization, and muscle growth and development.

BRIEF DESCRIPTION OF THE FIGURES

FIGS. 1A-1 and 1A-2 are the nucleotide sequence of FLS139 (SEQ. ID. NO.: 16).

FIGS. 1B-1 and 1B-2 are the nucleotide sequence of FLS139 (SEQ. ID. NO.: 17).

FIGS. 2A and 2B are the nucleotide sequence of the TIE ligand NL1 (SEQ. ID. NO.: 1) (DNA 22779).

FIGS. 3A and 3B are the amino acid sequence of the TIE ligand NL1 (SEQ. ID. NO.: 2).

FIGS. 4A–4C are the nucleotide sequence of the TIE ligand NL5 (SEQ. ID. NO.: 3) (DNA28497).

FIGS. 5A and 5B are the amino acid sequence of the TIE ligand NL5 (SEQ. ID. NO.: 4).

FIGS. 6A and 6B are the nucleotide sequence of the TIE ligand NL8 (SEQ. ID. NO.: 5) (DNA 23339).

FIGS. 7A and 7B are the amino acid sequence of the TIE ligand NL8 (SEQ. ID. NO.: 6).

FIGS. 13A and 13B are the nucleotide sequence of the TIE ligand NL4 (SEQ. ID NO: 18).

FIGS. 14A and 14B are the amino acid sequence of the TIE ligand NL4 (SEQ. ID NO: 19).

FIG. 15 is the amino acid sequence of human TIE-2 ligand 2 derived from pBluescript KS clone (SEQ. ID. NO.: 20).

FIG. 16 is the amino acid sequence of human TIE-2 ligand 1 derived from a lambda-gt10 clone (SEQ. ID. NO.: 21).

DETAILED DESCRIPTION OF THE INVENTION

Figure 8A:
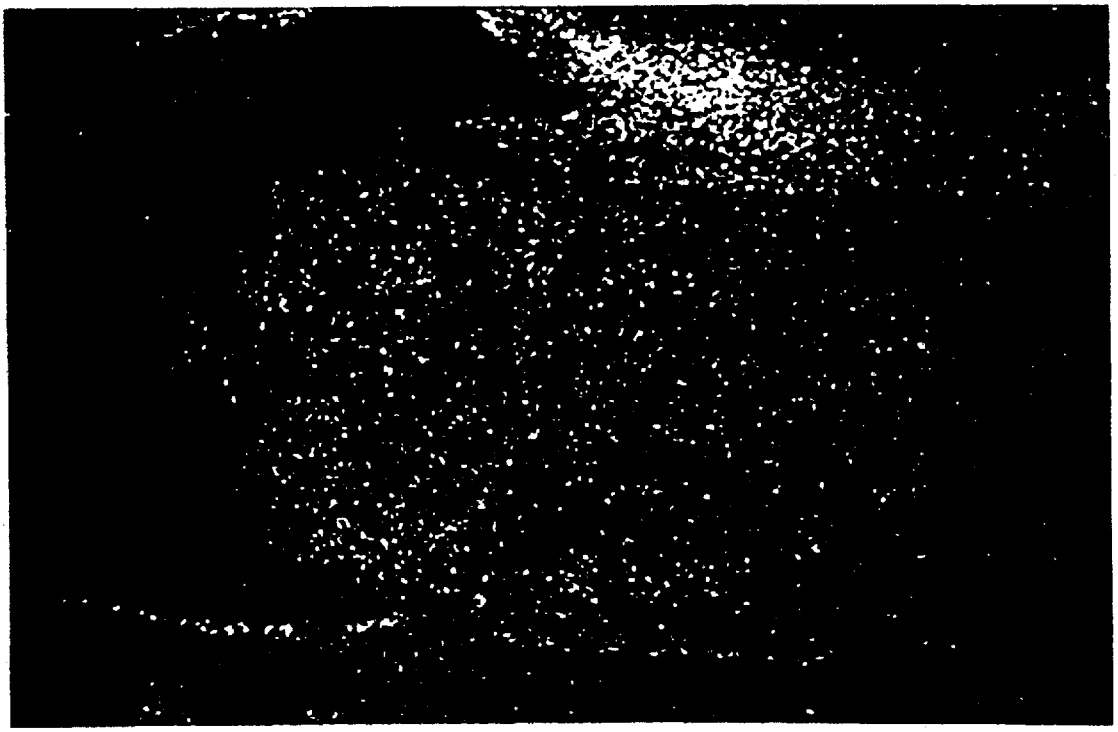
FIGS. 8-A and 8-B show the expression of NL1 in various tissues as determined by in situ hybridization to cellular RNA.

A. TIE Ligand Homologues and Nucleic Acid Molecules Encoding Them

The TIE ligand homologues of the present invention include the native human proteins designated NL1 (SEQ. ID. NO: 2), NL5 (SEQ. ID. NO: 4), NL8 (SEQ. ID. NO: 6), and NL4 (SEQ. ID. NO: 19), and their homologues in other, non-human mammalian species, including, but not limited to, higher mammals, such as monkey; rodents, such as mice, rats, hamster; porcine; equine; bovine; naturally occurring allelic and splice variants, and biologically active (functional) derivatives, such as, amino acid sequence variants of such native molecules, as long as they differ from a native TL-1 or TL-2 ligand. For example, the amino acid sequence of NL4 is about 34% identical with hTL2 and about 32% identical with hTL1. The native TIE ligand homologues of the present invention are substantially free of other proteins with which they are associated in their native environment. This definition is not limited in any way by the method(s) by which the TIE ligand homologues of the present invention are obtained, and includes all TIE ligand homologues otherwise within the definition, whether purified from natural source, obtained by recombinant DNA technology, synthesized, or prepared by any combination of these and/or other techniques. The amino acid sequence variants of the native TIE ligand homologues of the present invention shall have at least about 90%, preferably, at least about 95%, more preferably at least about 98%, most preferably at least about 99% sequence identity with a full-length, native human TIE ligand homologue of the present invention, or with the fibrinogen-like domain of a native human TIE ligand homologue of the present invention. Such amino acid sequence variants preferably exhibit or inhibit a qualitative biological activity of a native TIE ligand homologue.

The term "fibrinogen domain" or "fibrinogen-likedomain" is used to refer to amino acids from about position 278 to about position 498 in the known hTL-1 amino acid sequence; amino acids from about position 276 to about position 496 in the known hTL-2 amino acid sequence; amino acids from about position 270 to about 493 in the amino acid sequence of NL1; amino acids from about position 272 to about position 491 in the amino acid sequence of NL5; amino acids from about position 252 to about position 470 in the amino acid sequence of NL8; amino acids from about position 130 to about position 346 in the amino acid sequence of NL4; and to homologous domains in other TIE ligand homologues. The amino acid sequence identity between the fibrinogen domain of NL4 and those of hTL-1 and hTL-2 is about 44%.

The term "nucleic acid molecule" includes RNA, DNA and cDNA molecules. It will be understood that, as a result of the degeneracy of the genetic code, a multitude of nucleotide sequences encoding a given TIE ligand homologue may be produced. The present invention specifically contemplates every possible variation of nucleotide sequences, encoding the TIE ligand homologues of the present invention, based upon all possible codon choices. Although nucleic acid molecules which encode the TIE ligand homologues herein are preferably capable of hybridizing, under stringent conditions, to a naturally occurring TIE ligand homologue gene, it may be advantageous to produce nucleotide sequences encoding TIE ligand homologues, which possess a substantially different codon usage. For example, codons may be selected to increase the rate at which expression of the polypeptide occurs in a particular prokaryotic or eukaryotic host cells, in accordance with the frequency with which a particular codon is utilized by the host. In addition, RNA transcripts with improved properties, e.g. half-life can be produced by proper choice of the nucleotide sequences encoding a given TIE ligand homologue.

"Sequence identity" shall be determined by aligning the two sequences to be compared following the Clustal method of multiple sequence alignment (Higgins et al., *Comput. Appl. Biosci.* 5, 151–153 (1989), and Higgins et al., *Gene* 73, 237–244 (1988)) that is incorporated in version 1.6 of the Lasergene biocomputing software (DNASTAR, Inc., Madison, Wis.), or any updated version or equivalent of this software.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 $\mu$g/ml), 0.1% SDS, and 10% dextran sulfate at 42° C., with washes at 42° c. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and %SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/mL denatured sheared salmon sperm DNA, followed by washing the filters in 1×SSC at about 37–50° C. The skilled artisan will recognize how to adjust the temperature, ionic strength, etc. as necessary to accommodate factors such as probe length and the like.

The term "epitope tagged" when used herein refers to a chimeric polypeptide comprising a TIE ligand homologue polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

The terms "biological activity" and "biologically active" with regard to a TIE ligand homologue of the present invention refer to the ability of a molecule to specifically bind to and signal through a native receptor of a TIE ligand, known or hereinafter discovered, (hereinafter referred to as a "TIE receptor"), e.g. a native TIE-2 receptor, or to block the ability of a native TIE receptor (e.g. TIE-2) to participate in signal transduction. Thus, the (native and variant) TIE ligands of the present invention include agonists and antagonists of a native TIE, e.g. TIE-2, receptor. Preferred biological activities of the TIE ligands of the present invention include the ability to induce or inhibit vascularization. The ability to induce vascularization will be useful for the treatment of biological conditions and diseases, where vascularization is desirable, such as wound healing, ischaemia, and diabetes. On the other hand, the ability to inhibit or block vascularization may, for example, be useful in preventing or attenuating tumor growth. Another preferred biological activity is the ability to affect muscle growth or development. A further preferred biological activity is the ability to influence bone development, maturation, or growth. Yet another preferred biological activity is involvement in the pathogenesis of cancer, such as breast cancer. Still further preferred biological activity is the ability to inhibit endothelial cell growth and/or induce apoptosis.

The term "native TIE receptor" is used herein to refer to a TIE receptor of any animal species, including, but not limited to, humans, other higher primates, e.g. monkeys, and rodents, e.g. rats and mice. The definition specifically includes, but is not limited to, the TIE-2 receptor, disclosed, for example, in PCT Application Serial No. WO 95/13387 (published May 18, 1995), and the endothelial cell receptor tyrosine kinase termed "TIE" in PCT Application Publication No. WO 93/14124 (published Jul. 22, 1993), and preferably is TIE-2.

The term "functional derivative" is used to define biologically active amino acid sequence variants of the native TIE ligand homologues of the present invention, as well as covalent modifications, including derivatives obtained by reaction with organic derivatizing agents, post-translational modifications, derivatives with nonproteinaceous polymers, and immunoadhesins.

"Vascular endothelial growth factor"/"vascular permeability factor" (VEGF/VPF) is an endothelial cell-specific mitogen which has recently been shown to be stimulated by hypoxia and required for tumor angiogenesis (Senger et al., *Cancer* 46: 5629–5632 (1986); Kim et al., *Nature* 362:841–844 (1993); Schweiki et al., *Nature* 359: 843–845 (1992); Plate et al., *Nature* 359: 845–848 (1992)). It is a 34–43 kDa (with the predominant species at about 45 kDa) dimeric, disulfide-linked glycoprotein synthesized and secreted by a variety of tumor and normal cells. In addition, cultured human retinal cells such as pigment epithelial cells and pericytes have been demonstrated to secrete VEGF and to increase VEGF gene expression in response to hypoxia (Adamis et al., *Biochem. Biophys. Res. Commun.* 193: 631–638 (1993); Plouet et al. *Invest. Ophthalmol. Vis. Sci.* 34: 900 (1992); Adamis et al., *Invest. Ophthalmol. Vis. Sci.* 34: 1440 (1993); Aiello et al., *Invest. Opthalmol. Vis. Sci.* 35: 1868 (1994); Simorre-pinatel et al., *Invest. Opthalmol. Vis. Sci.* 35: 3393–3400 (1994)). In contrast, VEGF in normal tissues is relatively low. Thus, VEGF appears to play a principle role in many pathological states and processes related to neovascularization. Regulation of VEGF expression in tissues affected by the various conditions described above could therefore be key in treatment or preventative therapies associated with hypoxia.

The term "isolated" when used to describe the various polypeptides described herein, means polypeptides that have been identified and separated and/or recovered from a component of its natural environment. Contaminant components of its natural environment are materials that would typically interfere with diagnostic or therapeutic uses for the polypeptide, and may include enzymes, hormones, and other proteinaceous or non-proteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the TIE ligand homologue's natural environment will not be present. Ordinarily, however, isolated polypeptide will be prepared by at least one purification step.

The term "agonist" is used to refer to peptide and non-peptide analogs of the native TIE ligand homologues of the present invention and to antibodies specifically binding such native TIE ligand homologues, provided that they have the ability to signal through a native TIE receptor (e.g. TIE-2). In other words, the term "agonist" is defined in the context of the biological role of the TIE receptor, and not in relation to the biological role of a native TIE ligand homologue, which, as noted before, may be an agonist or antagonist of the TIE receptor biological function. Preferred agonists are promoters of vasculzation or play a role in bone formation maturation or growth. Other preferred agonists promote muscle growth or development.

The term "antagonist" is used to refer to peptide and non-peptide analogs of the native TIE ligand homologues of the present invention and to antibodies specifically binding such native TIE ligand homologues, provided that they have the ability to inhibit the biological function of a native TIE receptor (e.g. TIE-2). Again, the term "antagonist" is defined in the context of the biological role of the TIE receptor, and not in relation to the biological activity of a native TIE ligand homologue, which may be either an agonist or an antagonist of the TIE receptor biological function. Preferred antagonists are inhibitors of vasculogenesis, or pathological bone or muscle development or growth.

The phrases "gene amplification" and "gene duplication" are used interchangeably and refer to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e. the level of gene expression, also increases in the proportion of the number of copies made of the particular gene expressed.

"Tumor", as used herein, refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colorectal cancer, endometrial carcinoma, salivary gland carcinoma, kidney cancer, liver cancer, vulval cancer, thyroid cancer, hepatic carcinoma and various types of head and neck cancer.

"Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. In tumor (e.g. cancer) treatment, a therapeutic agent may directly decrease the pathology of tumor cells, or render the tumor cells more susceptible to treatment by other therapeutic agents, e.g. radiation and/or chemotherapy.

The "pathology" of cancer includes all phenomena that compromise the well-being of the patient. This includes, without limitation, abnormal or uncontrollable cell growth, metassis, interference with the normal functioning of neighboring cells, release of cytokines or other secretory products at abnormal levels, suppression or aggravation of inflammatory or immunological response, etc.

"Mammal" for purposes of treatment refers to any animal classified as a mammal, including humans, domestic and farm animals, and zoo, sports, or pet animals, such as dogs, horses, cats, cows, etc. Preferably, the mammal is human.

Administration "in combination with" one or more further therapeutic agents includes simultaneous (concurrent) and consecutive administration in any order.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (Taxol, Bristol-Myers Squibb Oncology, Princeton, N.J.), and doxetaxel (Taxotere, Rhône-Poulenc Rorer, Antony, Rnace), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al. (W B Saunders: Philadelphia, 1995), especially p. 13.

"Doxorubicin" is an athracycline antibiotic. The full chemical name of doxorubicin is (8S-cis)-10-[(3-amino-2, 3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionylhuman growth hormone, and bovine growth hormone; parathyroidhormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor, fibroblast growth factor, prolactin; placental lactogen; tumor necrosis factor-α and -β; mullerian-inhibiting substance; mouse gonadotropin-associated peptide; inhibin; activin; vascular endothelial growth factor, integrin; thrombopoietin (TPO); nerve growth factors such as NGF-β; platelet-growth factor, transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL2, IL-3, IL-4, IL-5, IL-6, IL-7, IL-8, IL-9, IL-11, IL-12; a tumor necrosis factor such as TNF-α or TNFβ; and other polypeptide factors including LIF and kit ligand (KL). As used herein, the term cytokine includes proteins from natural sources or from recombinant cell culture and biologically active equivalents of the native sequence cytokines.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes nucleic acid molecules contained in cells that ordinarily express a TIE ligand homologue of the present invention, where, for example, the nucleic acid molecule is in a chromosomal location different from that of natural cells.

The term "amino acid sequence variant" refers to molecules with some differences in their amino acid sequences as compared to a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Insertional variants are those with one or more amino acids inserted immediately adjacent to an amino acid at a particular position in a native sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule. Deletional variants include those having C- and/or N-terminal deletions (truncations) as well as variants with internal deletions of one or more amino acids. The preferred deletional variants of the present invention contain deletions outside the fibrinogen-likedomain of a native TIE ligand homologue of the present invention.

The amino acid sequence variants of the present invention may contain various combinations of amino acid substitutions, insertions and/or deletions, to produce molecules with optimal characteristics.

The amino acids may be classified according to the chemical composition and properties of their side chains. They are broadly classified into two groups, charged and uncharged. Each of these groups is divided into subgroups to classify the amino acids more accurately.

I. Charged Amino Acids

Acidic Residues: aspartic acid, glutamic acid

Basic Residues: lysine, arginine, histidine

II. Uncharged Amino Acids

Hydrophilic Residues: serine, threonine, asparagine, glutamine

Aliphatic Residues: glycine, alanine, valine, leucine, isoleucine

Non-polar Residues: cysteine, methionine, proline

Aromatic Residues: phenylalanine, tyrosine, tryptophan

Conservative substitutions involve exchanging a member within one group for another member within the same group, whereas non-conservative substitutions will entail exchanging a member of one of these classes for another. Variants obtained by non-conservative substitutions are expected to result in significant changes in the biological properties/function of the obtained variant Amino acid sequence deletions generally range from about 1 to 30 residues, more preferably about 1 to 10 residues, and typically are contiguous. Deletions may be introduced into regions not directly involved in the interaction with a native TIE receptor. Deletions are preferably performed outside the fibrinogen-like regions at the C-terminus of the TIE ligand homologues of the present invention.

Amino acid insertions include amino- and/or carboxyl-terminal fusions ranging in length from one residue to polypeptides containing a hundred or more residues, as well as intrasequence insertions of single or multiple amino acid residues. Intrasequence insertions (i.e. insertions within the TIE ligand homologue amino acid sequence) may range generally from about 1 to 10 residues, more preferably 1 to 5 residues, more preferably 1 to 3 residues. Examples of terminal insertions include the TIE ligand homologues with an N-terminal methionyl residue, an artifact of its direct expression in bacterial recombinant cell culture, and fusion of a heterologous N-terminal signal sequence to the N-terminus of the TIE ligand homologue molecule to facilitate the secretion of the mature TIE ligand homologue from recombinant host cells. Such signal sequences will generally be obtained from, and thus homologous to, the intended host cell species. Suitable sequences include, for example, STII or Ipp for *E. coli*, alpha factor for yeast, and viral signals such as herpes gD for mammalian cells. Other insertional variants of the native TIE ligand homologue molecules include the fusion of the N- or C-terminus of the TIE ligand homologue molecule to immunogenic polypeptides, e.g. bacterial polypeptides such as beta-lactamase or an enzyme encoded by the *E. coli* trp locus, or yeast protein, and C-terminal fusions with proteins having a long half-life such as immunoglobulin regions (preferably immunoglobulin constant regions), albumin, or ferritin, as described in WO 89/02922 published on Apr. 6, 1989.

Since it is often difficult to predict in advance the characteristics of a variant TIE ligand homologue, it will be appreciated that some screening will be needed to select the optimum variant.

Amino acid sequence variants of native TIE ligand homologues of the present invention are prepared by methods known in the art by introducing appropriate nucleotide changes into a native or variant TIE ligand homologue DNA, or by in vitro synthesis of the desired polypeptide. There are two principal variables in the construction of amino acid sequence variants: the location of the mutation site and the nature of the mutation. With the exception of naturally-occurring alleles, which do not require the manipulation of the DNA sequence encoding the TIE ligand homologue, the amino acid sequence variants of the TIE ligand homologues are preferably constructed by mutating the DNA, either to arrive at an allele or an amino acid sequence variant that does not occur in nature.

One group of the mutations will be created within the domain or domains of the TIE ligand homologues of the present invention identified as being involved in the interaction with a TIE receptor, e.g. TIE-1 or TIE-2.

Alternatively or in addition, amino acid alterations can be made at sites that differ in TIE ligand homologues from various species, or in highly conserved regions, depending on the goal to be achieved.

Sites at such locations will typically be modified in series, e.g. by (1) substituting first with conservative choices and then with more radical selections depending upon the results achieved, (2) deleting the target residue or residues, or (3) inserting residues of the same or different class adjacent to the located site, or combinations of options 1–3.

One helpful technique is called "alanine scanning" (Cunningham and Wells, *Science* 244, 1081–1085 [1989]). Here, a residue or group of target residues is identified and substituted by alanine or polyalanine. Those domains demonstrating functional sensitivity to the alanine substitutions are then refined by introducing further or other substituents at or for the sites of alanine substitution.

After identifying the desired mutation(s), the gene encoding an amino acid sequence variant of a TIE ligand can, for example, be obtained by chemical synthesis as hereinabove described.

More preferably, DNA encoding a TIE ligand homologue amino acid sequence variant is prepared by site-directed mutagenesis of DNA that encodes an earlier prepared variant or a nonvariant version of the ligand. Site-directed (site-specific) mutagenesis allows the production of ligand variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the techniques of site-specific mutagenesis are well known in the art, as exemplified by publications such as, Edelman et al., *DNA* 2, 183 (1983). As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and*

*Recombinant DNA*, A. Walton, ed., Elsevier, Amsterdam (1981). This and other phage vectors are commercially available and their use is well known to those skilled in the art. A versatile and efficient procedure for the construction of oligodeoxyribonucleotide directed site-specific mutations in DNA fragments using M13-derived vectors was published by Zoller, M. J. and Smith, M., *Nucleic Acids Res.* 10, 6487–6500 [1982]). Also, plasmid vectors that contain a single-stranded phage origin of replication (Veira et al., *Meth. Enzymol.* 153, 3 [1987]) may be employed to obtain single-stranded DNA. Alternatively, nucleotide substitutions are introduced by synthesizing the appropriate DNA fragment in vitro, and amplifying it by PCR procedures known in the art.

In general, site-specific mutagenesis herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci. USA* 75, 5765 (1978). This primer is then annealed with the single-stranded protein sequence-containing vector, and subjected to DNA-polymerizing enzymes such as, *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate host cells such as JP101 cells, and clones are selected that include recombinant vectors bearing the mutated sequence arrangement. Thereafter, the mutated region may be removed and placed in an appropriate expression vector for protein production.

The PCR technique may also be used in creating amino acid sequence variants of a TIE ligand homologue. When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer or performing a second PCR with different mutant primers and ligating the two resulting PCR fragments simultaneously to the vector fragment in a three (or more) part ligation.

In a specific example of PCR mutagenesis, template plasmid DNA (1 μg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp$^R$ kits (obtained from Perkin-Elmer Cetus, Norwalk, Conn. and Emeryville, Calif.), and 25 pmole of each oligonucleotide primer, to a final volume of 50 μl. The reaction mixture is overlayered with 35 μl mineral oil. The reaction is denatured for 5 minutes at 100 °C., placed briefly on ice, and then 1 μl *Thermus aquaticus* (Taq) DNA polymerase (5 units/1), purchased from Perkin-Elmer Cetus, Norwalk, Conn. and Emeryville, Calif.) is added below the mineral oil layer. The reaction mixture is then inserted into a DNA Thermal Cycler (purchased from Perkin-Elmer Cetus) programmed as follows:

2 min. 55° C., 30 sec. 72° C., then 19 cycles of the following:

30 sec. 94° C., 30 sec. 55° C., and 30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to appropriate treatments for insertion into a vector.

Another method for preparing variants, cassette mutagenesis, is based on the technique described by Wells et al. [*Gene* 34, 315 (1985)]. The starting material is the plasmid (or vector) comprising the TIE ligand homologue DNA to be mutated. The codon(s) within the TIE ligand homologue to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the DNA encoding the TIE ligand homologue. After the restriction sites have been introduced into the plasmid, the plasmid is cut at these sites to linearize it. A double-stranded oligonucleotide encoding the sequence of the DNA between the restriction site but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated TIE ligand homologue DNA sequence.

Additionally, the so-called phagemid display method may be useful in making amino acid sequence variants of native or variant TIE ligand homologues. This method involves (a) constructing a replicable expression vector comprising a first gene encoding an receptor to be mutated, a second gene encoding at least a portion of a natural or wild-type phage coat protein wherein the first and second genes are heterologous, and a transcription regulatory element operably linked to the first and second genes, thereby forming a gene fusion encoding a fusion protein; (b) mutating the vector at one or more selected positions within the first gene thereby forming a family of related plasmids; (c) transforming suitable host cells with the plasmids; (d) infecting the transformed host cells with a helper phage having a gene encoding the phage coat protein; (e) culturing the transformed infected host cells under conditions suitable for forming recombinant phagemid particles containing at least a portion of the plasmid and capable of transforming the host, the conditions adjusted so that no more than a minor amount of phagemid particles display more than one copy of the fusion protein on the surface of the particle; (f) contacting the phagemid particles with a suitable antigen so that at least a portion of the phagemid particles bind to the antigen; and (g) separating the phagemid particles that bind from those that do not Steps (d) through (g) can be repeated one or more times. Preferably in this method the plasmid is under tight control of the transcription regulatory element, and the culturing conditions are adjusted so that the amount or number of phagemid particles displaying more than one copy of the fusion protein on the surface of the particle is less than about 1%. Also, preferably, the amount of phagemid particles displaying more than one copy of the fusion protein is less than 10% of the amount of phagemid particles displaying a single copy of the fusion protein. Most preferably, the amount is less than 20%. Typically in this method, the expression vector will further contain a secretory signal sequence fused to the DNA encoding each subunit of the polypeptide and the transcription regulatory element will be a promoter system. Preferred promoter systems are selected from lac Z, $\lambda_{PL}$, tac, T7 polymerase, tryptophan, and alkaline phosphatase promoters and combinations thereof. Also, normally the method will employ a helper phage selected from M13K07, M13R408, M13-VCS, and Phi X 174. The preferred helper phage is M13K07, and the preferred coat protein is the M13 Phage gene III coat protein. The preferred host is *E. coli*, and protease-deficient strains of *E. coli*.

Further details of the foregoing and similar mutagenesis techniques are found in general textbooks, such as, for example, Sambrook et al., *Molecular Cloning: A laboratory Manual* (New York: Cold Spring Harbor Laboratory Press, 1989), and *Current Protocols in Molecular Biology*, Ausubel et al., eds., Wiley-Interscience, 1991.

"Immunoadhesins" are chimeras which are traditionally constructed from a receptor sequence linked to an appropriate immunoglobulin constant domain sequence (immunoadhesins). Such structures are well known in the art. Immunoadhesins reported in the literature include fusions of the T cell receptor * [Gascoigne et al., *Proc. Natl. Acad. Sci. USA* 84, 2936–2940 (1987)]; CD4 * [Capon et al., *Nature* 337, 525–531 (1989); Traunecker et al., *Nature* 329, 68–70 (1989); Zettmeissl et al., *DNA Cell Biol. USA* 9, 347–353 (1990); Byrn et al., *Nature* 344, 667–670 (1990)]; L-selectin (homing receptor) [Watson et al., *J. Cell. Biol.* 110, 2221–2229 (1990); Watson et al., *Nature* 349, 164–167 (1991)]; CCD44* [Aruffo et al., *Cell* 61, 1303–1313 (1990)]; CD28* and B7* [Linsley et al., *J. Exp. Med.* 173, 721–730 (1991)]; CTLA-4* [Lisley et al., *J. Exp. Med.* 174, 561–569 (1991)]; CD22* [Stamenkovic et al., *Cell* 66, 1133–1144 (1991)]; TNF receptor [Ashkenazi et al., *Proc. Natl. Acad. Sci. USA* 88, 10535–10539 (1991); Lesslauer et al., *Eur. J. Immunol.* 27, 2883–2886 (1991); Peppel et al., *J. Exp. Med.* 174, 1483–1489 (1991)]; NP receptors [Bennett et al., *J. Biol. Chem.* 266, 23060–23067 (1991)]; IgE receptor α-chain* [Ridgway and Gorman, *J. Cell. Biol.* 115, abstr. 1448 (1991)]; HGF receptor [Mark, M. R. et al., 1992, *J. Biol. Chem.* submitted], where the asterisk (*) indicates that the receptor is member of the immunoglobulin superfamily.

Ligand-immunoglobulin chimeras are also known, and are disclosed, for example, in U.S. Pat. No. 5,304,640 (for L-selectin ligands); U.S. Pat. Nos. 5,316,921 and 5,328,837 (for HGF variants). These chimeras can be made in a similar way to the construction of receptor-immunoglobulin chimeras.

Covalent modifications of the TIE ligand homologues of the present invention are included within the scope herein. Such modifications are traditionally introduced by reacting targeted amino acid residues of the TIE ligand homologue with an organic derivatizing agent that is capable of reacting with selected sides or terminal residues, or by harnessing mechanisms of post-translational modifications that function in selected recombinant host cells. The resultant covalent derivatives are useful in programs directed at identifying residues important for biological activity, for immunoassays, or for the preparation of anti-TIE ligand homologue antibodies for immuno affinity purification of the recombinant. For example, complete inactivaton of the biological activity of the protein after reaction with ninhydrin would suggest that at least one arginyl or lysyl residue is critical for its activity, whereafter the individual residues which were modified under the conditions selected are identified by isolation of a peptide fragment containing the modified amino acid residue. Such modifications are within the ordinary skill in the art and are performed without undue experimentation.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Para-bromophenacylbromide also is useful; the reaction is preferably performed in 0.1M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}$I or $^{131}$I to prepare labeled proteins for use in radioimmunoassay.

Carboxyl side groups (aspartyl or glutamyl) are selectively modified by reaction with carbodiimides (R'—N=C=N—R') such as 1-cyclohexyl-3-(2-morpholinyl-4-ethyl) carbodiimide or 1-ethyl-3-(4azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl, threonyl or tyrosyl residues, methylation of the α-amino groups of lysine, arginine, and histidine side chains (T. E. Creighton, *Proteins: Structure and Molecular Properties* W. H. Freeman & Co., San Francisco, pp.79–86 [1983]), acetylation of the N-terminal amine, and amidation of any C-terminal carboxyl group. The molecules may further be covalently linked to nonproteinaceous polymers, e.g. polyethylene glycol, polypropylene glycol or polyoxyalkylenes, in the manner set forth in U.S. Ser. No. 07/275,296 or U.S. Pat. Nos. 4,640,835; 4,496,689; 4,301,144; 4,670,417; 4,791,192 or 4,179,337.

Derivatization with bifunctional agents is useful for preparing intramolecular aggregates of the TIE ligand with polypeptides as well as for cross-linking the TIE ligand polypeptide to a water insoluble support matrix or surface for use in assays or affinity purification. In addition, a study of interchain cross-links will provide direct information on conformational structure. Commonly used cross-linking agents include 1,1-bis(diazaceiyl-2-phenylethane, glutaraldehyde, N-hydroxysuccinimideesters, homobifunctionalimidoesters, and bifunctionalmaleimides. Derivatizing agents such as methyl-3-[(p-azidophenyl) dithio]propioimidat yield photoactivatable intermediates which are capable of forming cross-links in the presence of light. Alternatively, reactive water insoluble matrices such as cyanogen bromide activated carbohydrates and the systems reactive substrates described in U.S. Pat. Nos. 3,959,642; 3,969,287; 3,691,016; 4,195,128; 4,247,642; 4,229,537; 4,055,635; and 4,330,440 are employed for protein immobilization and cross-linking.

Certain post-translational modifications are the result of the action of recombinant host cells on the expressed polypeptide. Glutaminyl and aspariginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl, threonyl or tyrosyl residues, methylation of the α-amino groups of lysine, arginine, and histidine side chains [T. E. Creighton, *Proteins: Structure and Molecular Properties*, W. H. Freeman & Co., San Francisco, pp. 79–86 (1983)].

Other derivatives comprise the novel peptides of this invention covalently bonded to a nonproteinaceous polymer. The nonproteinaceous polymer ordinarily is a hydrophilic synthetic polymer, i.e. a polymer not otherwise found in nature. However, polymers which exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. Particularly useful are polyvinylalkylene ethers such a polyethylene glycol, polypropylene glycol.

The TIE ligand homologues may be linked to various nonproteinaceous polymers, such as polyethyleneglycol (PEG), polypropyleneglycol or polyoxyalkylenes, in the manner set forth in U.S. Pat. Nos. 4,640,835; 4,496,689; 4,301,144; 4,670,417; 4,791,192 or 4,179,337. These variants, just as the immunoadhesins of the present invention are expected to have longer half-lives than the corresponding native TIE ligands.

The TIE ligand homologues may be entrapped in microcapsules prepared, for example, by coacervation techniques or by interfacial polymerization, in colloidal drug delivery systems (e.g. liposomes, albumin microspheres, microemulsions, nano-particles and nanocapsules), or in macroemulsions. Such techniques are disclosed in *Remington's Pharmaceutical Sciences*, 16th Edition, Osol, A., Ed. (1980).

B. Anti-TIE Ligand Homologue Antibodies

The present invention covers agonist and antagonist antibodies, specifically binding the TIE ligand homologues. The antibodies may be monoclonal or polyclonal, and include, without limitation, mature antibodies, antibody fragments (e.g. Fab, $F(ab')_2$, $F_v$, etc.), single-chain antibodies and various chain combinations.

The term "antibody" is used in the broadest sense and specifically covers single monoclonal antibodies (including agonist, antagonist, and neutralizing antibodies) specifically binding a TIE ligand homologue of the present invention and antibody compositions with polyepitopic specificity.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen.

The monoclonal antibodies herein include hybrid and recombinant antibodies produced by splicing a variable (including hypervariable) domain of an anti-TIE ligand homologue antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g. Fab, $F(ab')_2$, and Fv), so long as they exhibit the desired biological activity. See, e.g. U.S. Pat. No. 4,816,567 and Mage et al., in *Monoclonal Antibody Production Techniques and Applications*, pp.79–97 (Marcel Dekker, Inc.: New York, 1987).

Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, *Nature*, 256:495 (1975), or may be made by recombinant DNA methods such as described in U.S. Pat. No. 4,816,567. The "monoclonal antibodies" may also be isolated from phage libraries generated using the techniques described in McCafferty et al., *Nature*, 348:552–554 (1990), for example.

"Humanized" forms of non-human (e.g. murine) antibodies are specific chimeric immunoglobulins, immunoglobulin chains, or fragments thereof (such as Fv, Fab, Fab', $F(ab')_2$ or other antigen-binding subsequences of antibodies) which contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues which are found neither in the recipient antibody nor in the imported CDR or framework sequences. These modifications are made to further refine and optimize antibody performance. In general the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin.

Polyclonal antibodies to a TIE ligand homologue of the present invention generally are raised in animals by multiple subcutaneous (sc) or intraperitoneal (ip) injections of the TIE ligand homologue and an adjuvant It may be useful to conjugate the TIE ligand homologue or a fragment containing the target amino acid sequence to a protein that is immunogenic in the species to be immunized, e.g. keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glytaraldehyde, succinic anhydride, $SOCl_2$, or $R^1N=C=NR$, where R and $R^1$ are different alkyl groups.

Animals are immunized against the immunogenic conjugates or derivatives by combining 1 mg or 1 $\mu$g of conjugate (for rabbits or mice, respectively) with 3 volumes of Freud's complete adjuvant and injecting the solution intradermally at multiple sites. One month later the animals are boosted with $\frac{1}{5}$ to $\frac{1}{10}$ the original amount of conjugate in Freud's complete adjuvant by subcutaneous injection at multiple sites. 7 to 14 days later the animals are bled and the serum is assayed for anti-TIE ligand homologue antibody titer. Animals are boosted until the titer plateaus. Preferably, the animal boosted with the conjugate of the same TIE ligand homologue, but conjugated to a different protein and/or through a different cross-linking reagent. Conjugates also can be made in recombinant cell culture as protein fusions. Also, aggregating agents such as alum are used to enhance the immune response.

Monoclonal antibodies are obtained from a population of substantially homogeneous antibodies, i.e., the individual antibodies comprising the population are identical except for possible naturally-occurring mutations that may be present in minor amounts. Thus, the modifier "monoclonal" indicates the character of the antibody as not being a mixture of discrete antibodies. For example, the anti-TIE ligand homologue monoclonal antibodies of the invention may be made using the hybridoma method first described by Kohler & Milstein, Nature 256:495 (1975), or may be made by recombinant DNA methods [Cabilly, et al., U.S. Pat. No. 4,816,567].

In the hybridoma method, a mouse or other appropriate host animal, such as hamster is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol to form a hybridoma cell [Goding, *Monoclonal Antibodies: Principles and Practice*, pp.59–103 (Academic Press, 1986)].

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high level expression of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 cells available from the American Type Culture Collection, Rockville, Md. USA. Human myeloma and mouse-human heteromyeloma cell lines also have been described for the production of human monoclonal antibodies [Kozbor, *J. Immunol.* 133:3001 (1984); Brodeur, et al., *Monoclonal Antibody Production Techniques and Applications*, pp.51–63 (Marcel Dekker, Inc., New York, 1987)].

Culture medium in which hybridoma cells are growing is assayed for production of monoclonal antibodies directed against the TIE ligand homologue. Preferably, the binding specificity of monoclonal antibodies produced by hybridoma cells is determined by immuno precipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson & Pollard, Anal. Biochem. 107:220 (1980).

After hybridoma cells are identified that produce antibodies of the desired specificity, affinity, and/or activity, the clones may be subcloned by limiting dilution procedures and grown by standard methods. Goding, *Monoclonal Antibodies: Principles and Practice*, pp.59–104 (Academic Press, 1986). Suitable culture media for this purpose include, for example, Dulbecco's Modified Eagle's Medium or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies of the invention is readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., *Proc. Nat. Acad. Sci.* 81, 6851 (1984), or by covalently joining to the immunoglobulin coding sequence all or part of the coding sequence for a non-immunoglobulin polypeptide. In that manner, "chimeric" or "hybrid" antibodies are prepared that have the binding specificity of an anti-TIE ligand monoclonal antibody herein.

Typically such non-immunoglobulin polypeptides are substituted for the constant domains of an antibody of the invention, or they are substituted for the variable domains of one antigen-combining site of an antibody of the invention to create a chimeric bivalent antibody comprising one antigen-combining site having specificity for a TIE ligand homologue of the present invention and another antigen-combining site having specificity for a different antigen.

Chimeric or hybrid antibodies also may be prepared in vitro using known methods in synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, 32P, $^{35}S$, or $^{125}I$, a fluorescent or chemiluminescent compound, such as fluorescein isothiocyanate, rhodamine, or luciferin; biotin; radioactive isotopic labels, such as, e.g., $^{125}I$, $^{32}P$, $^{14}C$, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., *Nature* 144:945 (1962); David, et al., *Biochemistry* 13:1014 (1974); Pain, et al., *J. Immunol. Meth.* 40:219 (1981); and Nygren, *J. Histochem. and Cytochem.* 30:407 (1982).

The antibodies of the present invention may be employed in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard (which may be a TIE ligand homologue or an immunologically reactive portion thereof) to compete with the test sample analyte (TIE ligand homologue) for binding with a limited amount of antibody. The amount of TIE ligand homologue in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature* 321, 522–525 (1986); Riechmann et al., *Nature* 332, 323–327 (1988); Verhoeyen et al., *Science* 239, 1534–1536 (1988)], by substituting rodent CDRs or CDR sequences for the corresponding sequences of a human antibody. Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. application Ser. No. 07/934,373 filed Aug. 21, 1992, which is a continuation-in-part of application Ser. No. 07/715,272 filed Jun. 14, 1991.

Alternatively, it is now possible to produce transgenic animals (e.g. mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., *Proc. Natl. Acad. Sci. USA* 90, 2551–255 (1993); Jakobovits et al., *Nature* 362, 255–258 (1993).

Bispecific antibodies are monoclonal, preferably human or humanized, antibodies that have binding specificities for at least two different antigens. In the present case, one of the binding specificities is for a particular TIE ligand homologue, the other one is for any other antigen, and preferably for another ligand. For example, bispecific antibodies specifically binding two different TIE ligand homologues are within the scope of the present invention.

Methods for making bispecific antibodies are known in the art.

Traditionally, the recombinant production of bispecific antibodies is based on the coexpression of two immunoglobulin heavy chain-light chain pairs, where the two heavy chains have different specificities (Millstein and Cuello, *Nature* 305, 537–539(1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in PCT application publication No. WO93/08829(published May 13, 1993), and in Traunecker et al., *EMBO* 10, 3655–3659 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, and second and third constant regions of an immunoglobulin heavy chain (CH2 and CH3). It is preferred to have the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance. In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in copending application Ser. No. 07/931,811 filed Aug. 17, 1992.

For further details of generating bispecific antibodies see, for example, Suresh et al., *Methods in Enzymology* 121, 210 (1986).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444–6448 (1993).

An "isolated" antibody is defined similarly to the definition provided hereinabove for isolated polypeptides. Specifically, an "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The word "label" when used herein refers to a detectable compound or composition which is conjugated directly or indirectly to the antibody so as to generate a "labeled" antibody. The label may be detectable by itself (e g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

Antibody "agonists" and "antagonists" are as hereinabove defined.

Hetero conjugate antibodies are also within the scope of the present invention. Hetero conjugate antibodies are composed of two covalently joined antibodies. Such antibodies have, for example, been proposed to target immune system cells to unwanted cells (U.S. Pat. No. 4,676,980), and for treatment of HIV infection (PCT application publication Nos. WO 91/00360 and WO 92/200373; EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Pluckthun in *The Pharmacology of Monoclonal Antibodies*, vol. 113, Rosenburg and Moore eds., Springer-Verlag, New York, pp. 269–315 (1994).

C. Cloning and Expression of the TIE Ligand Homologues

In the context of the present invention the expressions "cell", "cell line", and "cell culture" are used interchangeably, and all such designations include progeny. It is also understood that all progeny may not be precisely identical in DNA content, due to deliberate or inadvertent mutations. Mutant progeny that have the same function or biological property, as screened for in the originally transformed cell, are included.

The terms "replicable expression vector" and "expression vector" refer to a piece of DNA, usually double-stranded, which may have inserted into it a piece of foreign DNA. Foreign DNA is defined as heterologous DNA, which is DNA not naturally found in the host cell. The vector is used to transport the foreign or heterologous DNA into a suitable host cell. Once in the host cell, the vector can replicate independently of the host chromosomal DNA, and several copies of the vector and its inserted (foreign) DNA may be generated. In addition, the vector contains the necessary elements that permit translating the foreign DNA into a polypeptide. Many molecules of the polypeptide encoded by the foreign DNA can thus be rapidly synthesized.

Expression and cloning vectors are well known in the art and contain a nucleic acid sequence that enables the vector to replicate in one or more selected host cells. The selection of the appropriate vector will depend on 1) whether it is to be used for DNA amplification or for DNA expression, 2) the size of the DNA to be inserted into the vector, and 3) the host cell to be transformed with the vector. Each vector contains various components depending on its function (amplification of DNA of expression of DNA) and the host cell for which it is compatible. The vector components generally include, but are not limited to, one or more of the following: a signal sequence, an origin of replication, one or more marker genes, an enhancer element, a promoter, and a transciption termination sequence.

(i) Signal Sequence Component

In general, the signal sequence may be a component of the vector, or it may be a part of the TIE ligand homologue molecule that is inserted into the vector. If the signal sequence is heterologous, it should be selected such that it is recognized and processed (i.e. cleaved by a signal peptidase) by the host cell.

Heterologous signal sequences suitable for prokaryotic host cells are preferably prokaryotic signal sequences, such as the α-amylase, ompA, ompC, ompE, ompF, alkaline phosphatase, penicillinase, lpp, or heat-stable enterotoxin II leaders. For yeast secretion the yeast invertase, amylase, alpha factor, or acid phosphatase leaders may, for example, be used. In mammalian cell expression mammalian signal sequences are most suitable. The listed signal sequences are for illustration only, and do not limit the scope of the present invention in any way.

(ii) Origin of Replication Component

Both expression and cloning vectors contain a nucleic acid sequence that enabled the vector to replicate in one or more selected host cells. Generally, in cloning vectors this sequence is one that enables the vector to replicate independently of the host chromosomes, and includes origins of replication or autonomously replicating sequences. Such sequence are well known for a variety of bacteria, yeast and viruses. The origin of replication from the well-known plasmid pBR322 is suitable for most gram negative bacteria, the $2\mu$ plasmid origin for yeast and various viral origins (SV40, polyoma, adenovirus, VSV or BPV) are useful for cloning vectors in mammalian cells. Origins of replication are not needed for mammalian expression vectors (the SV40 origin may typically be used only because it contains the early promoter). Most expression vectors are "shuttle" vectors, i.e. they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA is also cloned by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of the DNA encoding the desired heterologous polypeptide. However, the recovery of genomic DNA is more complex than that of an exogenously replicated vector because restriction enzyme digestion is required to excise the encoded polypeptide molecule.

(iii) Selection Gene Component

Expression and cloning vectors should contain a selection gene, also termed a selectable marker. This is a gene that encodes a protein necessary for the survival or growth of a host cell transformed with the vector. The presence of this gene ensures that any host cell which deletes the vector will not obtain an advantage in growth or reproduction over transformed hosts. Typical selection genes encode proteins that (a) confer resistance to antibiotics or other toxins, e.g. ampicillin, neomycin, methotrexate or tetracycline, (b) complement auxotrophic deficiencies, or (c) supply critical nutrients not available from complex media, e.g. the gene encoding D-alanine racemase for bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin [Southern et al., *J. Molec. Appl. Genet.* 1, 327 (1982)], mycophenolic acid [Mulligan et al., *Science* 209, 1422 (1980)], or hygromycin [Sudgen et al., *Mol. Cel. Biol.* 5, 410–413 (1985)]. The three examples given above employ bacterial genes under eukaryotic control to convey resistance to the appropriate drug G418 or neomycin (geneticin), xgpt (mycophenolic acid), or hygromycin, respectively. Other examples of suitable selectable markers for mammalian cells are dihydrofolate reductase (DHFR) or thymidine kinase. Such markers enable the identification of cells which were competent to take up the desired nucleic acid. The mammalian cell transformants are placed under selection pressure which only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes the desired polypeptide. Amplification is the process by which genes in greater demand for the production of a protein critical for growth are reiterated in tandem within the chromosomes of successive generations of recombinant cells. Increased quantities of the desired polypeptide are synthesized from the amplified DNA.

For example, cells transformed with the DHFR selection gene are first identified by culturing all of the transformants in a culture medium which lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Nat'l. Acad. Sci. USA* , 77, 4216 (1980). A particularly useful DHFR is a mutant DHFR that is highly resistant to MIX (EP 117,060). This selection agent can be used with any otherwise suitable host, e.g. ATCC No. CCL61 CHO-K1, notwithstanding the presence of endogenous DHFR. The DNA encoding DHFR and the desired polypeptide, respectively, then is amplified by exposure to an agent (methotrexate, or MTX) that inactivates the DHFR. One ensures that the cell requires more DHFR (and consequently amplifies all exogenous DNA) by selecting only for cells that can grow in successive rounds of ever-greater MTX concentration. Alternatively, hosts co-transformed with genes encoding the desired polypeptide, wild-type DHFR, and another selectable marker such as the neo gene can be identified using a selection agent for the selectable marker such as G418 and then selected and amplified using methotrexate in a wild-type host that contains endogenous DHFR. (See also U.S. Pat. No. 4,965,199).

A suitable selection gene for use in yeast is the trp1 gene present in the yeast plasmid YRp7 (Stinchcomb et al., 1979, *Nature* 282:39; Kingsman et al., 1979, *Gene* 7:141; or Tschemper et al., 1980, *Gene* 10:157). The trp1 gene provides a selection marker for a mutant stain of yeast lacking the ability to grow in tryptophan, for example, ATCC No. 44076 or PEP4-1 (Jones, 1977, *Genetics* 85:12). The presence of the trp1 lesion in the yeast host cell genome then provides an effective environment for detecting transformation by growth in the absence of tryptophan. Similarly, Leu2 deficient yeast strains (ATCC 20,622 or 38,626) are complemented by known plasmids bearing the Leu2 gene.

(iv) Promoter Component

Expression vectors, unlike cloning vectors, should contain a promoter which is recognized by the host organism and is operably linked to the nucleic acid encoding the desired polypeptide. Promoters are untranslated sequences located upstream from the start codon of a structural gene (generally within about 100 to 1000 bp) that control the transcription and translation of nucleic acid under their control. They typically fall into two classes, inducible and constitutive. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known. These promoters are operably linked to DNA encoding the desired polypeptide by removing them from their gene of origin by restriction enzyme digestion, followed by insertion 5' to the start codon for the polypeptide to be expressed. This is not to say that the genomic promoter for a TIE ligand homologue is not usable. However, heterologous promoters generally will result in greater transcription and higher yields of expressed TIE ligand homologues as compared to the native TIE ligand homologue promoters.

Promoters suitable for use with prokaryotic hosts include the β-lactamase and lactose promoter systems (Chang et al., *Nature* 275:615 (1978); and Goeddel et al., *Nature* 281:544 (1979)), alkaline phosphatase, a tryptophan (trp) promoter system (Goeddel, *Nucleic Acids Res.* 8:4057(1980) and EPO Appln. Publ. No. 36,776) and hybrid promoters such as the tac promoter (H. de Boer et al., *Proc. Nat'l. Acad. Sci. USA* 80:21–25 (1983)). However, other known bacterial promoters are suitable. Their nucleotide sequences have been published, thereby enabling a skilled worker operably to ligate them to DNA encoding a TIE ligand homologue (Siebenlist et al., *Cell* 20:269 (1980)) using linkers or adaptors to supply any required restriction sites. Promoters for use in bacterial systems also will contain a Shine-Dalgarno (S.D.) sequence operably linked to the DNA encoding a TIE ligand homologue.

Suitable promoting sequences for use with yeast hosts include the promoters for 3-phosphoglycerate kinase (Hitzeman et al. *J. Biol. Chem.* 255:2073 (1980)) or other glycolytic enzymes (Hess et al., *J. Adv. Enzyme Reg.* 7:149 (1978); and Holland, *Biochemistry* 17:4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., EP 73,657A. Yeast enhancers also are advantageously used with yeast promoters.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into mammalian expression vectors.

TIE ligand homologue transcription from vectors in mammalian host cells may be controlled by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g. the actin promoter or an immunoglobulin promoter, from heat shock promoters, and from the promoter normally associated with the TIE ligand sequence, provided such promoters are compatible with the host cell systems.

The early and late promoters of the SV40 virus are conveniently obtained as an SV40 restriction fragment which also contains the SV40 viral origin of replication [Fiers et al., *Nature* 273:113 (1978), Mulligan and Berg, *Science* 209, 1422–1427 (1980); Pavlakis et al., *Proc. Natl. Acad. Sci. USA* 78, 7398–7402 (1981)]. The immediate early promoter of the human cytomegalovirus is conveniently obtained as a Hind III E restriction fragment [Greenaway et al., *Gene* 18, 355–360 (1982)]. A system for expressing DNA in mammalian hosts using the bovine papilloma virus as a vector is disclosed in U.S. Pat. No. 4,419,446. A modification of this system is described in U.S. Pat. No.

4,601,978. See also, Gray et al., *Nature* 295, 503–508 (1982) on expressing cDNA encoding human immune interferon in monkey cells; Reyes et al., *Nature* 297, 598–601 (1982) on expressing human β-interferon cDNA in mouse cells under the control of a thymidine kinase promoter from herpes simplex virus; Canaani and Berg, *Proc. Natl. Acad. Sci. USA* 79, 5166–5170 (1982) on expression of the human interferon β1 gene in cultured mouse and rabbit cells; and Gorman et al., *Proc. Natl. Acad. Sci. USA* 79, 6777–6781 (1982) on expression of bacterial CAT sequences in CV-1 monkey kidney cells, chicken embryo fibroblasts, Chinese hamster ovary cells, HeLa cells, and mouse HIN-3T3 cells using the Rous sarcoma virus long terminal repeat as a promoter.

(v) Enhancer Element Component

Transcription of a DNA encoding a TIE ligand homologues of the present invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent having been found 5' [Laimins et al., *Proc. Natl. Acad. Sci. USA* 78, 993 (1981)] and 3' [Lasky et al., *Mol. Cel. Biol.* 3, 1108 (1983)] to the transcription unit, within an intron [Banerji et al., *Cell* 33, 729 (1983)] as well as within the coding sequence itself [Osborne et al., *Mol. Cel. Biol.* 4, 1293 (1984)]. Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature* 297, 17–18 (1982) on enhancing elements for activation of eukaryotic promoters. The enhancer may be spliced into the vector at a position 5' or 3' to the TIE ligand DNA, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding the TIE ligand homologue. The 3' untranslated regions also include transcription termination sites.

Construction of suitable vectors containing one or more of the above listed components, the desired coding and control sequences, employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.* 9, 309 (1981) or by the method of Maxam et al., *Methods in Enzymology* 65, 499 (1980).

Particularly useful in the practice of this invention are expression vectors that provide for the transient expression in mammalian cells of DNA encoding a TIE ligand homologue. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient systems, comprising a suitable expression vector and a host cell, allow for the convenient positive identification of polypeptides encoded by clones DNAs, as well as for the rapid screening of such polypeptides for desired biological or physiological properties. Thus, transient expression systems are particularly useful in the invention for purposes of identifying analogs and variants of a TIE ligand homologue.

Other methods, vectors, and host cells suitable for adaptation to the synthesis of the TIE polypeptides in recombinant vertebrate cell culture are described in Getting et al., *Nature* 293, 620–625 (1981); Mantel et al., *Nature* 281, 40–46 (1979); Levinson et al.; EP 117,060 and EP 117,058. A particularly useful plasmid for mammalian cell culture expression of the TIE ligand polypeptides is pRK5 (EP 307,247), along with its derivatives, such as, pRK5D that has an sp6 transcription initiation site followed by an SfiI restriction enzyme site preceding the Xho/NotII cDNA cloning sites, and pRK5B, a precursor of pRK5D that does not contain the SfiI site; see, Holmes et al., *Science* 253, 1278–1280 (1991).

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequences by the methods of Messing et al., *Nuclei Acids Res.* 9, 309 (1981) or by the method of Maxam et al., *Methods in Enzymology* 65, 499 (1980).

(viii) Transient Expression Vectors

Particularly useful in the practice of this invention are expression vectors that provide for the transient expression in mammalian cells of DNA encoding a TIE ligand. In general, transient expression involves the use of an expression vector that is able to replicate efficiently in a host cell, such that the host cell accumulates many copies of the expression vector and, in turn, synthesizes high level of a desired polypeptide encoded by the expression vector. Sambrook et al., supra, pp. 16.17–16.22. Transient expression systems, comprising a suitable expression vector and a host cell, allow for the convenient positive screening of such polypeptides for desired biological or physiological properties. Thus transient expression systems are particularly useful in the invention for purposes of identifying analogs and variants of native TIE ligand homologues with the requisite biological activity.

(ix) Suitable Exemplary Vertebrate Cell Vectors

Other methods, vectors, and host cells suitable for adaptation to the synthesis of a TIE ligand homologue (including functional derivatives of native proteins) in recombinant vertebrate cell culture are described in Gething et al., *Nature* 293, 620–625 (1981); Mantei et al., *Nature* 281, 40–46 (1979); Levinson et al., EP 117,060; and EP 117,058. A particularly useful plasmid for mammalian cell culture expression of a TIE ligand homologue is pRK5 (EP 307,247) or pSVI6B (PCT Publication No. WO 91/08291).

Suitable host cells for cloning or expressing the vectors herein are the prokaryote, yeast or higher eukaryote cells described above. Suitable prokaryotes include gram negative or gram positive organisms, for example *E. coli* or bacilli. A preferred cloning host is *E. coli* 294 (ATCC 31,446) although other gram negative or gram positive prokaryotes such as *E. coli* B, *E. coli* X1776 (ATCC 31,537), *E. coli* W3110 (ATCC 27,325), Pseudomonas species, or *Serratia Marcesans* are suitable.

In addition to prokaryotes, eukaryotic microbes such as filamentous fungi or yeast are suitable hosts for vectors herein. *Saccharomyces cerevisiae*, or common baker's yeast, is the most commonly used among lower eukaryotic host microorganisms. However, a number of other genera, species and strains are commonly available and useful herein, such as *S. pombe* [Beach and Nurse, Nature 290, 140 (1981)], *Kluyveromyces lactis* [Louvencourt et al., *J. Bacteriol.* 737 (1983)]; *yarrowia* (EP 402,226); *Pichia pastoris* (EP 183,070), *Trichoderma reesia* (EP 244,234), *Neurospora crassa* [Case et al., *Proc. Natl. Acad. Sci. USA* 76, 5259–5263 (1979)]; and Aspergillus hosts such as *A. nidulans* [Ballance et al., *Biochem. Biophys. Res. Commun.* 112, 284–289 (1983); Tilburn et al., *Gene* 26, 205–221 (1983); Yelton et al., *Proc. Natl. Acad. Sci. USA* 81, 1470–1474 (1984)] and *A. niger* [Kelly and Hynes, *EMBO J.* 4, 475–479 (1985)].

Suitable host cells may also derive from multicellular organisms. Such host cells are capable of complex processing and glycosylation activities. In principle, any higher eukaryotic cell culture is workable, whether from vertebrate or invertebrate culture, although cells from mammals such as humans are preferred. Examples of invertebrate cells include plants and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melangaster* (fruitfly), and *Bombyx mori* host cells have been identified. See, e.g. Luckow et al., *Bio/Technology* 6, 47–55 (1988); Miller et al., in *Genetic Engineering*, Setlow, J. K. et al., eds., Vol. 8 (Plenum Publishing, 1986), pp. 277–279; and Maeda et al., *Nature* 315, 592–594 (1985). A variety of such viral strains are publicly available, e.g. the L-1 variant of *Autographa californica* NPV, and such viruses may be used as the virus herein according to the present invention, particularly for transfection of *Spodoptera frugiperda* cells.

Generally, plant cells are transfected by incubation with certain stains of the bacterium *Agrobacterium tumefaciens* which has been previously manipulated to contain the TIE ligand DNA. During incubation of the plant cell culture with *A. tumefaciens*, the DNA encoding a TIE ligand is transferred to the plant cell host such that it is transfected, and will, under appropriate conditions, express the TIE ligand DNA. In addition, regulatory and signal sequences compatible with plant cells are available, such as the nopaline synthase promoter and polyadenylation signal sequences. Depicker et al., *J. Mol. Appl. Gen.* 1, 561 (1982). In addition, DNA segments isolated from the upstream region of the T-DNA 780 gene are capable of activating or increasing transcription levels of plant-expressible genes in recombinant DNA-containing plant tissue. See EP 321,196 published Jun. 21, 1989.

However, interest has been greatest in vertebrate cells, and propagation of vertebrate cells in culture (tissue culture) is per se well known. See *Tissue Culture*, Academic Press, Kruse and Patterson, editors (1973). Examples of useful mammalian host cell lines are monkey kidney CV1 line transformed by SV40 (COS-7, ATCC CRL 1651); human embryonic kidney cell line [293 or 293 cells subcloned for growth in suspension culture, Graham et al., *J. Gen. Virol.* 36, 59 (1977)]; baby hamster kidney cells 9BHK, ATCC CCL 10); Chinese hamster ovary cells/-DHFR [CHO, Urlaub and Chasin, *Proc. Natl. Acad. Sci. USA* 77, 4216 (1980)]; mouse sertolli cells [TM4, Mather, *Biol. Reprod.* 23, 243–251 (1980)]; monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL75); human liver cells (Hep G2, HB 8065); mouse mamnmary tumor (MMT 060562, ATCC CCL51); TRI cells [Mather et al., *Annals N.Y. Acad. Sci.* 383, 44068 (1982)]; MRC 5 cells; FS4 cells; and a human hepatoma cell line (Hep G2). Preferred host cells are human embryonic kidney 293 and Chinese hamster ovary cells.

Particularly preferred host cells for the purpose of the present invention are vertebrate cells producing the TIE ligand homologues of the present invention.

Host cells are transfected and preferably transformed with the above-described expression or cloning vectors and cultured in conventional nutrient media modified as is appropriate for inducing promoters or selecting transformants containing amplified genes.

Prokaryotes cells used to produced the TIE ligand homologues of this invention are cultured in suitable media as describe generally in Sambrook et al., supra.

Mammalian cells can be cultured in a variety of media. Commercially available media such as Ham's F10 (Sigma), Minimal Essential Medium (MEM, Sigma), RPMI-1640 (Sigma), and Dulbecco's Modified Eagle's Medium (DMEM, Sigma) are suitable for culturing the host cells. In addition, any of the media described in Ham and Wallace, *Meth. Enzymol.* 58, 44 (1979); Barnes and Sato, *Anal. Biochem.* 102, 255 (1980), U.S. Pat. Nos. 4,767,704; 4,657, 866; 4,927,762; or 4,560,655; WO 90/03430; WO 87/00195 or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug) trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH and the like, suitably are those previously used with the host cell selected for cloning or expression, as the case may be, and will be apparent to the ordinary artisan.

The host cells referred to in this disclosure encompass cells in in vitro cell culture as well as cells that are within a host animal or plant.

It is further envisioned that the TIE ligand homologues of this invention may be produced by homologous recombination, or with recombinant production methods utilizing control elements introduced into cells already containing DNA encoding the particular TIE ligand homologue.

Gene amplification and/or expression may be measured in a sample directly, for example, by conventional Southern blotting, Northern blotting to quantitate the transcription of mRNA [Thomas, *Proc. Natl. Acad. Sci. USA* 77, 5201–5205

(1980)], dot blotting (DNA analysis), or in situ hybridization, using an appropriately labeled probe, based on the sequences provided herein. Various labels may be employed, most commonly radioisotopes, particularly $^{32}$P. However, other techniques may also be employed, such as using biotin-modified nucleotides for introduction into a polynucleotide. The biotin then serves as a site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to the surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hse et al., *Am. J. Clin. Pharm.* 75, 734–738 (1980).

Antibodies useful for immunohistochemical staining and/or assay of sample fluids may be either monoclonal or polyclonal, and may be prepared in any animal. Conveniently, the antibodies may be prepared against a native TIE ligand homologue polypeptide of the present invention, or against a synthetic peptide based on the DNA sequence provided herein as described further hereinbelow.

The TIE ligand homologue may be produced in host cells in the form of inclusion bodies or secreted into the periplasmic space or the culture medium, and is typically recovered from host cell lysates. The recombinant ligands may be purified by any technique allowing for the subsequent formation of a stable protein.

When the TIE ligand homologue is expressed in a recombinant cell other than one of human origin, it is completely free of proteins or polypeptides of human origin. However, it is necessary to purify the TIE ligand homologue from recombinant cell proteins or polypeptides to obtain preparations that are substantially homogenous as to the ligand. As a first step, the culture medium or lysate is centrifuged to remove particulate cell debris. The membrane and soluble protein fractions are then separated. The TIE ligand homologue may then be purified from the soluble protein fraction. The following procedures are exemplary of suitable purification procedures: fractionation on immunoaffinity or ion-exchange columns; ethanol precipitation; reverse phase HPLC; chromatography on silica or on a cation exchange resin such as DEAE; chromatofocusing; SDS-PAGE; ammonium sulfate precipitation; gel filtration using, for example, Sephadex G-75; and protein A Sepharose columns to remove contaminants such as IgG.

Functional derivatives of the TIE ligand homologues in which residues have been deleted, inserted and/or substituted are recovered in the same fashion as the native ligands, taking into account of any substantial changes in properties occasioned by the alteration. For example, fusion of the TIE ligand homologue with another protein or polypeptide, e.g. a bacterial or viral antigen, facilitates purification; an immunoaffinity column containing antibody to the antigen can be used to absorb the fusion. Immunoaffinity columns such as a rabbit polyclonal anti-TIE ligand homologue column can be employed to absorb TIE ligand homologue variants by binding to at least one remaining immune epitope. A protease inhibitor, such as phenyl methyl sulfonyl fluoride (PMSF) also may be useful to inhibit proteolytic degradation during purification, and antibiotics may be included to prevent the growth of adventitious contaminants. The TIE ligand homologues of the present invention are conveniently purified by affinity chromatography, based upon their ability to bind to a TIE receptor, known or hereinafter discovered, e.g. TIE-2.

One skilled in the art will appreciate that purification methods suitable for native TIE ligand homologues may require modification to account for changes in the character of a native TIE ligand homologue or its variants upon expression in recombinant cell culture

D. Use of the TIE Ligand Homologues, Nucleic Acid Molecules and Antibodies

The TIE ligand homologues of the present invention are useful in promoting the survival and/or growth and/or differentiation of TIE receptor expressing cells in cell culture.

The TIE ligand homologues may be additionally used to identify cells which express native TIE receptors. To this end, a detectably labeled ligand is contacted with a target cell under condition permitting its binding to the TIE receptor, and the binding is monitored.

The TIE ligand homologues herein may also be used to identify molecules exhibiting a biological activity of a TIE ligand homologue, for example, by exposing a cell expressing a TIE ligand homologue herein to a test molecule, and detecting the specific binding of the test molecule to a TIE receptor, either by direct detection, or based upon secondary biological effects. This approach is particularly suitable for identifying new members of the TIE ligand family, or for screening peptide or non-peptide small molecule libraries.

The TIE ligand homologues disclosed herein are also useful in screening assays designed to identify agonists or antagonists of a native TIE receptor that play an important role in bone development, maturation or growth, or in muscle growth or development and/or promote or inhibit angiogenesis. For example, antagonists of a TIE receptor may be identified based upon their ability to block the binding of a TIE ligand homologue of the present invention to a native TIE receptor, as measured, for example, by using BiAcore biosensor technology (BIAcore; Pharmacia Biosensor, Midscataway, N.J.); or by monitoring their ability to block the biological response caused by a biologically active TIE ligand homologue herein. Biological responses that may be monitored include, for example, the phosphorylation of the TIE receptor or downstream components of the TIE signal transduction pathway, or survival, growth or differentiation of cells expressing the TIE receptor. Cell-based assays, utilizing cells that do not normally the TIE receptor, engineered to express this receptor, or to coexpress the TIE receptor and a TIE ligand homologue of the present invention, are particularly convenient to use.

In a particular embodiment, small molecule agonists and antagonists of a native TIE receptor can be identified, based upon their ability to interfere with the TIE ligand/TIE receptor interaction. There are numerous ways for measuring the specific binding of a test molecule to a TIE receptor, including, but not limited to detecting or measuring the amount of a test molecule bound to the surface of intact cells expressing the TIE receptor, cross-linked to the TIE receptor in cell lysates, or bound to the TIE receptor in vitro.

Detectably labeled TIE ligand homologues include, for example, TIE ligand homologues covalently or non-covalently linked to a radioactive substances, e.g. $^{125}$I, a fluorescent substance, a substance having enzymatic activity (preferably suitable for colorimetric detection), a substrate for an enzyme (preferably suitable for colorimetric detection), or a substance that can be recognized by a(n) (detectably labeled) antibody molecule.

The assays of the present invention may be performed in a manner similar to that described in PCT Publication WO 96/11269, published Apr. 18, 1996.

The TIE ligand homologues of the present invention are also useful for purifying TIE receptors optionally used in the form of immunoadhesins, in which the TIE ligand homologue or the TIE receptor binding portion thereof is fused to an immunoglobulin heavy or light chain constant region.

The TIE ligand homologues herein, in particular NL5, NL8 and their functional derivatives, are also useful in inhibiting endothelial cell growth and/or inducing endothelial cell apoptosis.

The nucleic acid molecules of the present invention are useful for detecting the expression of TIE ligands in cells or tissue sections. Cells or tissue sections may be contacted with a detectably labeled nucleic acid molecule encoding a TIE ligand homologue of the present invention under hybridizing conditions, and the presence of mRNA hybridized to the nucleic acid molecule determined, thereby detecting the expression of the TIE ligand homologue. In addition, nucleic acid encoding a TIE ligand homologue herein that is amplified in tumor (cancer) cells, is useful in the diagnosis of tumor (cancer).

Antibodies of the present invention may, for example, be used in immunoassays to measure the amount of a TIE ligand homologue in a biological sample. The biological sample is contacted with an antibody or antibody mixture specifically binding a TIE ligand homologue of the present invention, and the amount of the complex formed with a ligand present in the test sample is measured.

Antibodies to the TIE ligand homologues herein may additionally be used for the delivery of cytotoxic molecules, e.g. radioisotopes or toxins, or therapeutic agents to cells expressing a corresponding TIE receptor. The therapeutic agents may, for example, be other TIE ligands, including the TIE-2 ligand, members of the vascular endothelial growth factor (VEGF) family, or known anti-tumor agents, and agents known to be associated with muscle growth or development, or bone development, maturation, or growth.

Anti-TIE ligand homologue antibodies are also suitable as diagnostic agents, to detect disease states associated with the expression of a TIE receptor. Thus, detectably labeled TIE ligand homologues and antibody agonists of a TIE receptor can be used for imaging the presence of angiogenesis.

In addition, the new TIE ligand homologues herein can be used to promote neovascularization, and may be useful for inhibiting tumor growth.

Antagonists of the TIE ligand homologues herein, e.g., anti-TIE ligand homologue antibodies, are further useful in the diagnosis and treatment of tumors (cancer) associated with the amplification of the genes encoding the respective TIE ligand homologues.

Further potential therapeutic uses include the modulation of muscle and bone development, maturation, or growth.

For therapeutic use, the TIE ligand homologues or anti-TIE ligand homologue antibodies of the present invention are formulated as therapeutic composition comprising the active ingredient(s) in admixture with a pharmacologically acceptable vehicle, suitable for systemic or topical application. The pharmaceutical compositions of the present invention are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or PEG.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules) or in macroemulsions. Such techniques are disclosed in *Remingtons Pharmaceutical Sciences*, supra.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial or intralesional routes, topical administration, or by sustained release systems.

Suitable examples of sustained release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (U. Sidman et al., 1983, "Biopolymers" 22 (1): 547–556), poly (2-hydroxyethyl-methacrylate) (R. Langer, et al., 1981, "J. Biomed. Mater. Res." 15: 167–277 and R. Langer, 1982, Chem. Tech." 12: 98–105), ethylene vinyl acetate (R. Langer et al., Id.) or poly-D-(-)-3-hydroxybutyric acid (EP 133, 988A). Sustained release compositions also include liposomes. Liposomes containing a molecule within the scope of the present invention are prepared by methods known per se: DE 3,218,121A; Epstein et al., 1985, "Proc. Natl. Acad. Sci. USA" 82: 3688–3692; Hwang et al., 1980, "Proc. Natl. Acad. Sci. USA" 77: 4030–4034; EP 52322A; EP 36676A; EP 88046A; EP 143949A; EP 142641A; Japanese patent application 83-118008; U.S. Pat. Nos. 4,485,045 and 4,544, 545; and EP 102,324A. Ordinarily the liposomes are of the small (about 200–800 Angstroms) unilamelar type in which the lipid content is greater than about 30 mol. % cholesterol, the selected proportion being adjusted for the optimal NT-4 therapy.

An effective amount of a molecule of the present invention to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. A typical daily dosage might range from about 1 µg/kg to up to 100 mg/kg or more, depending on the factors mentioned above. Typically, the clinician will administer a molecule of the present invention until a dosage is reached that provides the required biological effect. The progress of this therapy is easily monitored by conventional assays.

E. Amplification of Genes Encoding TIE Ligand Homologues in Tumor Tissues and Cell Lines The genome of prokaryotic and eukaryotic organisms is subjected to two seemingly conflicting requirements. One is the preservation and propagation of DNA as the genetic information in its original form, to guarantee stable inheritance through multiple generations. On the other hand, cells or organisms must be able to adapt to lasting environmental changes. The adaptive mechanisms can include qualitative or quantitative modifications of the genetic material. Qualitative modifications include DNA mutations, in which coding sequences are altered resulting in a structurally and/or functionally different protein. Gene amplification is a quantitative modification, whereby the actual number of complete coding sequence, i.e. a gene, increases, leading to an increased number of available templates for transcription, an increased number of translatable transcripts, and, ultimately, to an increased abundance of the protein encoded by the amplified gene.

The phenomenon of gene amplification and its underlying mechanisms have been investigated in vitro in several prokaryotic and eukaryotic culture systems. The best-characterized example of gene amplification involves the culture of eukaryotic cells in medium containing variable concentrations of the cytotoxic drug methotrexate (MTX). MTX is a folic acid analogue and interferes with DNA synthesis by blocking the enzyme dihydrofolate reductase (DHFR). During the initial exposure to low concentrations of MTX most cells (>99.9%) will die. A small number of cells survive, and are capable of growing in increasing concentrations of MTX by producing large amounts of DHFR-RNA and protein. The basis of this overproduction is the amplification of the single DHFR gene. The additional copies of the gene are found as extrachromosomal copies in the form of small, supernumerary chromosomes (double minutes) or as integrated chromosomal copies.

Gene amplification is most commonly encountered in the development of resistance to cytotoxic drugs (antibiotics for bacteria and chemotherapeutic agents for eukaryotic cells) and neoplastic transformation. Transformation of a eukaryotic cell as a spontaneous event or due to a viral or chemical/environmental insult is typically associated with changes in the genetic material of that cell. One of the most common genetic changes observed in human malignancies are mutations of the p53 protein. p53 controls the transition of cells from the stationary (G1) to the replicative (S) phase and prevents this transition in the presence of DNA damage. In other words, one of the main consequences of disabling p53 mutations is the accumulation and propagation of DNA damage, i.e. genetic changes. Common types of genetic changes in neoplastic cells are, in addition to point mutations, amplifications and gross, structural alterations, such as translocations.

The amplification of DNA sequences may indicate specific functional requirement as illustrated in the DHFR experimental system. Therefore, the amplification of certain oncogenes in malignancies points toward a causative role of these genes in the process of malignant transformation and maintenance of the transformed phenotype. This hypothesis has gained support in recent studies. For example, the bcl-2 protein was found to be amplified in certain types of non-Hodgkin's lymphoma. This protein inhibits apoptosis and leads to the progressive accumulation of neoplastic cells. Members of the gene family of growth factor receptors have been found to be amplified in various types of cancers suggesting that overexpression of these receptors may make neoplastic cells less susceptible to limiting amounts of available growth factor. Examples include the amplification of the androgen receptor in recurrent prostate cancer during androgen deprivation therapy and the amplification of the growth factor receptor homologue ERB2 in breast cancer. Lastly, genes involved in intracellular signaling and control of cell cycle progression can undergo amplification during malignant transformation. This is illustrated by the amplification of the bcl-I and ras genes in various epithelial and lymphoid neoplasms.

These earlier studies illustrate the feasibility of identifying amplified DNA sequences in neoplasms, because this approach can identify genes important for malignant transformation. The case of ERB2 also demonstrates the feasibility from a therapeutic standpoint, since transforming proteins may represent novel and specific targets for tumor therapy.

Several different techniques can be used to demonstrate amplified genomic sequences. Classical cytogenetic analysis of chromosome spreads prepared from cancer cells is adequate to identify gross structural alterations, such as translocations, deletions and inversions. Amplified genomic regions can only be visualized, if they involve large regions with high copy numbers or are present as extrachomosomal material. While cytogenetics was the first technique to demonstrate the consistent association of specific chromosomal changes with particular neoplasms, it is inadequate for the identification and isolation of manageable DNA sequences. The more recently developed technique of comparative genomic hybridization (CGH) has illustrated the widespread phenomenon of genomic amplification in neoplasms. Tumor and normal DNA are hybridized simultaneously onto metaphases of normal cells and the entire genome can be screened by image analysis for DNA sequences that are present in the tumor at an increased frequency. (WO 93/18,186; Gray et al., *Radiation Res.* 137, 275–289 [1994]). As a screening method, this type of analysis has revealed a large number of recurring amplicons (a stretch of amplified DNA) in a variety of human neoplasms. Although CGH is more sensitive than classical cytogenetic analysis in identifying amplified stretches of DNA, it does not allow a rapid identification and isolation of coding sequences within the amplicon by standard molecular genetic techniques.

The most sensitive methods to detect gene amplification are polymerase chain reaction (PCR)-based assays. These assays utilize very small amount of tumor DNA as starting material, are exquisitely sensitive, provide DNA that is amenable to further analysis, such as sequencing and are suitable for high-volume throughput analysis.

The above-mentioned assays are not mutually exclusive, but are frequently used in combination to identify amplifications in neoplasms. While cytogenetic analysis and CGH represent screening methods to survey the entire genome for amplified regions, PCR-based assays are most suitable for the final identification of coding sequences, i.e. genes in amplified regions.

According to the present invention, amplified genes have been identified by quantitative PCR (S. Gelmini et al., *Clin. Chem.* 43, 752 [1997]), by comparing DNA from a variety of primary tumors, including breast, lung, colon, prostate, brain, liver, kidney, pancreas, spleen, thymus, testis, ovary, uterus, etc. tumor, or tumor cell lines, with pooled DNA from healthy donors. Quantitative PCR was performed using a TaqMan instrument (ABI). Gene-specific primers and fluorogenic probes were designed based upon the coding sequences of the DNAs.

Human lung carcinoma cell lines include A549 (SRCC768), Calu-1 (SRCC769), Calu-6 (SRCC770), H157 (SRCC771), H441 (SRCC772), H460 (SRCC773), SKMES-1 (SRCC774) and SW900 (SRCC775), all available from ATCC. Primary human lung tumor cells usually derive from adenocarc inomas, squamous cell carcinomas, large cell carcinomas, non-small cell carcinomas, small cell carcinomas, and broncho alveolar carcinomas, and include, for example, SRCC724 (squamous cell carcinoma abbreviated as "SqCCa"), SRCC725 (non-small cell carcinoma, abbreviated as "NSCCa"), SRCC726 (adenocarcinoma, abbreviated as "AdenoCa"), SRCC727 (adenocarcinoma), SRCC728 (squamous cell carcinoma), SRCC729 (adenocarcinoma), SRCC730 (adeno/squamous cell carcinoma), SRCC731 (adenocarcinoma), SRCC732 (squamous cell carcinoma), SRCC733 (adenocarcinoma), SRCC734 (adenocarcinoma), SRCC735 (broncho alveolar carcinoma, abbreviated as "BAC"), SRCC736 (squamous cell carcinoma), SRCC738 (squamous cell carcinoma), SRCC739 (squamous cell carcinoma), SRCC740 (squamous cell carcinoma), SRCC740 (lung cell carcinoma, abbreviated as "LCCa").

Colon cancer cell lines include, for example, ATCC cell lines SW480 (adenocarcinoma, SRCC776), SW620 (lymph node metastasis of colon adenocarcinoma, SRCC777), COLO320 (adenocarcinoma, SRCC778), HT29 (adenocarcinoma, SRCC779), HM7 (carcinoma, SRCC780), CaWiDr (adenocarcinoma, srcc781), HCT116 (carcinoma, SRCC782), SKCO1 (adenocarcinoma, SRCC783), SW403 (adenocarcinoma, SRCC784), LS174T (carcinoma, SRCC785), and HM7 (a high mucin producing variant of ATCC colon adenocarcinoma cell line LS 174T, obtained from Dr. Robert Warren, UCSF). Primary colon tumors include colon adenoocarcinom as designated CT2 (SRCC742), CT3 (SRCC743), CT8 (SRCC744), CT10 (SRCC745), CT12 (SRCC746), CT14 (SRCC747), CT15 (SRCC748), CT17 (SRCC750), CT1 (SRCC751), CT4 (SRCC752), CT5 (SRCC753), CT6 (SRCC754), CT7 (SRCC755), CT9 (SRCC756), CT11 (SRCC757), CT18 (SRCC758), and DcR3, BACrev, BACfwd, T160, and T159.

Human breast carcinoma cell lines include, for example, HBL100 (SRCC759), MB435s (SRCC760), T47D (SRCC761), MB468 (SRCC762), MB175 (SRCC763), MB361 (SRCC764), BT20 (SRCC765), MCF7 (SRCC766), SKBR3 (SRCC767).

1. Tissue Distribution

The results of the gene amplification assays herein can be verified by further studies, such as, by determining mRNA expression in various human tissues.

As noted before, gene amplification and/or gene expression in various tissues may be measured by conventional Southern blotting, Northern blotting to quantitate the transcription of mRNA (Thomas, *Proc. Natl. Acad. Sci. USA.* 77:5201–5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence TIE ligand homologue polypeptide or against a synthetic peptide based on the DNA sequences provided herein or against exogenous sequence fused to TIE ligand homologue DNA and encoding a specific antibody epitope. General techniques for generating antibodies, and special protocols for Northern blotting and in situ hybridization are provided hereinbelow.

2. Chromosome Mapping

If the amplification of a given gene is functionally relevant, then that gene should be amplified more than neighboring genomic regions which are not important for tumor survival. To test this, the gene can be mapped to a particular chromosome, e.g. by radiation-hybrid analysis. The amplification level is then determined at the location identified, and at neighboring genomic region. Selective or preferential amplification at the genomic region to which to gene has been mapped is consistent with the possibility that the gene amplification observed promotes tumor growth or survival.

3. Antibody Binding Studies

The results of the gene amplification study can be further verified by antibody binding studies, in which the ability of anti-TIE ligand homologue antibodies to inhibit the effect of the TIE ligand homologue polypeptides on tumor (cancer) cells is tested. Exemplary antibodies include polyclonal, monoclonal, humanized, bispecific, and heteroconjugate antibodies, the preparation of which will be described hereinbelow.

Antibody binding studies may be carried out in any known assay method, such as competitive binding assays, direct and indirect sandwich assays, and immunoprecipitation assays. Zola, *Monoclonal Antibodies: A Manual of Techniques*, pp.147–158 (CRC Press, Inc., 1987).

Competitive binding assays rely on the ability of a labeled standard to compete with the test sample analyte for binding with a limited amount of antibody. The amount of target protein (encoded by a gene amplified in a tumor cell) in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

For immunohistochemistry, the tumor sample may be fresh or frozen or may be embedded in paraffin and fixed with a preservative such as formalin, for example.

4. Cell-Based Tumor Assays

Cell-based assays and animal models for tumors (e.g. cancers) can be used to verify the findings of the gene amplification assay, and further understand the relationship between the genes identified herein and the development and pathogenesis of neoplastic cell growth. The role of gene products identified herein in the development and pathology of tumor or cancer can be tested by using primary tumor cells or cells lines that have been identified to amplify the genes herein. Such cells include, for example, the breast, colon and lung cancer cells and cell lines listed above.

In a different approach, cells of a cell type known to be involved in a particular tumor are transfected with the cDNAs herein, and the ability of these cDNAs to induce excessive growth is analyzed. Suitable cells include, for example, stable tumor cells lines such as, the B104-1-1 cell line (stable NIH-3T3 cell line transfected with the neu protooncogene) and ras-transfected NIH-3T3 cells, which can be transfected with the desired gene, and monitored for tumorogenic growth. Such transfected cell lines can then be used to test the ability of poly- or monoclonal antibodies or antibody compositions to inhibit tumorogenic cell growth by exerting cytostic or cytotoxic activity on the growth of the transformed cells, or by mediating antibody-dependent cellular cytotoxicity (ADCC). Cells transfected with the coding sequences of the genes identified herein can further be used to identify drug candidates for the treatment of cancer.

In addition, primary cultures derived from tumors in transgenic animals (as described below) can be used in the cell-based assays herein, although stable cell lines are preferred. Techniques to derive continuous cell lines from transgenic animals are well known in the art (see, e.g. Small et al., *Mol. Cell. Biol.* 5, 642–648 [1985]).

5. Animal Models

A variety of well known animal models can be used to further understand the role of the genes identified herein in the development and pathogenesis of tumors, and to test the efficacy of candidate therapeutic agents, including antibodies, and other antagonists of the native polypeptides, including small molecule antagonists. The in vivo nature of such models makes them particularly predictive of responses in human patients. Animal models of tumors and cancers (e.g. breast cancer, colon cancer, prostate cancer, lung cancer, etc.) include both non-recombinant and recombinant (transgenic) animals. Non-recombinant animal models include, for example, rodent, e.g., murine models. Such models can be generated by introducing tumor cells into syngeneic mice using standard techniques, e.g. subcutaneous injection, tail vein injection, spleen implantation, intraperitoneal implantation, implantation under the renal capsule, or orthopin implantation, e.g. colon cancer cells implanted in colonic tissue. (See, e.g. PCT publication No. WO 97/33551, published Sep. 18, 1997).

Probably the most often used animal species in oncological studies are immunodeficient mice and, in particular, nude mice. The observation that the nude mouse with hypoplasia could successfully act as a host for human tumor xenografts has lead to its wide spread use for this purpose. The autosomal recessive nu gene has been introduced into a very large number of distinct congenic strains of nude mouse, including, for example, ASW, A/He, AKR, BALB/c, B10.LP, C17, C3H, C57BL, C57, CBA, DBA, DDD, I/st, NC, NFR, NFS, NFS/N, NZB, NZC, NZW, P, RIII and SJL. In addition, a wide variety of other animals with inherited immunological defects other than the nude mouse have been bred and used as recipients of tumor xenografts. For further details see, e.g. *The Nude Mouse in Oncology Research*, E. Boven and B. Winograd, eds., CRC Press, Inc., 1991.

The cells introduced into such animals can be derived from known tumor/cancer cell lines, such as, any of the above-listed tumor cell lines, and, for example, the B104-1-1 cell line (stable NIH-3T3 cell line transfected with the neu protooncogene); ras-transfected NIH-3T3 cells; Caco-2 (ATCC HTB-37); a moderately well-differentiated grade II human colon adenocarcinoma cell line, HT-29 (ATCC HTB-38), or from tumors and cancers. Samples of tumor or cancer cells can be obtained from patients undergoing surgery, using standard conditions, involving freezing and storing in liquid nitrogen (Karmali et al., *Br. J. Cancer* 48, 689–696 [1983]).

Tumor cells can be introduced into animals, such as nude mice by a variety procedures. The subcutaneous (s.c.) space in mice is very suitable for tumor implantation. Tumors can be transplanted s.c. as solid blocks, as needle biopsies by use of a trochar, or as cell suspensions. For solid block or trochar implantation, tumor tissue fragments of suitable size are introduced into the s.c. space. Cell suspensions are freshly prepared from primary tumors or stable tumor cell lines, and injected subcutaneously. Tumor cells can also be injected a subdermal implants. In this location, the inoculum is deposited between the lower part of the dermal connective tissue and the s.c. tissue. Boven and Winograd, supra.

Animal models of breast cancer can be generated, for example, by implanting rat neuroblastoma cells (from which the neu oncogen was initially isolated), or neu-transformed NIH-3T3 cells into nude mice, essentially as described by Drebin et al. *PNAS USA* 83, 9129–9133 (1986).

Similarly, animal models of colon cancer can be generated by passaging colon cancer cells in animals, e.g. nude mice, leading to the appearance of tumors in these animals. An orthotopic transplant model of human colon cancer in nude mice has been described, for example, by Wang et al., *Cancer Research* 54, 4726–4728 (1994) and Too et al., *Cancer Research* 55, 681–684 (1995). This model is based on the so-called "METAMOUSE" sold by AntiCancer, Inc. (San Diego, Calif.).

Tumors that arise in animals can be removed and cultured in vitro. Cells from the in vitro cultures can then be passaged to animals. Such tumors can serve as targets for further testing or drug screening. Alternatively, the tumors resulting from the passage can be isolated and RNA from pre-passage cells and cells isolated after one or more rounds of passage analyzed for differential expression of genes of interest. Such passaging techniques can be performed with any known tumor or cancer cell lines.

For example, Meth A, CMS4, CMS5, CMS21, and WEHI-164 are chemically induced fibrosarcomas of BALB/c female mice (DeLeo et al., *J. Exp. Med.* 146, 720 [1977]), which provide a highly controllable model system for studying the anti-tumor activities of various agents (Palladino et al., *J. Immunol.* 138, 4023–4032 [1987]). Briefly, tumor cells are propagated in vitro in cell culture. Prior to injection to the animals, the cell lines are washed and suspended in buffer, at a cell density of about $10\times10^6$ to $10\times10^7$ cells/ml. The animals are then infected subcutaneously with 100 to 100 μl of the cell suspension, allowing one to three weeks for a tumor to appear.

In addition, the Lewis lung (3LL) carcinoma of mice, which is one of the most throughly studied experimental tumors, can be used as an investigational tumor model. Efficacy in this tumor model has been correlated with beneficial effects in the treatment of human patients diagnosed with small cell carcinoma of the lung (SCCL). This tumor can be introduced in normal mice upon injection of tumor fragments from an affected mouse or of cells maintained in culture (Zupi et al., Br. J. Cancer 41, suppl. 4, 309 [1980]), and evidence indicates that tumors can be started from injection of even a single cell and that a very high proportion of infected tumor cells survive. For further information about this tumor model see Zacharski, Haemostasis 16, 300–320 [1986]).

One way of evaluating the efficacy of a test compound in an animal model is implanted tumor is to measure the size of the tumor before and after treatment. Traditionally, the size of implanted tumors has been measured with a slide caliper in two or three dimensions. The measure limited to two dimensions does not accurately reflect the size of the tumor, therefore, it is usually converted into the corresponding volume by using a mathematical formula. However, the measurement of tumor size is very inaccurate. The therapeutic effects of a drug candidate can be better described as treatment-induced growth delay and specific growth delay. Another important variable in the description of tumor growth is the tumor volume doubling time. Computer programs for the calculation and description of tumor growth are also available, such as the program reported by Rygaard and Spang-Thomsen, Proc. 6th Int. Workshop on Immune-Deficient Animals, Wu and Sheng eds., Basel, 1989, 301. It is noted, however, that necrosis and inflammatory responses following treatment may actually result in an increase in tumor size, at least initially. Therefore, these changes need to be carefully monitored, by a combination of a morphometric method and flow cytometric analysis.

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g. baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., Proc. Natl. Acad. Sci. USA 82, 6148–615 [1985]); gene targeting in embryonic stem cells (Thompson et al., Cell 5, 313–321 [1989]); electroporation of embryos (Lo, Mol. Cel. Biol. 3, 1803–1814 [1983]); sperm-mediated gene transfer (Lavitrano et al., Cell 57, 717–73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., Proc. Natl. Acad. Sci. USA 89, 6232–636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry. The animals are further examined for signs of tumor or cancer development.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell, 69:915 (1992)]. The selected cells are then injected into a blastocyst of an animal (e.g., a mouse or rat) to form aggregation chimeras [see e.g., Bradley, in Teratocarcinomas and Embryonic Stem Cells: A Practical Approach, E. J. Robertson, ed. (IRL, Oxford, 1987),pp. 113–152]. A chimeric embryo can then be implanted into a suitable pseudo pregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the FIZZ polypeptide.

The efficacy of antibodies specifically binding the polypeptides identified herein and other drug candidates, can be tested also in the treatment of spontaneous animal tumors. A suitable target for such studies is the feline oral squamous cell carcinoma (SCC). Feline oral SCC is a highly invasive, malignant tumor that is the most common oral malignancy of cats, accounting for over 60% of the oral tumors reported in this species. It rarely metastasizes to distant sites, although this low incidence of metastasis may merely be a reflection of the short survival times for cats with this tumor. These tumors are usually not amenable to surgery, primarily because of the anatomy of the feline oral cavity. At present, there is no effective treatment for this tumor. Prior to entry into the study, each cat undergoes complete clinical examination, biopsy, and is scanned by computed tomography (CT). Cats diagnosed with sublingual oral squamous cell tumors are excluded from the study. The tongue can become paralyzed as a result of such tumor, and even the treatment kills the tumor, the animals my not be able to feed themselves. Each cat is treated repeatedly, over a longer period of time. Photographs of the tumors will be taken daily during the treatment period, and at each subsequent recheck. After treatment, each cat undergoes another CT scan. CT scans and thoracic radiograms are evaluated every 8 weeks thereafter. The data are evaluated for differences in survival, response and toxicity as compared to control groups. Positive response may require evidence of tumor regression, preferably with improvement of quality of life and/or increased life span.

In addition, other spontaneous animal tumors, such as fibrosarcoma, adenocarcinoma, lymphoma, chrondroma, leiomyosarcoma of dogs, cats, and baboons can also be tested. Of these mammary adenocarcinomain dogs and cats is a preferred model as its appearance and behavior are very similar to those in humans. However, the use of this model is limited by the rare occurrence of this type of tumor in animals.

6. Methods of Treatment

It is contemplated that the antibodies and other anti-tumor compounds of the present invention may be used to treat various conditions, including those characterized by overexpression and/or activation of the amplified genes identified herein. Exemplary conditions or disorders to be treated with such antibodies and other compounds, including, but not limited to, small organic and inorganic molecules, peptides, antisense molecules, etc. include benign or malignant tumors (e.g renal, liver, kidney, bladder, breast, gastric, ovarian, colorectal, prostate, pancreatic, ling, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The anti-tumor agents of the present invention, e.g. antibodies, are administered to a mammal, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

Other therapeutic regimens may be combined with the administration of the anti-cancer agents, e.g. antibodies of the instant invention. For example, the patient to be treated with such anti-cancer agents may also receive radiation therapy. Alternatively, or in addition, a chemotherapeutic agent may be administered to the patient. Preparation and dosing schedules for such chemotherapeutic agents may be used according to manufacturers' instructions or as determined empirically by the skilled practitioner. Preparation and dosing schedules for such chemotherapy are also described in *Chemotherapy Service* Ed., M. C. Perry, Williams & Wilkins, Baltimore, Md. (1992). The chemotherapeutic agent may precede, or follow administration of the anti-tumor agent, e.g. antibody, or may be given simultaneously therewith. The antibody may be combined with an anti-oestrogen compound such as tamoxifen or an anti-progesterone such as onapristone (see, EP 616812) in dosages known for such molecules.

It may be desirable to also administer antibodies against other tumor associated antigens, such as antibodies which bind to the ErbB2, EGFR, ErbB3, ErbB4, or vascular endothelial factor (VEGF). Alternatively, or in addition, two or more antibodies binding the same or two or more different antigens disclosed herein may be co-administered to the patient. Sometimes, it may be beneficial to also administer one or more cytokines to the patient. In a preferred embodiment, the antibodies herein are co-administered with a growth inhibitory agent. For example, the growth inhibitory agent may be administered first, followed by an antibody of the present invention. However, simultaneous administration or administration of the antibody of the present invention first is also contemplated. Suitable dosages for the growth inhibitory agent are those presently used and may be lowered due to the combined action (synergy) of the growth inhibitory agent and the antibody herein.

For the prevention or treatment of disease, the appropriate dosage of an anti-tumor agent, e.g. an antibody herein will depend on the type of disease to be treated, as defined above, the severity and course of the disease, whether the agent is administered for preventive or therapeutic purposes, previous therapy, the patients clinical history and response to the agent, and the discretion of the attending physician. The agent is suitably administered to the patient at one time or over a series of treatments.

For example, depending on the type and severity of the disease, about 1 $\mu$g/kg to 15 mg/kg (e.g. 0.1–20 mg/kg) of antibody is an initial candidate dosage for administration to the patient, whether, for example, by one or more separate administrations, or by continuous infusion. A typical daily dosage might range from about 1 $\mu$g/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays 7. Articles of Manufacture In another embodiment of the invention, an article of manufacture containing materials useful for the diagnosis or treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually an anti-tumor agent capable of interfering with the activity of a gene product identified herein, e.g. an antibody. The label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

F. Screening Assays for Drug Candidates

Screening assays for drug candidates are designed to identify compounds that bind or complex with the polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly) peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art.

All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g. on a microtiter plate, by covalent or non-covalent attachments. Non-covalent attachment generally is accomplished by coating the solid surface with a solution of the polypeptide and drying. Alternatively, an immobilized antibody, e.g. a monoclonal antibody, specific for the polypeptide to be immobilized can be used to anchor it to a solid surface. The assay is performed by adding the non-immobilized component, which may be labeled by a detectable label, to the immobilized component, e.g. the coated surface containing the anchored component. When the reaction is complete, the non-reacted components are removed, e.g. by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular protein encoded by a gene identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature* London 340, 245–246 (1989); Chien et al., *Proc. Natl. Acad. Sci. USA* 88, 9578–9582 (1991)] as disclosed by Chevray and Nathans [*Proc. Natl. Acad. Sci. USA* 89, 5789–5793 (1991)]. Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In order to find compounds that interfere with the interaction of a gene identified herein and other intra- or extra-cellular components can be tested usually a reaction mixture is prepared containing the product of the amplified gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described hereinabove. The formation of a complex in the control reaction(s) but not in the reaction mixture containing the test compound indicates that the test compound interferes with the interaction of the test compound and its reaction partner.

Further details of the invention will be apparent from the following non-limiting examples.

REFERENCE EXAMPLE 1

Identification of the FLS 139 Ligand

FLS139 was identified in a cDNA library prepared from human fetal liver mRNA obtained from Clontech Laboratories, Inc. Palo Alto, Calif. USA, catalog no. 64018-1, following the protocol described in "Instruction Manual: Superscript® Lambda System for cDNA Synthesis and λ cloning," cat. No. 19643-014, Life Technologies, Gaithersburg, Md., USA which is herein incorporated by reference. Unless otherwise noted, all reagents were also obtained from Life Technologies. The overall procedure can be summarized into the following steps: (1) First strand synthesis; (2) Second strand synthesis; (3) Adaptor addition; (4) Enzymatic digestion; (5) Gel isolation of cDNA; (6) Ligation into vector; and (7) Transformation.

First Strand Synthesis

Not 1 primer-adapter (Life Tech., 2 µl, 0.5 µg/µl) was added to a sterile 1.5 ml microcentrifuge tube to which was added poly A+ mRNA (7 µl 5 µg). The reaction tube was heated to 70° C. for 5 minutes or time sufficient to denature the secondary structure of the mRNA. The reaction was then chilled on ice and 5× First strand buffer (Life Tech., 4 µl), 0.1 M DTT (2 µl) and 10 mM dNTP Mix (Life Tech., 1 µl) were added and then heated to 37° C. for 2 minutes to equilibrate the temperature. Superscript II® reverse transcriptase (Life Tech., 5 µl) was then added, the reaction tube mixed well and incubated at 37° C. for 1 hour, and terminated by placement on ice. The final concentration of the reactants was the following: 50 mM Tris-HCl (pH 8.3); 75 mM KCl; 3 mM $MgCl_2$; 10 mM DTT; 500 µM each dATP, dCTP, dGTP and dTTP; 50 µg/ml Not 1 primer-adapter, 5 µg (250 µg/ml) mRNA; 50,000 U/ml Superscript II® reverse transcriptase.

Second Strand Synthesis

While on ice, the following reagents were added to the reaction tube from the first strand synthesis, the reaction well mixed and allowed to react at 16° C. for 2 hours, taking care not to allow the temperature to go above 16° C.: distilled water (93 µl); 5× Second strand buffer (30 µl); dNTP mix (3 µl); 10 U/µl *E. coli* DNA ligase (1 µl); 10 U/µl *E. Coli* DNA polymerase I (4 µl); 2 U/µl *E. Coli* RNase H (1 µl). 10 U T4 DNA Polymerase (2 µl) was added and the reaction continued to incubate at 16° C. for another 5 minutes. The final concentration of the reaction was the following: 25 mM Tris-HCl (pH 7.5); 100 mM KCl; 5 mM $MgCl_2$; 10 mM $(NH_4)_2SO_4$; 0.15 mM β-NAD+; 250 µM each dATP, dCTP, dGTP, dTTP; 1.2 mM DTT; 65 U/ml DNA ligase; 250 U/ml DNA polymerase I; 13 U/ml Rnase H. The reaction has halted by placement on ice and by addition of 0.5 M EDTA (10 µl), then extracted through phenol:chloroform:isoamyl alcohol (25:24:1, 150 μl). The aqueous phase was removed, collected and diluted into 5M NaCl (15 μl) and absolute ethanol (−20° C., 400 μl) and centrifuged for 2 minutes at 14,000×g. The supernatant was carefully removed from the resulting DNA pellet, the pellet resuspended in 70% ethanol (0.5 ml) and centrifuged again for 2 minutes at 14,000×g. The supernatant was again removed and the pellet dried in a speedvac.

Adapter Addition

The following reagents were added to the cDNA pellet from the Second strand synthesis above, and the reaction was gently mixed and incubated at 16° C. for 16 hours: distilled water (25 μl); 5×T4 DNA ligase buffer (10 μl); Sal I adapters (10 μl); T4 DNA ligase (5 μl). The final composition of the reaction was the following: 50 mM Tris-HCl (pH 7.6); 10 mM MgCl$_2$; 1 mM ATP; 5% (w/v) PEG 8000; 1 mM DTT; 200 μg/ml Sal I adapters; 100 U/ml T4 DNA ligase. The reaction was extracted through phenol:chloroform:isoamyl alcohol (25:24:1, 50 μl), the aqueous phase removed, collected and diluted into 5M NaCl (8 μl) and absolute ethanol (−20° C., 250 μl). This was then centrifuged for 20 minutes at 14,000×g, the supernatant removed and the pellet was resuspended in 0.5 ml 70% ethanol, and centrifuged again for 2 minutes at 14,000×g. Subsequently, the supernatant was removed and the resulting pellet dried in a speedvac and carried on into the next procedure.

Enzymatic Digestion

To the cDNA prepared with the Sal I adapter from the previous paragraph was added the following reagents and the mixture was incubated at 37° C. for 2 hours: DEPC-treated water (41 μl); Not 1 restriction buffer (REACT, Life Tech., 5 μl), Not 1 (4 μl). The final composition of this reaction was the following: 50 mM Tris-HCl (pH 8.0); 10 mM MgCl$_2$; 100 mM MaCl; 1,200 U/ml Not 1.

Gel Isolation of cDNA

The cDNA is size fractionated by acrylamide gel electrophoresis on a 5% acrylamide gel, and any fragments which were larger than 1 Kb, as determined by comparison with a molecular weight marker, were excised from the gel. The cDNA was then electroeluted from the gel into 0.1×TBE buffer (200 μl) and extracted with phenol:chloroform:isoamyl alcohol (25:24:1, 200 μl). The aqueous phase was removed, collected and centrifuged for 20 minutes at 14,000×g. The supernatant was removed from the DNA pellet which was resuspended in 70% ethanol (0.5 ml) and centrifuged again for 2 minutes at 14,000×g. The supernatant was again discarded, the pellet dried in a speedvac and resuspended in distilled water (15 μl).

Ligation of cDNA into pRK5 Vector

The following reagents were added together and incubated at 16° C. for 16 hours: 5×T4 ligase buffer (3 μl); pRK5, Xho 1, Not1 digested vector, 0.5 μg, 1 μl); CDNA prepared from previous paragraph (5 μl) and distilled water (6 μl). Subsequently, additional distilled water (70 μl) and 10 mg/ml tRNA (0.1 μl) were added and the entire reaction was extracted through phenol:chloroform:isoamyl alcohol (25:24:1). The aqueous phase was removed, collected and diluted into 5M NaCl (10 μl) and absolute ethanol (−20° C., 250 μl). This was then centrifuged for 20 minutes at 14,000× g, decanted, and the pellet resuspended into 70% ethanol (0.5 ml) and centrifuged again for 2 minutes at 14,000×g. The DNA pellet was then dried in a speedvac and eluted into distilled water (3 μl) for use in the subsequent procedure.

Transformation of Library Ligation into Bacteria

The ligated cDNA/pRK5 vector DNA prepared previously was chilled on ice to which was added electrocompetent DH10B bacteria (Life Tech., 20 μl). The bacteria vector mixture was then electroporated as per the manufacturers recommendation. Subsequently SOC media (1 ml) was added and the mixture was incubated at 37° C. for 30 minutes. The transformants were then plated onto 20 standard 150 mm LB plates containing ampicillin and incubated for 16 hours (370° C.) to allow the colonies to grow. Positive colonies were then scraped off and the DNA isolated from the bacterial pellet using standard CsCl-gradient protocols. For example, Ausubel et al., 2.3.1.

Identification of FLS139

FLS139 can be identified in the human fetal liver library by any standard method known in the art, including the methods reported by Klein R. D. et al. (1996), *Proc. Natl. Acad. Sci.* 93, 7108–7113 and Jacobs (U.S. Pat. No. 5,563, 637 issued Jul. 16, 1996). According to Klein et al. and Jacobs, cDNAs encoding novel secreted and membrane-bound mammalian proteins are identified by detecting their secretory leader sequences using the yeast invertase gene as a reporter system. The enzyme invertase catalyzes the breakdown of sucrose to glucose and fructose as well as the breakdown of raffinose to sucrose and melibiose. The secreted form of invertase is required for the utilization of sucrose by yeast (*Saccharomyces cerevisiae*) so that yeast cells that are unable to produce secreted invertase grow poorly on media containing sucrose as the sole carbon and energy source. Both Klein R. D., supra, and Jacobs, supra, take advantage of the known ability of mammalian signal sequences to functionally replace the native signal sequence of yeast invertase. A mammalian cDNA library is ligated to a DNA encoding a nonsecreted yeast invertase, the ligated DNA is isolated and transformed into yeast cells that do not contain an invertase gene. Recombinants containing the nonsecreted yeast invertase gene ligated to a mammalian signal sequence are identified based upon their ability to grow on a medium containing only sucrose or only raffinose as the carbon source. The mammalian signal sequences identified are then used to screen a second, full-length cDNA library to isolate the full-length clones encoding the corresponding secreted proteins.

The nucleotide sequence of FLS139 is shown in FIGS. 1A-1 and 1A-2 (SEQ. ID. NO: 16), while its amino acid sequence is shown in FIGS. 1B-1 and 1B-2 (SEQ. ID. NO: 17). FLS139 contains a fibrinogen-like domain exhibiting a high degree of sequence homology with the two known human ligands of the TIE-2 receptor (h-TIE2L1 and h-TIE2L2). Accordingly, FLS139 has been identified as a novel member of the TIE ligand family.

A clone of FLS139 was deposited with the American Type Culture Collection (ATCC), 10801 University Boulevard, Manassas, Va. 20110-2209, on Sep. 18, 1997 under the terms of the Budapest Treaty, and has been assigned the deposit number ATCC 209281.

EXAMPLE 1

Isolation of cDNA Clones Encoding Human NL1

NL1 was identified by screening the GenBank database using the computer program BLAST (Altshul et al., *Methods in Enzymology* 266:460–480 (1996)). The NL1 sequence shows homology with known expressed sequence tag (EST) sequences T35448, T11442, and W77823. None of the known EST sequences have been identified as full length sequences, or described as ligands associate 1 d with the TIE receptors.

Following its identification, NL1 was cloned from a human fetal lung library prepared from mRNA purchased from Clontech, Inc. (Palo Alto, Calif., USA), catalog #6528-1, following the manufacturer's instructions.

The library was ligated into pRK5B vector, which is a precursor of pRK5D that does not contain the SfiI site; see, Holmes et al., *Science*, 253:1278–1280 (1991). pRK5D, in turn, is a derivative of pRK5 (EP 307,247, published Mar. 15, 1989), with minor differences within the polylinker sequence. The library was screened by hybridization with synthetic oligonucleotide probes:

NL1.5-1 5'-GCTGACGAACCAAGGCA-
ACTACAAACTCCTGGT    SEQ. ID. NO: 7

NL1.3-1 5'-TGCGGCCGGACCAGTCCT-
CCATGGTCACCAGGAGTTTGTAG    SEQ. ID. NO: 8

NL1.3-2 5'-GGTGGTGAACTGCTTGCCG-
TTGTGCCATGTAAA    SEQ. ID. NO: 9 based on the ESTs found in the GenBank database. cDNA sequences were sequenced in their entireties.

The nucleotide and amino acid sequences of NL1 are shown in FIGS. 2A and 2B (SEQ. ID. NO:1), and FIGS. 3A and 3B (SEQ. ID. NO:2), respectively.

NL1 shows a 23% sequence identity with both the TIE1 and the TIE2 ligand.

A clone of NL1 was deposited with the American Type Culture Collection (ATCC), 10801 University Boulevard, Manassas, Va. 20110-2209, on Sep. 18, 1997, under the terms of the Budapest Treaty, and has been assigned the deposit number ATCC 209280.

NL1 has been mapped to chromosome 9, bandarm q13-q21.

EXAMPLE 2
Isolation of cDNA Clones Encoding Human NL5 and NL8

An expressed sequence tag (EST) DNA database (LIFESEQ™, Incyte Pharmaceuticals, Palo Alto, Calif.) was searched and ESTs were identified that showed homology to the FLS139 protein of Reference Example 1. To clone NL5 and NL8, a human fetal lung library prepared from mRNA purchased from Clontech, Inc. (Palo Alto, Calif., USA), catalog #6528-1 was used, following the manufacturer's instructions. The library was screened by hybridization with synthetic oligonucleotide probes:
NL5

NL5.5-1 5' CAGGTTATCCCAGAGATTT-
AATGCCACCA    SEQ. ID. NO: 10

NL5.3-1 5' TTGGTGGGAGAAGTTGCC-
AGATCAGGTGGTGGCA    SEQ. ID. NO: 11

NL5.3-2 5' TTCACACCATAACTGCATT-
GGTCCA    SEQ. ID. NO: 12

NL8

NL8.5-1 5' ACGTAGTTCCAGTATGGTG-
TGAGCAGCAACTGGA    SEQ. ID. NO:13

NL8.3-1 5' AGTCCAGCCTCCACCCTCC-
AGTTGCT    SEQ. ID. NO: 14

NL8.3-2 5' CCCCAGTCCTCCAGGAGAA-
CCAGCA    SEQ. ID. NO: 15 based on the ESTs found in the database. cDNA clones were sequenced in their entireties. The entire nucleotide and deduced amino acid sequences of NL5 are shown in FIGS. 4A–4C (SEQ. ID. NO: 3) and 5A and 5B (SEQ. ID. NO: 4). The entire nucleotide and deduced amino acid sequences of NL8 are shown in FIGS. 6A and 6B (SEQ. ID. NO: 5) and 7A and 7B (SEQ. ID. NO: 6).

Based on a BLAST and FastA sequence alignment analysis (using the ALIGN program) of the full-length sequences, NL5 shows a 24% sequence identity with both ligand 1 and ligand 2 of the TIE2 receptor. NL8 shows a 23% sequence identity with both ligand 1 and ligand 2 of the TIE2 receptor.

The fibrinogen domains of the TIE ligands NL1, NL5 and NL8 are 64–74% identical. More specifically, the fibrinogen domain of NL1 is 74% identical with the fibrinogen domain of NL5 and 63% identical with the fibrinogen domain of NL8, while the fibrinogen domain of NL5 is 57% identical with the fibrinogen domain of NL8. Ligand 1 and ligand 2 of the TIE-2 receptor are 64% identical and 40–43% identical to NL1, NL5 and NL8.

NL5 has been localized to chromosome 1, bandarm q23.

NL8 has been localized to chromosome 19, bandarms p13.3-p13.21, p13.3-p12.14, p13.3-p12.15.

EXAMPLE 3
Isolation of cDNA clones Encoding Human NL4

An expressed sequence tag (EST) DNA database (LIFESEQ™, Incyte Pharmaceuticals, Palo Alto, Calif.) was searched and an EST (#2939340) was identified which showed homology to human TIE-2 L1 and TIE-2 L2.

Based on the EST, a pair of PCR primers (forward and reverse), and a probe were synthesized:

NL4,5-1: TTCAGCACCAAGGACAAGGACAA-
TGACAACT    SEQ ID NO: 22

NL4,3-1: TGTGCACACTTGTCCAAGCAGTTG-
TCATTGTC    SEQ ID NO: 23

NL4,3-3: GTAGTACACTCCATTGAGGTTGG    SEQ ID NO: 24.

Oligo dT primed cDNA libraries were prepared from uterus mRNA purchased from Clontech, Inc. (Palo Alto, Calif., USA, catalog #6537-1) in the vector pRK5D using reagents and protocols from Life Technologies, Gaithersburg, Md. (Super Script Plasmid System). pRK5D is a cloning vector that has an sp6 transcription initiation site followed by an SfiI restriction enzyme site preceding the XhoI/NotI cDNA cloning sites. The cDNA was primed with oligo dT containing a NotI site, linked with blunt to SalI hemikinased adaptors, cleaved with NotI, sized to greater than 1000 bp appropriately by gel electrophoresis, and cloned in a defined orientation into XhoI/NotI-cleaved pRK5D.

In order to screen several libraries for a source of a full-length clone, DNA from the libraries was screened by PCR amplification with the PCR primer pair identified above. A positive library was then used to isolate clones encoding the NL4 gene using the probe oligonucleotide and one of the PCR primers.

DNA sequencing of the clones isolated as described above gave the full-length DNA sequence for NL4 and the derived protein sequence.

The entire nucleotide sequence of NL4 is shown in FIGS. 13A and 13B (SEQ ID NO: 18). Clone DNA47470 contains a single open reading frame with an apparent translational initiation site at nucleotide positions 215–217 (FIGS. 13A and 13B, where the ATG start codon is underlined). In FIGS. 13A and 13B, the TAA stop codon at nucleotide positions 1039–1041 is boxed. The predicted polypeptide is 346 amino acids long. Clone DNA47470 has been deposited with ATCC and is assigned ATCC deposit no. 209422.

Based on a BLAST and FastA sequence alignment analysis of the full-length sequence, NL4 shows amino acid sequence identity to TIE2L1 (32%) and TIE2L2 (34%).

EXAMPLE 4
Northern Blot and in situ RNA Hybridization Analysis

Expression of the NL1 and NL5 mRNA in human tissues was examined by Northern blot analysis. Human mRNA blots were hybridized to a $^{32}$P-labeled DNA probe based on the full length cDNAs; the probes were generated by digesting and purifying the cDNA inserts. Human fetal RNA blot MTN (Clontech) and human adult RNA blot MTN-II (Clontech) were incubated with the DNA probes. Blots were incubated with the probes in hybridization buffer (5×SSPE; 2Denhardt's solution; 100 mg/mL denatured sheared salmon sperm DNA; 50% formamide; 2% SDS) for 60 hours at 42° C. The blots were washed several times in 2×SSC; 0.05% SDS for 1 hour at room temperature, followed by a 30 minute wash in 0.1×SSC; 0.1% SDS at 50° C. The blots were developed after overnight exposure by phosphorimager analysis (Fuji).

Figure 11:
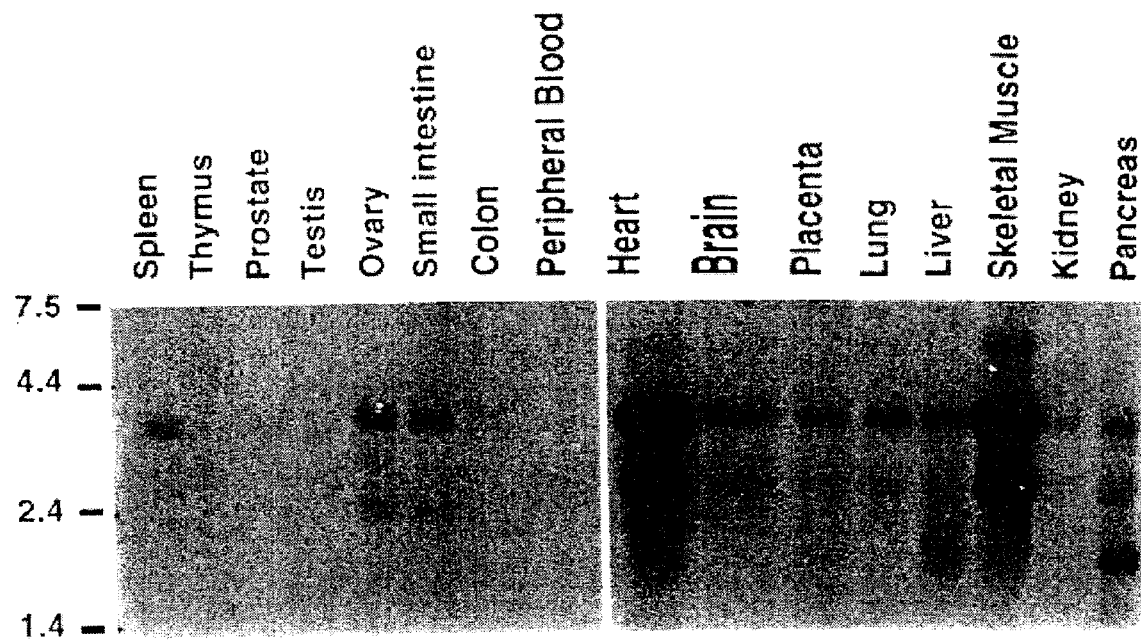
FIGS. 11 and 12—Northern blots showing the expression of the mRNAs of TIE ligands NL1 and NL5 in various tissues.
Figure 12:
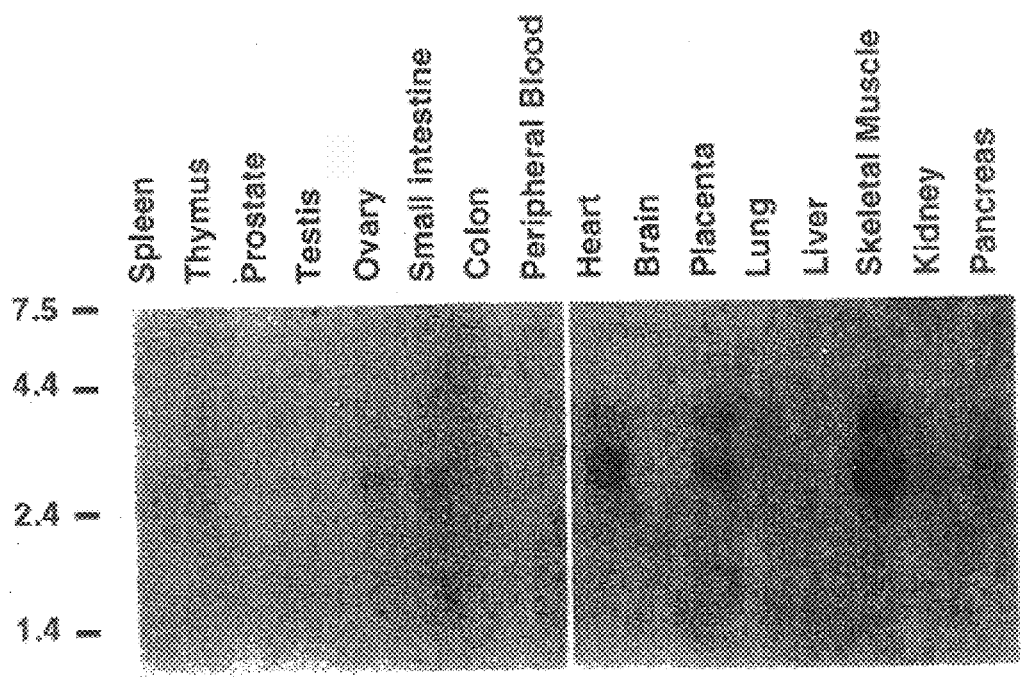

As shown in FIGS. 11 and 12, NL1 and NL5 mRNA transcripts were detected. Strong NL1 mRNA expression was detected in heart and skeletal muscle tissue and in the pancreas. NL5 mRNA was strongly expressed in skeletal muscle, and, to a lesser degree, heart, placenta and pancreas.

The tissue expression patterns of NL1, NL5, NL8 and NL4 were also determined by in situ hybridization (observing hybridization to cellular RNA), using an optimized protocol that employs PCR-generated $^{33}$P-labeled riboprobes. (Lu and Gillett, *Cell Vision* 1: 169–176(1994)). Formalin-fixed, paraffin-embedded human fetal and adult tissues were sectioned, deparaffinized, deproteinated in proteinase K (20 g/ml) for 15 minutes at 37° C., and further processed for in situ hybridization as described by Lu and Gillett (1994). A [$^{33}$-P] UTP-labeled antisense riboprobe was generated from a PCR product and hybridized at 55° C. overnight. The slides were dipped in Kodak NTB2 nuclear track emulsion and exposed for 4 weeks.

$^{33}$P-Riboprobe Synthesis 6.0 µl (125 mCi) of $^{33}$P-UTP (Amersham BF 1002, SA<2000 Ci/mmol) were speed vac dried. To each tube containing dried $^{33}$P-UTP, the following ingredients were added:

- 2.0 µl 5×transcription buffer
- 1.0 µl DTT (100 mM)
- 2.0 µl NTP mix (2.5 mM:10 µ; each of 10 mM GTP, CTP & ATP+10 µl H$_2$O)
- 1.0 µl UTP (50 µM)
- 1.0 µl Rnasin
- 1.0 µl DNA template (1 µg)
- 1.0 µl H$_2$O
- 1.0 µl RNA polymerase (for PCR products T3=AS, T7=S, usually)

The tubes were incubated at 37° C. for one hour. 1.0 µl RQ1 DNase were added, followed by incubation 37° C. for 15 minutes. 90 µl TE (10 mM Tris pH 7.6/1 mM EDTA pH 8.0) were added, and the mixture was pipetted onto DE81 paper The remaining solution was loaded in a Microcon-50 ultrafiltration unit, and spun using program 10 (6 minutes). The filtration unit was inverted over a second tube and spun using program 2 (3 minutes). After the final recovery spin, 100 µl TE were added. 1 µl of the final product was pipetted on DE81 paper and counted in 6 ml of Biofluor II.

The probe was run on a TBE/urea gel. 1–3 µl of the probe or 5 µl of RNA Mrk III were added to 3 µl of loading buffer. After beating on a 95° C. heat block for three minutes, the gel was immediately placed on ice. The wells of gel were flushed, the sample loaded, and run at 180–250 volts for 45 minutes. The gel was wrapped in saran wrap and exposed to XAR film with an intensifying screen in −70° C. freezer one hour to overnight

$^{33}$P-Hybridization
Pretreatment of Frozen Sections

The slides were removed from the freezer, placed on aluminium trays and thawed at room temperature for 5 minutes. The trays were placed in 55° C. Incubator for five minutes to reduce condensation. The slides were fixed for 10 minutes in 4% paraformaldehyde on ice in the fume hood, and washed in 0.5×SSC for 5 minutes, at room temperature (25 ml 20×SSC+975 ml SQ H$_2$O). After deproteination in 0.5 µg/ml proteinase K for 10 minutes at 37° C. (12.5 µl of 10 mg/ml stock in 250 ml prewarmed RNase-free RNAse buffer), the sections were washed in 0.5×SSC for 10 minutes at room temperature. The sections were dehydrated in 70%, 95%, 100% ethanol, 2 minutes each.

Pretreatment of Paraffin-embedded Sections

The slides were deparaffinized, placed in SQ H$_2$O, and rinsed twice in 2×SSC at room temperature, for 5 minutes each time. The sections were deproteinated in 20 µg/ml proteinase K (500 µl of 10 mg/ml in 250 ml RNase-free RNase buffer, 37° C., 15 minutes)—human embryo, or 8×proteinase K (100 µl in 250 ml Rnase buffer, 37° C., 30 minutes)—formalin tissues. Subsequent rinsing in 0.5×SSC and dehydration were performed as described above.

Prehybridization

The slides were laid out in plastic box lined with Box buffer (4×SSC, 50% formamide)—saturated filter paper. The tissue was covered with 50 µl of hybridization buffer (3.75 g Dextran Sulfate+6 ml SQ H$_2$O), vortexed and heated in the microwave for 2 minutes with the cap loosened. After cooling on ice, 18.75 ml formamide, 3.75 ml 20×SSC and 9 ml SQ H$_2$O were added, the tissue was vortexed well, and incubated at 42° C. for 1–4 hours.

Hybridization 1.0×10$^6$ cpm probe and 1.0 µl tRNA (50 mg/ml stock) per slide were heated at 95° C. for 3 minutes. The slides were cooled on ice, and 48 µl hybridization buffer were added per slide. After vortexing, 50 µl $^{33}$P mix were added to 50 µl prehybridization on slide. The slides were incubated overnight at 55° C.

Washes

Washing was done 2×10 minutes with 2×SSC, EDTA at room temperature (400 ml 20×SSC+16 ml 0.25M EDTA, V$_f$=4 L), followed by RNaseA treatment at 37° C. for 30 minutes (500 µl of 10 mg/ml in 250 ml Rnase buffer=20 µg/ml), The slides were washed 2×10 minutes with 2×SSC, EDTA at room temperature. The stringency wash conditions were as follows: 2 hours at 55° C., 0.1×SSC, EDTA (20 ml 20×SSC+16 ml EDTA, V$_f$=4 L).

Oligos

NL1:
- 46mer GGA TTC TAA TAC GAC TCA CTA TAG GGC CGG GTT CAC GGT GCC ATC T (SEQ ID NO: 25)
- 48mer CTA TGA AAT TAA CCC TCA CTA AAG GGA TGC GGT TGT AGG TGG GTG GTT (SEQ ID NO: 26)

NL5:
- 47mer GGA TTC TAA TAC GAC TCA CTA TAG GGC CAA CAC CAA GGG GCA AGA TG (SEQ ID NO: 27)
- 48mer CTA TGA AAT TAA CCC TCA CTA AAG GGA GGG CTT TTG GTG GGA GAA GTT (SEQ ID NO: 28)

NL4:
- 48mer GGA TTC TAA TAC GAC TCA CTA TAG GGC GCT CCG CAA AGG TGG CTA CTG (SEQ ID NO: 29)

47mer CTA TGA AAT TAA CCC TCA CTA AAG GGA TTT CCT CCC CGC AAG TCC AG (SEQ ID NO: 30)

NL8:
GGA TTC TAA TAC GAC TCA CTA TAG GGC GGC CGC CAC GAG GAG CTG TTA (SEQ ID NO: 31) CTA TGA AAT TAA CCC TCA CTA AAG GGA GGG GCT CTG GGG CTG GGT C (SEQ ID NO: 32)

Figure 8B:
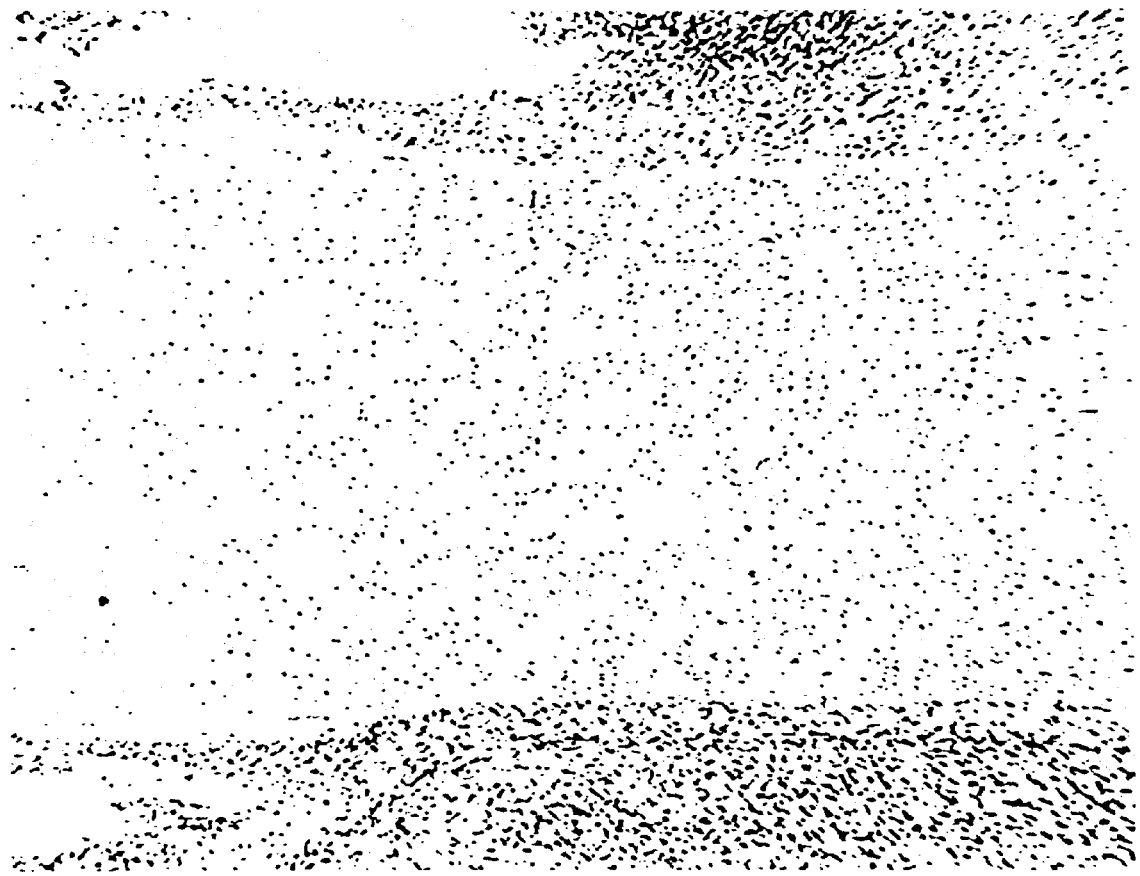

In situ hybridization results show that NL1 is expressed in the cartilage of developing long bones and in periosteum adjacent to differentiating osteoblasts. Expression was also observed in tendon, in connective tissue at sites of synovial joint formation, in connective tissue septa, and in the periosteum of fetal body wall (FIGS. 8-A and 8-B).

Figure 9A:
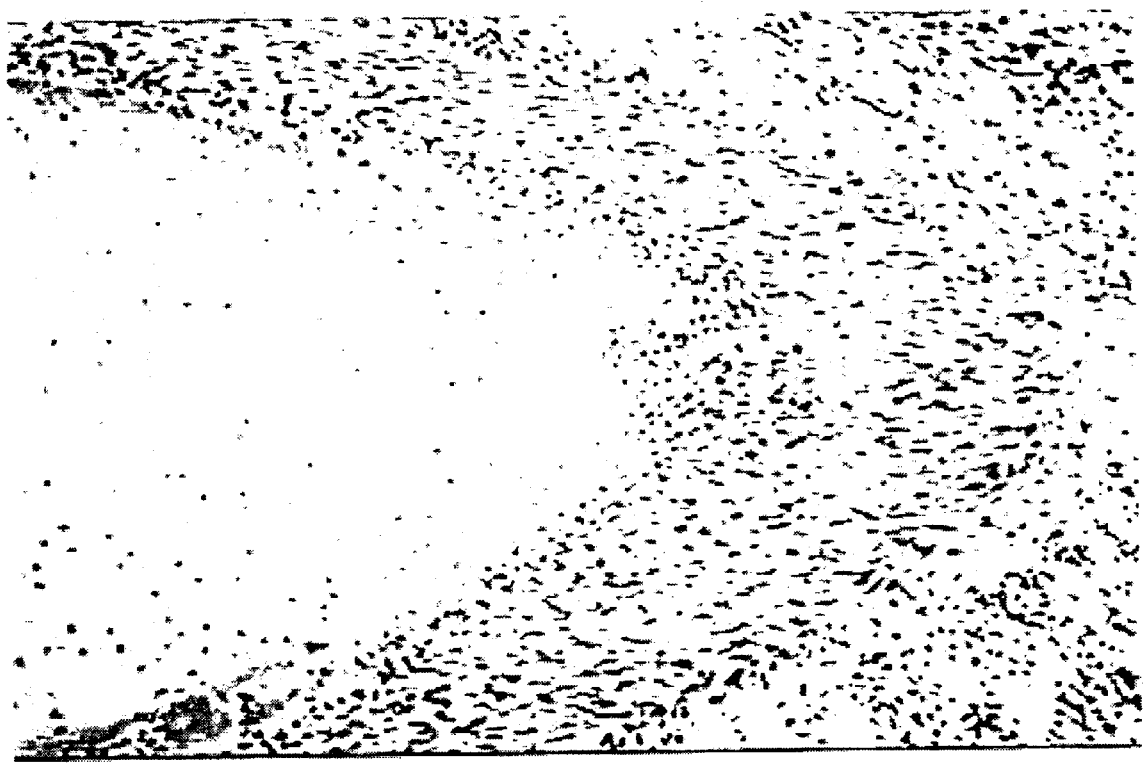
FIGS. 9-A and 9-B show the expression of NL5 in various tissues as determined by in situ hybridization to cellular RNA.
Figure 9B:

In situ hybridization indicated NL5 mRNA expression in adult human breast cancel cells over benign breast epithelium, areas of apocrine metaplasia and sclerosing adenosis. Expression was further observed over infiltrating breast ductal carcinoma cells. In fetal lower limb tissue, high expression was found at sites of enchondral bone formation, in osteocytes and in periosteum/perichondrium of developing bones. NL5 mRNA was also highly expressed in osteocytes and in periosteum/periochondrium of developing bones of fetal body wall tissue. This distribution suggests a role in bone formation and differentiation (FIGS. 9-A and 9-B).

Figure 10A:
FIGS. 10-A and 10-B show the expression of NL8 in various tissues as determined by in situ hybridization to cellular RNA.
Figure 10B:

In situ hybridization for NL8 showed highly organized expression pattern in the developing limb, intestine and body wall, suggesting a distinctive functional role at this site, and potential involvement in angiogenesis and patterning (FIGS. 10-A and 10-B). This expression pattern is distinct from that of NL1 and NL5.

In situ hybridization for NL4 showed apparent expression over small vessels in the deep white matter of rhesus monkey brain.

EXAMPLE 5
Expression of NL1, NL5, NL8, and NL4 in *E. coli*

This example illustrates the preparation of an unglycosylated form of the TIE ligands of the present invention in *E. coli*. The DNA sequence encoding a NL1, NL5, NL8, or NL4 ligand (SEQ. ID. NOs: 1, 3, 5, and 18, respectively) is initially amplified using selected PCR primers. The primers should contain restriction enzyme sites which correspond to the restriction enzyme sites on the selected expression vector. A variety of expression vectors may be employed. The vector will preferably encode an antibiotic resistance gene, an origin of replication, e promoter, and a ribozyme binding site. An example of a suitable vector is pBR322 (derived from *E. coli*; see Bolivar et al., *Gene* 2:95 (1977)) which contains genes for ampicillin and tetracycline resistance. The vector is digested with restriction enzyme and dephosphorylated. The PCR amplified sequences are then ligated into the vector.

The ligation mixture is then used to transform a selected *E. coli* strain, using the methods described in Sambrook et al., supra. Transformants are identified by their ability to grow on LB plates and antibiotic resistant colonies are then selected. Plasmid DNA can be isolated and confirmed by restriction analysis.

Selected clones can be grown overnight in liquid culture medium such as 1B broth supplemented with antibiotics. The overnight culture may subsequently be used to inoculate a later scale culture. The cells are then grown to a desired optical density. An inducer, such as IPTG may be added.

After culturing the cells for several more hours, the cells can be harvested by centrifugation. The cell pellet obtained by the centrifugation can be solubilized using various agents known in the art, and the solubilized protein can then be purified using a metal chelating column under conditions that allow tight binding of the protein.

EXAMPLE 6
Expression of NL1, NL5, NL8, and NL4 in Mammalian Cells

This example illustrates preparation of a glycosylated form of the NL1, NL5, NL8, and NL4 TIE ligand homologues by recombinant expression in mammalian cells.

The vector, pRK5 (see EP 307,247, published Mar. 15, 1989), is employed as the expression vector. Optionally, the NL1, NL5, NL8, or NL4 DNA is ligated into pRK5 with selected restriction enzymes to allow insertion of the NL1, NL5, NL8, and NL4 DNA using ligation methods such as described in Sambrook et al., supra. The resulting vector is called pRK5-NL1, NL5, NL8, and NL4, respectively.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 µg pRK5-NL1, NL5, NL4, or NL8 DNA is mixed with about 1 µg DNA encoding the VA RNA gene [Thimmappaya et al., *Cell*, 31:543 (1982)] and dissolved in 500 µl of 1 mM Tris-HCl, 0.1 mM EDTA, 0.227 M $CaCl_2$. To this mixture is added, dropwise, 500 µl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 µCi/ml $^{35}$S-cysine and 200 µCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of NL1, NL5 and NL8 polypeptide. The cultures containing transfected cells may undergo further incubation (in serum free medium) and the medium is tested in selected bioassays.

In an alternative technique, NL1, NL5, NL8, or NL4 DNA may be introduced into 293 cells transiently using the dextran sulfate method described by Somparyrac et al., *Proc. Natl. Acad. Sci.*, 12:7575 (1981). 293 cells are grown to maximal density in a spinner flask and 700 µg pRK5-NL1, NL5, NL8, or NL4 DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing expressed NL1, NL5, NL8, or NL4 can then be concentrated and purified by any selected method, such as dialysis and/or column chromatography.

In another embodiment, NL1, NL5, NL8, or NL4 can be expressed in CHO cells. The pRK5-NL1, NL5, NL8, or NL4 can be transfected into CHO cells using known reagents such as CaPO₄ or DEAE-dextran. As described above, the cell cultures can be incubated, and the medium replaced with culture medium (alone) or medium containing a radiolabel such as $^{35}$S-methionine. After determining the presence of the expressed polypeptide, the culture medium may be replaced with serum free medium. Preferably, the cultures are incubated for about 6 days, and then the conditioned medium is harvested. The medium containing the expressed NL1, NL5, NL8, or NL4 can then be concentrated and purified by any selected method.

Epitope-tagged NL1, NL5, NL8, or NL4 may also be expressed in host CHO cells. NL1, NL5, NL8, or NL4 DNA may be subcloned out of the pRK5 vector. The subclone insert can undergo PCR to fuse in frame with a selected epitope tag such as a poly-his tag into a Baculovirus expression vector. The poly-his tagged NL1, NL5, NL8, or NL4 insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged NL1, NL5, NL8, or NL4 can then be concentrated and purified by any selected method, such as by $Ni^{2+}$-chelate affinity chromatography.

Glycosylated forms of NL1, NL5 and NL8 were indeed expressed in mammalian cells. NL1 was expressed as an IgG construct (NL1-IgG immunoadhesin), in which the NL1 protein extracellular region was fused to an IgG1 constant region sequence containing the hinge, CH2 and CH3 domains. NL5 and NL8 were expressed in a poly-His tagged forms.

Following PCR amplification, the NL1 DNA was subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used for the expression of NL1 in CHO cells is as described in Lucas et al., *Nucl. Acids Res.* 24:9 (1774–1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of NL1-encoding plasmid DNA were introduced into approximately 10 million CHO cells using commercially available transfection reagents Superfect® (Quiagen), Dosper® or Fugene® (Boehringer Mannheim). The cells were grown and described in Lucas et al, supra Approximately $3 \times 10^{-7}$ cells were frozen in an ampoule for further growth and production as described below.

The ampoule containing NL1 plasmid DNA was thawed by placement into water bath and mixed by vortexing. The contents were pipetted into a centrifuge tube containing 10 mLs of medium and centrifuged at 1000 rpm for 5 minutes. The supernatant was aspirated and the cells were resuspended in 10 mL of selective medium (0.2 μm filtered PS20 with 5% 0.2 μm diafiltered fetal bovine serum). The cells were then aliquoted into a 100 mL spinner containing 90 mL of selective medium. After 1–2 days, the cells were transferred into a 250 mL spinner filled with 150 mL selective growth medium and incubated at 37° C. After another 2–3 days, a 250 mL, 500 mL and 2000 mL spinners were seeded with $3 \times 10^5$ cells/mL. The was exchanged with fresh medium by centrifugation and resuspension in production medium. Any suitable CHO medium may be employed, e.g., such as is described in U.S. Pat. No. 5,122,469, issued Jun. 16, 1992. A 3 L production spinner is seeded at $1.2 \times 10^6$ cells/mL. On day 0, the cell number and pH were determined. On day 1, the spinner was sampled and sparging with filtered air was commenced. On day 2, the spinner was sampled, the temperature shifted to 33° C., and 30 mL of 500 g/L-glucose and 0.6 mL of 10% antifoam (e.g., 35% polydimethylsiloxaneemulsion, Dow Corning 365 Medical Grade Emulsion) were added. Throughout the production, pH was adjusted as necessary to keep at around 7.2. After 10 days, or until viability dropped below 70%, the cell culture was harvested by centrifugation and filtered through a 0.22 μm filter. The filtrate was either stored at 4° C. until loading onto a purification column.

The NL1-IgG immunoadhesin was purified from the conditioned medium as follows. The conditioned medium was pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275 μL of 1 M Tris buffer, pH 9. The highly purified protein was subsequently desalted into storage buffer containing 10 mM Hepes, 0.14 M NaCl and 4% mannitol, pH 6.8, with a 25 ml G25 Superfine (Pharmacia) column and stored at −80° C.

The homogeneity of the purified NL1-IgG protein was verified by SDS polyacrylamide gel electrophoresis (SDS PEG) and N-terminal amino acid sequencing performed by Edman degradation. The protein was found to have a molecular weight of about 37–38 kD.

The expression of NL5 and NL8 was performed essentially as herein above described. For these poly-His tagged constructs purification was performed using a Ni-NTA column (Qiagen). Before purification, imidazole was added to the conditioned medium to a concentration of 5 mM. The conditioned medium was pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column was washed with additional equilibration buffer and the protein eluted with equilibration buffer containing 0.25 M imidazole. The purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

The homogeneity of the purified protein was confirmed by SDS PEG and N-terminal amino acid sequencing performed by Edman degradation.

EXAMPLE 7

Expression of NL1, NL5, NL8 and NL4 in Yeast

First, yeast expression vectors are constructed for intracellular production or secretion of NL1, NL5, NL8 or NL4 from the ADH2/GAPDH promoter. DNA encoding NL1, NL5, NL8 or NL4, a selected signal peptide and the promoter is inserted into suitable restriction enzyme sites in the selected plasmid to direct intracellular expression of NL1, NL5, NL8 or NL4. For secretion, DNA encoding NL1, NL5, NL8 or NL4 can be cloned into the selected plasmid, together with DNA encoding the ADH2/GAPDH promoter, the yeast alpha-factor secretory signal/leader sequence, and linker sequences (if needed) for expression of NL1, NL5, NL8 or NL4.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant NL1, NL5, NL8 and NL4 can subsequently be isolated and purified by removing the yeast cells from the fermentation medium by centrifugation and then concentrating the medium using selected cartridge filters. The concentrate containing NL1, NL5, NL8 or NL4 may further be purified using selected column chromatography resins.

EXAMPLE 8

Expression of NL1, NL2, NL8 and NL4 in Baculovirus Expression System

The following method describes recombinant expression of NL1, NL5, NL8 or NL4 in Baculovirus expression system.

The NL1, NL5, NL8 or NL4 is fused upstream of an epitope tag contained with a baculovirus expression vector. Such epitope tags include poly-his tags and immunoglobulin tags (like Fc regions of IgG). A variety of plasmids may be employed, including plasmids derived from commercially available plasmids such as pVL1393 (Novagen). Briefly, the DNA encoding NL1, NL5, NL8 or NL4 or the desired portion of the NL1, NL5, NL8 or NL4 (such as the sequence encoding the extracellular domain of a transmembrane protein) is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4–5 days of incubation at 28° C., the released viruses are harvested and used for further amplifications. Viral infection and protein expression is performed as described by O'Reilley et al., Baculovirus expression vectors: A laboratory Manual, Oxford: Oxford University Press (1994).

Expressed poly-his tagged NL1, NL5, NL8 or NL4 can then be purified, for example, by $Ni^{2+}$-chelate affinity chromatography as follows. Extracts are prepared from recombinant virus-infected Sf9 cells as described by Rupert et al., *Nature,* 362:175–179 (1993). Briefly, Sf9 cells are washed, resuspended in sonication buffer (25 mL Hepes, pH 7.9; 12.5 mM $MgCl_2$; 0.1 mM EDTA; 10% Glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% Glycerol, pH 7.8) and filtered through a 0.45 μm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% Glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or western blot with $Ni^{2+}$-NTA-conjugated to alkaline phosphatase (Qiagen). Fractions containing the eluted $His_{10}$-tagged NL1, NL5 and NL8 are pooled and dialyzed against loading buffer.

Alternatively, purification of the IgG tagged (or Fc tagged) NL1, NL5 and NL8 can be performed using known chromatography techniques, including for instance, Protein A or protein G column chromatography.

NL1, NL5 and NL8 were expressed in Baculovirus-infected Sf9 cells. While the expression was actually performed in a 0.5–2 L scale, it can be readily scaled up for larger (e.g. 8 L) preparations. NL1 was expressed as an IgG construct (NL1-IgG immunoadhesin), in which the NL1 protein extracellular region was fused to an IgG1 constant region sequence containing the hinge, CH2 and CH3 domains. NL5 and NL8 were also expressed in poly-His tagged forms.

Following PCR amplification of the respective coding sequences were subcloned into a baculovirus expression vector (pb.PH.IgG for IgG fusions and pb.PH.His.c for poly-His tagged proteins), and the vector and Baculogold® baculovirus DNA (Pharmingen) were co-transfected into 105 *Spodoptera frugiperda* ("Sf9") cells (ATCC CRL 1711), using Lipofectin (Gibco BRL). pb.PH.IgG and pb.PH.His are modifications of the commercially available baculovirus expression vector pVL1393 (Pharmingen), with modified polylinker regions to include the His or Fc tag sequences. The cells were grown in Hink's TNM-FH medium supplemented with 10% FBS (Hyclone). Cells were incubated for 5 days at 28° C. The supernatant was harvested and subsequently used for the first viral amplification by infecting Sf9 cells in Hink's TNM-FH medium supplemented with 10% FBS at an approximate multiplicity of infection (MOI) of 10. Cells were incubated for 3 days at 28° C. The supernatant was harvested and the expression of the NL1, NL5 and NL8 constructs in the baculovirus expression vector was determined by batch binding of 1 ml of supernatant to 25 mL of Ni-NTA beads (QIAGEN) for histidine tagged proteins or Protein-A Sepharose CL-4B beads (Pharmacia) for IgG tagged proteins followed by SDS-PAGE analysis comparing to a known concentration of protein standard by Coomassie blue staining.

The first viral amplification supernatant was used to infect a spinner culture (500 ml) of Sf9 cells grown in ESF-921 medium (Expression Systems LLC) at an approximate MOI of 0.1. Cells were incubated for 3 days at 28° C. The supernatant was harvested and filtered. Batch binding and SDS-PAGE analysis was repeated, as necessary, until expression of the spinner culture was confirmed.

The conditioned medium from the transfected cells (0.5 to 3 L) was harvested by centrifugation to remove the cells and filtered through 0.22 micron filters. For the poly-His tagged constructs, the protein construct were purified using a Ni-NTA column (Qiagen). Before purification, imidazole was added to the conditioned media to a concentration of 5 mM. The conditioned media were pumped onto a 6 ml Ni-NTA column equilibrated in 20 mM Hepes, pH 7.4, buffer containing 0.3 M NaCl and 5 mM imidazole at a flow rate of 4–5 ml/min. at 4° C. After loading, the column was washed with additional equilibration buffer and the protein eluted with equilibration buffer containing 0.25 M imidazole. The highly purified protein was subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc containing) constructs of proteins were purified from the conditioned media as follows. The conditioned media were pumped onto a 5 ml Protein A column (Pharmacia) which had been equilibrated in 20 mM Na phosphate buffer, pH 6.8. After loading, the column was washed extensively with equilibration buffer before elution with 100 mM citric acid, pH 3.5. The eluted protein was immediately neutralized by collecting 1 ml fractions into tubes containing 275 mL of 1 M Tris buffer, pH 9. The highly purified protein was subsequently desalted into storage buffer as described above for the poly-His tagged proteins. The homogeneity of the NL1, NL5 and NL8 proteins was verified by SDS polyacrylamide gel (PEG) electrophoresis and N-terminal amino acid sequencing by Edman degradation.

EXAMPLE 9
Preparation of Antibodies that Bind NL1, NL2, NL8 or NL4

This example illustrates preparation of monoclonal antibodies which can specifically bind NL1, NL2, NL8 or NL4.

Techniques for producing the monoclonal antibodies are known in the art and are described, for example, in Goding, supra. Immunogens that may be employed include purified ligands of the present invention, fusion proteins containing such ligands, and cells expressing recombinant ligands on the cell surface. Selection of the immunogen can be made by the skilled artisan without undue experimentation.

Mice, such as Balb/c, are immunized with the immunogen emulsified in complete Freund's adjuvant and injected subcutaneously or intraperitoneally in an amount from 1–100 micrograms. Alternatively, the immunogen is emulsified in MPL-TDM adjuvant (Ribi Immunochemical Research, Hamilton, Mont.) and injected into the animal's hind food pads. The immunized mice are then boosted 10 to 12 days later with additional immunogen emulsified in the selected adjuvant Thereafter, for several weeks, the mice might also be boosted with additional immunization injections. Serum samples may be periodically obtained from the mice by retro-orbital bleeding for testing ELISA assays to detect the antibodies.

After a suitable antibody titer has been detected, the animals "positive" for antibodies can be injected with a final intravenous injection of the given ligand. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, mycloma hybrids, and spleen cell hybrids.

The hybridoma cells will be screened in an ELISA for reactivity against the antigen. Determination of "positive" hybridoma cells secreting the desired monoclonal antibodies against the TIE ligand homologues herein is well within the skill in the art.

The positive hybridoma cells can be injected intraperitoneal into syngeneic Balb/c mice to produce ascites containing the anti-TIE-ligand homologue monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

EXAMPLE 10
Inhibition of VEGF Stimulated Endothelial Cell Proliferation

Bovine adrenal cortical capillary endothelial (ACE) cells (from primary culture, maximum 12–14 passages) were plated on 96-well microtiter plates (Amersham Life Science) at a density of 500 cells/well per 100 μL in low glucose DMEM, 10% calf serum, 2 mM glutamine, 1×pen/strept and fungizone, supplemented with 3 ng/mL VEGF. Controls were plated the same way but some did not include VEGF. Test samples of the NL8 polypeptide were added in a 100 μl volume for a 200 mcL final volume. Cells were incubated for 6–7 days at 37° C. The medium was aspirated and the cells washed 1× with PBS. An acid phosphatase reaction mixture (100 μL, 0.1M sodium acetate, pH 5.5, 0.1% Triton-100, 10 mM p-nitrophenyl phosphate) was added. After incubation for 2 hours at 37° C., the reaction was stopped by addition of 10 mcL 1N NaOH. OD was measured on microtiter plate reader at 405 nm. Controls were no cells, cells alone, cells+FGF (5 ng/mL), cells+VEGF (3 ng/mL), cells+VEGF (3 ng/ml)+TGF-β (1 ng/ml), and cells+VEGF (3 ng/mL)+LIF (5 ng/mL). (TGF-β at a 1 ng/ml concentration is known to block 70–90% of VEGF stimulated cell proliferation.)

The results were assessed by calculating the percentage inhibition of VEGF (3 ng/ml) stimulated cell proliferation, determined by measuring acid phosphatase activity at OD405 nm, (1) relative to cells without stimulation, and (2) relative to the reference TGF-β inhibition of VEGF stimulated activity. The results are considered positive, if the inhibition is 30% or greater. NL5, tested in poly-His tagged form, significantly inhibited VEGF stimulated endothelial cell proliferation. These results are indicative of the utility of the NL5, and possibly related polypeptides, in cancer therapy and specifically in inhibiting tumor angiogenesis.

EXAMPLE 11
Induction of Endothelial Cell Apoptosis

The ability of the NL5 (poly-His tagged form) to induce apoptosis in endothelial cells was tested in human venous umbilical vein endothelial cells (HUVEC, Cell Systems), using a 96-well format, in 0% serum medium supplemented with 100 ng/ml VEGF. (As HUVEC cells are easily dislodged from the plating surface, all pipetting in the wells must be done as gently as practicable.)

The medium was aspired and the cells washed once with PBS. 5 ml of 1×trypsin was added to the cells in a T-175 flask, and the cells were allowed to stand until they were released from the plate (about 5–10 minutes). Trypsinization was stopped by adding 5 ml of growth media. The cells were spun at 1000 rpm for 5 minutes at 4° C. The medium was aspirated and the cells were resuspended in 10 ml of 10% serum complemented medium (Cell Systems), 1×penn/strep.

The cells were plated on 96-well microtiter plates (Amersham Life Science, cytostar-T scintillating microplate, RPNQ160, sterile, tissue-culturetreated, individually wrapped), in 10% serum (CSG-medium, Cell Systems), at a density of $2 \times 10^4$ cells per well in a total volume of 100 μl. The NL5 and NL8 polypeptides were added in triplicate at dilutions of 1%, 0.33% and 0.11%. Wells without cells were used as a blank and wells with cells only as a negative control. As a positive control 1:3 serial dilutions of 50 μl of a 3×stock of staurosporine were used. The ability of the NL5 polypeptide to induce apoptosis was determined using Annexin V, a member of the calcium and phospholipid binding proteins, to detect apoptosis.

0.2 ml Annexin V-Biotin stock solution (100 μg/ml) were diluted in 4.6 ml 2×$Ca^{2+}$ binding buffer and 2.5% BSA (1:25 dilution). 50 μls of the diluted Annexin V-Biotin solution were added to each well (except controls) to a final concentration of 1.0 μg/ml. The samples were incubated for 10–15 minutes with Annexin-Biotin prior to direct addition of $^{35}$S-Streptavidin. $^{35}$S-Streptavidin was diluted in 2×$Ca^{2+}$ Binding buffer, 2.5% BSA and was added to all wells at a final concentration of $3 \times 10^4$ cpm/well. The plates were then sealed, centrifuged at 1000 rpm for 15 minutes and placed on orbital shaker for 2 hours. The analysis was performed on 1450 Microbeta Trilux (Wallac).

NL5 was positive in this assay. This result further confirms the potential utility of this, and potentially related, molecules in cancer therapy.

EXAMPLE 12
Stimulation or Inhibition of Mixed Lymphocyte Reaction (MLR)

The Mixed Lymphocyte Reaction (MLR) assay evaluates CD4+ T lymphocyte function, more specifically, the ability of T lymphocytes to proliferate in response to the presentation of allo-antigen. In the one-way MLR assay, a donor population of peripheral blood mononuclear cells (PBMCs) is challenged with an irradiated stimulator population of PBMCs. The antigen to which the T lymphocytes respond is a mismatched MHC molecule that is expressed and presented by antigen presenting cells in the stimulator population. The assay identifies molecules which either enhance or inhibit the proliferation of the responder T lymphocyte in response to stimulation with presented allo-antigen.

Molecules that enhance (stimulate) MLR response enhance or potentiate the immune response to the antigen. Accordingly, such molecules (or small molecule or antibody agonists of such molecules) are candidates for the treatment of conditions where the enhancement of the immune response would be beneficial. In addition, inhibitors of such stimulatory molecules may be useful where suppression of the immune response would be of value. For example, using neutralizing antibodies or small molecule antagonists that inhibit the molecules with stimulatory activity in the MLR could be beneficial in the treatment of immune-mediated inflammatory diseases. Molecules that inhibit the MLR (or their small molecule or antibody agonists) could be useful in inhibiting the immune response and that ameliorating immune-mediated diseases.

In the present experiment, frozen PBMCs were thawed and cultured in RPMI+10% FBS the night before wash. The cells were resuspended in RPMI+10% FBS at a concentration of $3 \times 10^6$ cells/ml. 100 µl of the cell suspension were incubated with 100 µl of a test sample of NL5 and NL4 at 37° C., 5% CO. On the fifth day, the cells were pulsed for six hours then harvested.

NL5 was found to inhibit lymphocyte proliferation, while NL4 stimulated lymphocyte proliferation in this assay.

EXAMPLE 13
Gene Amplification Assay

This example shows that the NL8-encoding gene is amplified in the genome of certain human cancers. Amplification is associated with overexpression of the gene product, indicating that the NL8 protein is a useful target for therapeutic intervention in certain cancers such as lung, and potentially other, such as colon, breast and/or prostate cancers. Therapeutic agents may take the form of antagonists of NL8-encoding genes, for example, murine-human chimeric, humanized or human antibodies against NL8, or small molecule or peptide antagonists of the native polypeptide.

The starting material for the screen was genomic DNA isolated from a variety cancers. The DNA is quantitated precisely, e.g fluorometrically. As a negative control, DNA was isolated from the cells of ten normal healthy individuals which was pooled and used as assay controls for the gene copy in healthy individuals (not shown). The 5' nuclease assay (for example, TaqMan™) and real-time quantitative PCR (for example, ABI Prizm 7700 Sequence Detection System™ (Perkin Elmer, Applied Biosystems Division, Foster City, Calif.)), were used to find genes potentially amplified in certain cancers. The results were used to determine whether the DNA encoding NL8 was over-represented in any of the primary lung cancers that were screened. The results are reported in delta (Δ) CT units. One unit corresponds 1 PCR cycle or approximately a 2-fold amplification relative to normal, two units corresponds to 4-fold, 3 units to 8-fold amplification, and so on. Quantitation was obtained using primers and a Taqman™ fluorescent derived from the NL8-encoding gene. Regions of NL8 gene which are most likely to contain unique nucleic acid sequences and which are least likely to have spliced out introns are preferred for the primer derivation, e.g. 3-untranslated region. The sequences for the primers and probes (forward, reverse and probe) used for the NL8 were as follows:

```
                                    (SEQ ID NO: 33)
    23339.tm.5      G TCAGCAGGAG CCCAAGTTG
                                    (SEQ ID NO: 34)
    23339.tm.3      ACG GTTACACAGG GTGTCTT
                                    (SEQ ID NO: 35)
    23339.tm.p      TCTGGCCACACCTTCTTTGT GGCTC
```

The 5' nuclease assay reaction is a fluorescent PCR-based technique which makes use of the 5' exonuclease activity of Taq DNA polymerase enzyme to monitor amplification in real time. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the TAQ DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

The 5' nuclease procedure is run on a real-time quantitative PCR device such as the ABI Prism 7700TM Sequence Detection. The system consists of a thermocycler, laser, charge-coupled device (CCD) camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5' Nuclease assay data are initially expressed as Ct, or the threshold cycle. This is defined as the cycle at which the reporter signal accumulates above the background level of fluorescence. The ΔCt values are used as quantitative measurement of the relative number of starting copies of a particular target sequence in a nucleic acid sample.

Protocols

DNA Preparation

DNA was prepared from primary tumors and normal human blood (controls). The isolation was performed using purification kit #13362 (which includes 10 purification tips with a capacity of 400 µg genomic DNA each), buffer set #1960 and protease #19155 and #19101 all from Quiagen, according to the manufacturer's instructions and the description below.

Cell Culture Lysis

Cells were washed and trypsinized at a concentration of $7.5 \times 10^8$ per tip and pelleted by centrifuging at 1000 rpm for 5 minutes at 4° C., followed by washing again with 1/2 volume of PBS recentrifugation. The pellets were washed a third time, the suspended cells collected and washed 2× with PBS. The cells were then suspended into 10 mL PBS. Buffer C1 was equilibrated at 4° C. Quiagen protease #19155 was diluted into 6.25 ml cold ddH$_2$O to a final concentration of 20 mg/ml and equilibrated at 4° C. 10 mL of G2 Buffer was prepared by diluting Quiagen RNAse A stock (100 mg/ml) to a final concentration of 200 µg/ml.

Buffer C1 (10 mL, 4° C.) and ddH2O (40 mL, 4° C.) were then added to the 10 mL of cell suspension, mixed by inverting and incubated on ice for 10 minutes. The cell nuclei were pelleted by centrifuging in a Beckman swinging bucket rotor at 2500 rpm at 4° C. for 15 minutes. The supernatant was discarded and the nuclei were suspended with a vortex into 2 mL Buffer C1 (at 4° C.) and 6 mL ddH$_2$O, followed by a second 4° C. centrifugation at 2500 rpm for 15 minutes. The nuclei were then resuspended into the residual buffer using 200 µl per tip. G2 buffer (10 ml) was added to the suspended nuclei while gentle vortexing was applied. Upon completion of buffer addition, vigorous vortexing was applied for 30 seconds. Quiagen protease (200 µl, prepared as indicated above) was added and incubated at 50° C. for 60 minutes. The incubation and centrifugation was repeated until the lysates were clear (e.g., incubating additional 30–60 minutes, pelleting at 3000×g for 10 min., 4° C.).

Solid Human Tumor Sample Preparation and Lysis

Tumor samples were weighed and placed into 50 ml conical tubes and held on ice. Processing was limited to no more than 250 mg tissue per preparation (1 tip/preparation). The protease solution was freshly prepared by diluting into 6.25 ml cold ddH$_2$O to a final concentration of 20 mg/ml and stored at 4° C. G2 buffer (20 ml) was prepared by diluting DNAse A to a final concentration of 200 mg/ml (from 100 mg/ml stock). The tumor tissue was homogenated in 19 ml G2 buffer for 60 seconds using the large tip of the polytron in a laminar-flow TC hood to order to avoid inhalation of aerosols, and held at room temperature. Between samples, the polytron was cleaned by spinning at 2×30 seconds each in 2L ddH$_2$O, followed by G2 buffer (50 ml). If tissue was still present on the generator tip, the apparatus was disassembled and cleaned.

Quiagen protease prepared as indicated above, 1.0 ml) was added, followed by vortexing and incubation at 50° C. for 3 hours. The incubation and centrifugation was repeated until the lysates were clear (e.g., incubating additional 30–60 minutes, pelleting at 3000×g for 10 min., 4° C.).

Human Blood Preparation and Lysis

Blood is drawn from healthy volunteers using standard infectious agent protocols and citrated into 10 ml samples per tip. Quiagen protease was freshly prepared by dilution into 6.25 ml cold ddH$_2$O to a final concentration of 20 mg/ml and stored at 4° C. G2 buffer was prepared by diluting RNAse A to a final concentration of 200 µg/ml from 100 mg/ml stock. The blood (10 ml) was placed into a 50 ml conical tube and 10 ml C1 buffer and 30 ml ddH$_2$O (both previously equilibrated to 4° C.) were added, and the components mixed by inverting and held on ice for 10 minutes. The nuclei were pelleted with a Beckman swinging bucket rotor at 2500 rpm, 4° C. for 15 minutes and the supernatant discarded. With a vortex, the nuclei were suspended into 2 ml C1 buffer (4° C.) and 6 ml ddH$_2$O (4° C.). Vortexing was repeated until the pellet white. The nuclei were then suspended into the residual buffer using a 200 µl tip. G2 buffer (10 ml) were added to the suspended nuclei while gently vortexing, followed by vigorous vortexing for 30 seconds. Quiagen protease was added (200 µl) and incubated at 50° C. for 60 minutes. The incubation and centrifugation was repeated until the lysates were clear (e.g. incubating additional 30–60 minutes, pelleting at 3000×g for 10 min., 4° C.).

Purification of Cleared Lysates

Genomic DNA was equilibrated (1 sample per maxi tip preparation) with 10 ml QBT buffer. QF elution buffer was equilibrated at 50° C. The samples were vortexed for 30 seconds, then loaded onto equilibrated tips and drained by gravity. The tips were washed with 2×15 ml QC buffer. The DNA was eluted into 30 ml silanized, autoclaved 30 ml Corex tubes with 15 ml QF buffer (50° C). Isopropanol (10.5 ml) was added to each sample, the tubes covered with parafin and mixed by repeated inversion until the DNA precipitated. Samples were pelleted by centrifugation in the SS-34 rotor at 15,000 rpm for 10 minutes at 4° C. The pellet location was marked, the supernatant discarded, and 10 ml 70% ethanol (4° C.) was added. Samples were pelleted again by centrifugation on the SS-34 rotor at 10,000 rpm for 10 minutes at 4° C. The pellet location was marked and the supernatent discarded. The tubes were then placed on their side in a drying rack and dried 10 minutes at 37° C., taking care not to overdry the samples.

After drying, the pellets were dissolved into 1.0 ml TE (pH 8.5) and placed at 50° C. for 1–2 hours. Samples were held overnight at 4° C. as dissolution continued. The DNA solution was then transferred to 1.5 ml tubes with a 26 gauge needle on a tuberculin syringe. The transfer was repeated 5× in order to shear the DNA. Samples were then placed at 50° C. for 1–2 hours.

Quantitation of Genomic DNA and Preparation for Gene Amplification Assay

The DNA levels in each tube were quantified by standard A260, A280 spectrophotometry on a 1:20 dilution (5 µl DNA+95 µl ddH$_2$O) using the 0.1 ml quartz cuvettes in the Beckman DU640 spectrophotometer. A260/A280 ratios were in the range of 1.8–1.9. Each DNA samples was then diluted further to approximately 200 ng/ml in TE (pH 8.5). If the original material was highly concentrated (700 ng/µl), the material was placed at 50° C. for 1–2 hours.

Fluorometric DNA quantitation was then performed on the diluted material (20–600 ng/ml) using the manufacturer's guidelines as modified below. This was accomplished by allowing a Hoeffer DyNA Quant 200 fluorometer to warm-up for about 15 minutes. The Hoechst dye working solution (#H33258, 10 µl, prepared within 12 hours of use) was diluted into 100 ml 1×TNE buffer. A 2 ml cuvette is filled with the fluorometer solution, placed into the machine, and the machine is zeroed. pGEM 3Zf(+) (2 µl, lot #360851026) was added to 2 ml of fluorometer solution and calibrated at 200 units. A second 2 µl of pGEM 3Zf(+) DNA was then tested and the reading confirmed at 400 +/−10 units. Each sample was then read at least in triplicate. When 3 samples were found to be within 10% of each other, their average was taken and this value was used as the quantification value.

The fluorometricly determined concentration was then used to dilute each sample to 10 ng/µl in ddH$_2$O. This was done simultaneously on all template samples for a single TaqMan plate assay, and with enough material to run 500–1000 assays. The samples were tested in triplicate with both B-actin and GAPDH on a single plate with normal human DNA and no-template controls. The diluted samples were used provided that the CT value of normal human DNA subtracted from test DNA was +/−1 CT. The diluted, lot-qualified genomic DNA was stored in 1.0 ml aliquots at −80°

C. Aliquots which were subsequently to be used in the gene amplification assay were stored at 4° C. Each 1 ml aliquot is enough for 8–9 plates or 64 tests.

Gene Amplification Results

The results of the gene amplification assay are reported (as ΔCt values) in the following table:

TABLE

| Primary tumor | ΔCt |
|---|---|
| Human Lung SqCCa (LT1) | 0.58 |
| Human Lung NSCCa (LT1a) | 1.13 |
| Human Lung AdenoCa (LT2) | 0.13 |
| Human Lung AdenoCa (LT3) | 1.59 |
| Human Lung SqCCa (LT4) | 0.06 |
| Human Lung AdenoCa (LT6) | 0.88 |
| Human Lung Aden/SqCCa (LT7) | 0.77 |
| Human Lung AdenoCa (LT9) | 1.14 |
| Human Lung SqCCa (LT10) | 1.44 |
| Human Lung AdenoCa (LT11) | 2.05; 1.88; 2.25 |
| Human Lung AdenoCa (LT12) | 1.84 |
| Human Lung Bac (LT13) | 2.36; 1.88; 2.02 |
| Human Lung SqCCa (LT15) | 2.25; 1.97; 2.57 |
| Human Lung SqCCa (LT16) | 0.74; 0.85; 1.23 |
| Human Lung SqCCa (LT17) | 2.37; 2.04; 2.76 |
| Human Lung SqCCa (LT18) | −0.08; −0.38; −0.48 |
| Human Lung SqCCa (LT19) | 2.66; −13.56; 3.12 |
| Human Lung LCCa (LT21) | 0.86; 0.45; 1.44 |

Explanations of the abbreviations used in the Table have been provided hereinbefore.

A ΔCt value of >1 was typically used as the threshold value for amplification scoring, as this represents a doubling of the gene copy. The above Table indicates that significant amplification of the NL8 DNA occurred in a variety of primary lung tumors, indicating that this molecule is a valuable target for cancer therapy. In particular, antagonists (e.g., antibodies) directed against the NL8 protein would be expected to be useful in cancer therapy.

Further experiments are needed to determine whether amplification occurs in other (e.g. colon, breast, prostate, uterine, etc.) cancers and/or cancer cell lines. The observations can be refined and supplemented by framework and epicenter mapping and in further cell-based assays or animal models, as hereinbefore described.

EXAMPLE 14

Tumor Angiogenesis

This assay is based on the experimental finding that Chinese Hamster Ovary (CHO) cells transfected to express VEGF acquire the ability to form tumors in nude mice even though VEGF has no direct effect on the growth of CHO cells (Ferrara et al., *J. Clin. Invest.* 91:160 [1993]). Thus, normal CHO cells have adequate proliferative capacity but their ability to form tumors is limited by their inability to elicit angiogenesis. This assay seeks to determine whether other molecules can function like VEGF in making CHO cells tumorigenic. Inhibitors of such molecules could be useful in cancer therapy, as in the absence of vascular supply, diffusion of nutrients is known to limit the size of a tumorous nodule to about 1 mm in diameter.

CHO cells were stably transfected with a vector containing the genes encoding NL1 and NL8. CHO cells transfected with the same vector containing the coding sequence of VEGF or with an empty vector served as positive and negative controls. Cells were injected subcutaneously in the flank of female nude mice (1 million cells/mouse, 5 mice per transfectant). The injection site was checked weekly for the appearance of a tumor nodule. Histological evaluation was performed on any nodules that developed.

Tumor nodules were observed in mice carrying the NL1 and NL8 expressing CHO cells, indicating that NL1 and NL8, like VEGF, is capable of making CHO cells tumorigenic.

EXAMPLE 15

Stimulation of Endothelial Tube Formation

This assay follows the assay described in Davis and Camarillo, *Experimental Cell Research*, 2:39–51 (1996), or one modified from it as follows:

Protocol

HUVE cells (passage number less than 8 from primary) are mixed with type 1 rat tail collagen, final concentration 2.6 mg/ml at a density of $6 \times 10^5$ cells/ml and plated at 50 μl per well on a 96-well plate. The gel is allowed to solidify for 1 hr at 37° C., then 50 μl per well of M199 culture media supplemented with 1% FBS and an NL1 polypeptide sample (at dilutions of 1%, 0.1%, and 0.01%, respectively) is added along with 1 μM 6-FAM-FITC dye to stain vacuoles while they are forming. Cells are incubated at 37° C./5% $CO_2$ for 48 hr, fixed with 3.7% formalin at room temperature for 10 minutes, washed with PBS five times, then stained with Rh-Phalloidin at 4° C. overnight followed by nuclear staining with 4 μM DAPI.

1. Apoptosis Assay

This assay will identify factors that facilitate cell survival in a 3-dimensional matrix in the presence of exogenous growth factors (VEGF, bFGF without PMA).

A positive result is equal to or less than 1. 0=no apoptosis, 1=less than 20% cells are apoptotic, 2=less than 50% cells are apoptotic, 3=greater than 50% cells are apoptotic. Stimulators of apoptosis in this system are expected to be apoptotic factors, and inhibitors are expected to prevent or lessen apoptosis.

2. Vacuoles Assay

This assay will identify factors that stimulate endothelial vacuole formation and lumen formation in the presence of bFGF and VEGF (40 ng/ml).

A positive result is equal to or greater than 2. 1=vacuoles present in less than 20% of cells, 2=vacuoles present in 20–50% of cells, 3=vacuoles present in greater than 50% of cells. This assay is designed to identify factors that are involved in stimulating pinocytosis, ion pumping, permeability, and junction formation.

3. Tube Formation Assay

This assay is to identify factors that stimulate endothelial tube formation in a 3-dimensional matrix. This assay will identify factors that stimulate endothelial cells to differentiate into a tube-like structure in a 3-dimensional matrix in the presence of exogenous growth factors (VEGF, bFGF).

A positive result is equal to or greater than 2. 1=cells are all round, 2=cells are elongated, 3=cells are forming tubes with some connections, 4=cells are forming complex tubular networks. This assay would identify factors that may be involved in stimulating tracking, chemotaxis, or endothelial shape change.

Figure 17:
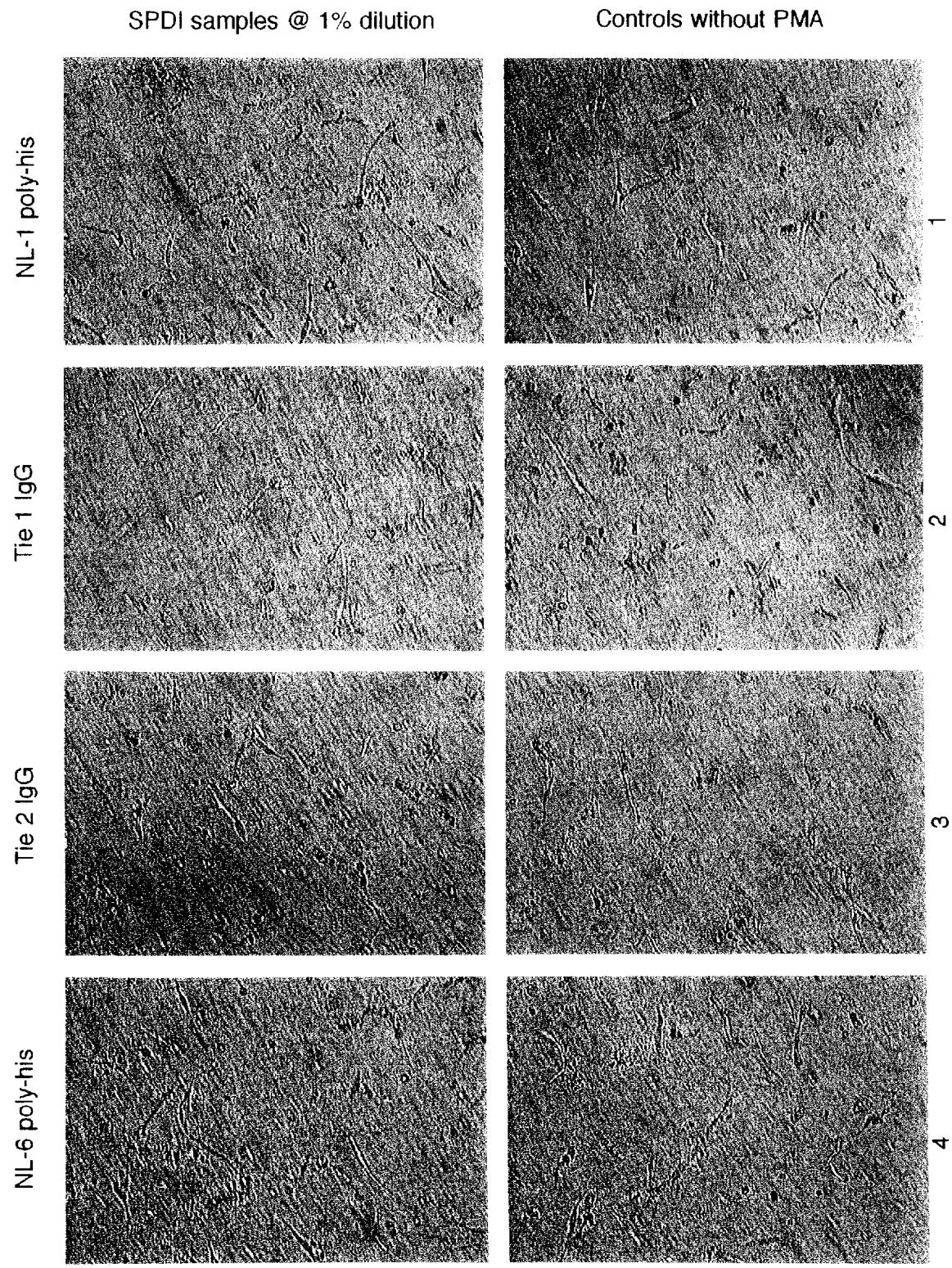
FIG. 17 shows the effect on HUVEC tube formation of the NL1 polypeptide conjugated to poly-his at 1% dilution and of a buffer control (10 mM HEPES/0.14M NaCl/4% mannitol, pH 6.8) at 1% dilution. Comparative results with another novel TIE ligand homologue (NL6) and two known TIE ligands TIE-1 and TIE-2, tested as IgG fusions, are also shown in the Figure.

FIG. 17 shows the effect on HUVEC tube formation of the NL1 polypeptide conjugated to poly-his at 1% dilution and of a buffer control (10 mM HEPES/0.14M NaCl/4% mannitol, pH 6.8) at 1% dilution Comparative results with another novel TIE ligand homologue (NL6) and two known TIE ligands TIE-1 and TIE-2, tested as IgG fusions, are also shown in the Figure.

Deposit of Material

As noted before, the following materials have been deposited with the American Type Culture Collection, 12301 Parklawn Drive, Rockville, Md., USA (ATCC):

| Material | ATCC Dep. No. | Deposit Date |
|---|---|---|
| NL1-DNA 22779-1130 | 209280 | September 18, 1997 |
| NL5-DNA 28497-1130 | 209279 | September 18, 1997 |
| NL8-DNA 23339-1130 | 209282 | September 18, 1997 |
| NL4-DNA 47470-1130P1 | 209422 | October 28, 1997 |

These deposits were made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of the deposit. The deposit will be made available by ATCC under the terms of the Budapest Treaty, and subject to an agreement between Genentech, Inc. and ATCC, which assures permanent and unrestricted availability of the progeny of the culture of the deposit to the public upon issuance of the petinent U.S. patent or upon laying open to the public of any U.S. or foreign patent application, whichever comes first, and assures availability of the progeny to one determined by the U.S. Commissioner of Patents and Trademarks to be entitled thereto according to 35 USC §122 and Commissioner's rules pursuant thereto (including 37 C.F.R. §1.14 with particular reference to 886 OG 683).

The assignee of the present application has agreed that if a culture of the materials on deposit should die ot be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

The present specification is considered to be sufficient to enable one skilled in the art to practice the invention. The present invention is not to be limited in scope by the construct deposited, since the deposited embodiment is intended as a single illustration of certain aspects of the invention and any constructs that are functionally equivalent are within the scope of the invention. The deposit of material herein does not constitute an admission that the written description is inadequate to enable the practice of any aspect of the invention, including the best more thereof, nor is it to be construed as limiting the scope of the claims to the specific illustrations that it represents. Indeed, various modifications of the invention in addition to those shown and described herein will become apparent to those skilled in the art from the foregoing description and fall within the scope of the appended claims.

What is claimed is:

1. An isolated TIE ligand homologue polypeptide comprising the amino acid sequence of:
   (1) a native human NL4 polypeptide of SEQ ID NO: 19; or
   (2) a polypeptide having at least about 90% sequence identity with the native human NL4 polypeptide of SEQ ID NO: 19, and having the ability to induce vascularization.

2. A composition comprising a polypeptide of claim 1 in association with a carrier.

3. A conjugate comprising a polypeptide of claim 1, fused to a therapeutic or cytotoxic agent.

4. The conjugate of claim 3 wherein the therapeutic agent is a toxin, a different TIE ligand homologue, or a member of the vascular endothelial growth factor (VEGF) family.

5. An isolated nucleic acid molecule comprising a nucleotide sequence encoding a TIE ligand homologue polypeptide which is:
   (1) a native NL4 polypeptide of SEQ ID NO: 19; or
   (2) a polypeptide having at least about 90% sequence identity with the native human NL4 polypeptide of SEQ ID NO: 19, and having the ability to induce vascularization.

6. The isolated nucleic acid molecule of claim 5 which comprises the coding region of SEQ ID NO: 18.

7. The isolated nucleic acid molecule of claim 5 which comprises the fibrinogen-like domain coding sequence of SEQ ID NO: 18.

8. A vector which comprises a nucleic acid molecule of any one of claims 5–7.

9. A recombinant host cell transformed with a nucleic acid molecule of any one of claims 5–7.

10. The recombinant host cell of claim 9 which is a prokaryotic cell.

11. The recombinant host cell of claim 9 which is an eukaryotic cell.

12. A vector which comprises the nucleic acid molecule of claim 5.

13. A recombinant host cell transformed with the vector of claim 12.

14. The recombinant host cell of claim 13 which is a prokaryotic cell.

15. The recombinant host cell of claim 13 which is a eukaryotic cell.

16. The isolated nucleic acid molecule of claim 5, wherein the NL4 polypeptide has at least 95% sequence identity to the amino acid sequence of SEQ ID NO: 19.

17. The isolated nucleic acid molecule of claim 5, wherein the NL4 polypeptide has at least 98% sequence identity to the amino acid sequence of SEQ ID NO: 19.

18. The isolated nucleic acid molecule of claim 5, wherein the NL4 polypeptide comprises the amino acid sequence of SEQ ID NO: 19.

* * * * *

SEQUENCE LISTING

```
<160> NUMBER OF SEQ ID NOS: 35

<210> SEQ ID NO 1
<211> LENGTH: 2290
<212> TYPE: DNA
<213> ORGANISM: Homo Sapiens

<400> SEQUENCE: 1
ggctgagggg aggcccggag cctttctggg gcctggggga tcctcttgca         50
ctggtgggtg gagagaagcg cctgcagcca accagggtca ggctgtgctc        100
acagtttcct ctggcggcat gtaaaggctc cacaaaggag ttgggagttc        150
aaatgaggct gctgcggacg gcctgaggat ggaccccaag ccctggacct        200
gccgagcgtg gcactgaggc agcggctgac gctactgtga gggaaagaag        250
gttgtgagca gccccgcagg accectggcc agccctggcc ccagcctctg        300
ccggagccct ctgtggaggc agagccagtg gagcccagtg aggcagggct        350
gcttggcagc caccggcctg caactcagga acccctccag aggccatgga        400
caggctgccc cgctgacggc cagggtgaag catgtgagga gccgccccgg        450
agccaagcag gagggaagag gctttcatag attctattca caaagaataa        500
ccaccatttt gcaaggacca tgaggccact gtgcgtgaca tgctggtggc        550
tcggactgct ggctgccatg ggagctgttg caggccagga ggacggtttt        600
gagggcactg aggagggctc gccaagagag ttcatttacc taaacaggta        650
caagcgggcg ggcgagtccc aggacaagtg cacctacacc ttcattgtgc        700
cccagcagcg ggtcacgggt gccatctgcg tcaactccaa ggagcctgag        750
gtgcttctgg agaaccgagt gcataagcag gagctagagc tgctcaacaa        800
tgagctgctc aagcagaagc ggcagatcga dacgctgcag cagctggtgg        850
```

-continued

| | |
|---|---|
| aggtggacgg cggcattgtg agcgaggtga agctgctgcg caaggagagc | 900 |
| cgcaacatga actcgcgggt cacgcagctc tacatgcagc tcctgcacga | 950 |
| gatcatccgc aagcgggaca acgcgttgga gctctcccag ctggagaaca | 1000 |
| ggatcctgaa ccagacagcc gacatgctgc agctggccag caagtacaag | 1050 |
| gacctggagc acaagtacca gcacctggcc acactggccc acaaccaatc | 1100 |
| agagatcatc gcgcagcttg aggagcactg ccagagggtg ccctcggcca | 1150 |
| ggcccgtccc ccagccaccc ccgctgccc cgccccgggt ctaccaacca | 1200 |
| cccacctaca accgcatcat caaccagatc tctaccaacg agatccagag | 1250 |
| tgaccagaac ctgaaggtgc tgccaccccc tctgccccact atgcccactc | 1300 |
| tcaccagcct cccatcttcc accgacaagc cgtcgggccc atggagagac | 1350 |
| tgcctgcagg ccctggagga tggccacgac accagctcca tctacctggt | 1400 |
| gaagccggag aacaccaacc gcctcatgca ggtgtggtgc gaccagagac | 1450 |
| acgaccccgg gggctggacc gtcatccaga gacgcctgga tggctctgtt | 1500 |
| aacttcttca ggaactggga gacgtacaag caagggtttg ggaacattga | 1550 |
| cggcgaatac tggctgggcc tggagaacat ttactggctg acgaaccaag | 1600 |
| gcaactacaa actcctggtg accatggagg actggtccgg ccgcaaagtc | 1650 |
| tttgcagaat acgccagttt ccgcctggaa cctgagagcg agtattataa | 1700 |
| gctgcggctg gggcgctacc atggcaatgc gggtgactcc tttacatggc | 1750 |
| acaacggcaa gcagttcacc accctggaca gagatcatga tgtctacaca | 1800 |
| ggaaactgtg cccactacca gaagggaggc tggtggtata cgcctgtgc | 1850 |
| ccactccaac ctcaacgggg tctggtaccg cggggggccat taccggagcc | 1900 |
| gctaccagga cggagtctac tgggctgagt tccgaggagg ctcttactca | 1950 |
| ctcaagaaag tggtgatgat gatccgaccg aaccccaaca ccttccacta | 2000 |
| agccagctcc ccctcctgac ctctcgtggc cattgccagg agcccaccct | 2050 |
| ggtcacgctg ccacagcac aaagaacaac tcctcaccag ttcatcctga | 2100 |
| ggctgggagg accgggatgc tggattctgt tttccgaagt cactgcagcg | 2150 |
| gatgatggaa ctgaatcgat acggtgtttt ctgtccctcc tactttcctt | 2200 |
| cacaccagac agcccctcat gtctccagga caggacagga ctacagacaa | 2250 |
| ctctttcttt aaataaatta agtctctaca ataaaaaaaa | 2290 |

<210> SEQ ID NO 2
<211> LENGTH: 493
<212> TYPE: PRT
<213> ORGANISM: Homo Sapiens

<400> SEQUENCE: 2

Met Arg Pro Leu Cys Val Thr Cys Trp Trp Leu Gly Leu Leu Ala
 1               5                  10                  15

Ala Met Gly Ala Val Ala Gly Gln Glu Asp Gly Phe Glu Gly Thr
                20                  25                  30

Glu Glu Gly Ser Pro Arg Glu Phe Ile Tyr Leu Asn Arg Tyr Lys
                35                  40                  45

Arg Ala Gly Glu Ser Gln Asp Lys Cys Thr Tyr Thr Phe Ile Val
                50                  55                  60

-continued

```
Pro Gln Gln Arg Val Thr Gly Ala Ile Cys Val Asn Ser Lys Glu
             65                  70                  75

Pro Glu Val Leu Leu Glu Asn Arg Val His Lys Gln Glu Leu Glu
             80                  85                  90

Leu Leu Asn Asn Glu Leu Leu Lys Gln Lys Arg Gln Ile Glu Thr
             95                 100                 105

Leu Gln Gln Leu Val Glu Val Asp Gly Gly Ile Val Ser Glu Val
            110                 115                 120

Lys Leu Leu Arg Lys Glu Ser Arg Asn Met Asn Ser Arg Val Thr
            125                 130                 135

Gln Leu Tyr Met Gln Leu Leu His Glu Ile Ile Arg Lys Arg Asp
            140                 145                 150

Asn Ala Leu Glu Leu Ser Gln Leu Glu Asn Arg Ile Leu Asn Gln
            155                 160                 165

Thr Ala Asp Met Leu Gln Leu Ala Ser Lys Tyr Lys Asp Leu Glu
            170                 175                 180

His Lys Tyr Gln His Leu Ala Thr Leu Ala His Asn Gln Ser Glu
            185                 190                 195

Ile Ile Ala Gln Leu Glu Glu His Cys Gln Arg Val Pro Ser Ala
            200                 205                 210

Arg Pro Val Pro Gln Pro Pro Ala Ala Pro Pro Arg Val Tyr
            215                 220                 225

Gln Pro Pro Thr Tyr Asn Arg Ile Ile Asn Gln Ile Ser Thr Asn
            230                 235                 240

Glu Ile Gln Ser Asp Gln Asn Leu Lys Val Leu Pro Pro Pro Leu
            245                 250                 255

Pro Thr Met Pro Thr Leu Thr Ser Leu Pro Ser Ser Thr Asp Lys
            260                 265                 270

Pro Ser Gly Pro Trp Arg Asp Cys Leu Gln Ala Leu Glu Asp Gly
            275                 280                 285

His Asp Thr Ser Ser Ile Tyr Leu Val Lys Pro Glu Asn Thr Asn
            290                 295                 300

Arg Leu Met Gln Val Trp Cys Asp Gln Arg His Asp Pro Gly Gly
            305                 310                 315

Trp Thr Val Ile Gln Arg Arg Leu Asp Gly Ser Val Asn Phe Phe
            320                 325                 330

Arg Asn Trp Glu Thr Tyr Lys Gln Gly Phe Gly Asn Ile Asp Gly
            335                 340                 345

Glu Tyr Trp Leu Gly Leu Glu Asn Ile Tyr Trp Leu Thr Asn Gln
            350                 355                 360

Gly Asn Tyr Lys Leu Leu Val Thr Met Glu Asp Trp Ser Gly Arg
            365                 370                 375

Lys Val Phe Ala Glu Tyr Ala Ser Phe Arg Leu Glu Pro Glu Ser
            380                 385                 390

Glu Tyr Tyr Lys Leu Arg Leu Gly Arg Tyr His Gly Asn Ala Gly
            395                 400                 405

Asp Ser Phe Thr Trp His Asn Gly Lys Gln Phe Thr Thr Leu Asp
            410                 415                 420

Arg Asp His Asp Val Tyr Thr Gly Asn Cys Ala His Tyr Gln Lys
            425                 430                 435

Gly Gly Trp Trp Tyr Asn Ala Cys Ala His Ser Asn Leu Asn Gly
            440                 445                 450
```

Val Trp Tyr Arg Gly Gly His Tyr Arg Ser Arg Tyr Gln Asp Gly
          455                 460                 465

Val Tyr Trp Ala Glu Phe Arg Gly Gly Ser Tyr Ser Leu Lys Lys
          470                 475                 480

Val Val Met Met Ile Arg Pro Asn Pro Asn Thr Phe His
          485                 490

<210> SEQ ID NO 3
<211> LENGTH: 3355
<212> TYPE: DNA
<213> ORGANISM: Homo Sapiens

<400> SEQUENCE: 3

| | | | | |
|---|---|---|---|---|
| gcagctggtt | actgcatttc | tccatgtggc | agacagagca | aagccacaac | 50 |
| gctttctctg | ctggattaaa | gacggcccac | agaccagaac | ttccactata | 100 |
| ctacttaaaa | ttacataggt | ggcttgtcaa | attcaattga | ttagtattgt | 150 |
| aaaaggaaaa | agaagttcct | tcttacagct | tggattcaac | ggtccaaaac | 200 |
| aaaaatgcag | ctgccattaa | agtctcagat | gaacaaactt | ctacactgat | 250 |
| ttttaaaatc | aagaataagg | gcagcaagtt | tctggattca | ctgaatcaac | 300 |
| agacacaaaa | agctggcaat | atagcaacta | tgaagagaaa | agctactaat | 350 |
| aaaattaacc | caacgcatag | aagactttt | tttctcttct | aaaaacaact | 400 |
| aagtaaagac | ttaaatttaa | acacatcatt | ttacaacctc | atttcaaaat | 450 |
| gaagactttt | acctggaccc | taggtgtgct | attcttccta | ctagtggaca | 500 |
| ctggacattg | cagaggtgga | caattcaaaa | ttaaaaaaat | aaaccagaga | 550 |
| agatacccte | gtgccacaga | tggtaaagag | gaagcaaaga | aatgtgcata | 600 |
| cacattcctg | gtacctgaac | aaagaataac | agggccaatc | tgtgtcaaca | 650 |
| ccaagggca | agatgcaagt | accattaaag | acatgatcac | caggatggac | 700 |
| cttgaaaacc | tgaaggatgt | gctctccagg | cagaagcggg | agatagatgt | 750 |
| tctgcaactg | gtggtggatg | tagatggaaa | cattgtgaat | gaggtaaagc | 800 |
| tgctgagaaa | ggaaagccgt | aacatgaact | ctcgtgttac | tcaactctat | 850 |
| atgcaattat | tacatgagat | tatccgtaag | agggataatt | cacttgaact | 900 |
| ttcccaactg | gaaaacaaaa | tcctcaatgt | caccacagaa | atgttgaaga | 950 |
| tggcaacaag | atacagggaa | ctagaggtga | aatacgcttc | cttgactgat | 1000 |
| cttgtcaata | accaatctgt | gatgatcact | ttgttggaag | aacagtgctt | 1050 |
| gaggatattt | tcccgacaag | acacccatgt | gtctccccca | cttgtccagg | 1100 |
| tggtgccaca | acatattcct | aacagccaac | agtatactcc | tggtctgctg | 1150 |
| ggaggtaacg | agattcagag | ggatccaggt | tatcccagag | atttaatgcc | 1200 |
| accacctgat | ctggcaactt | ctcccaccaa | aagcccttc | aagataccac | 1250 |
| cggtaacttt | catcaatgaa | ggaccattca | agactgtca | gcaagcaaaa | 1300 |
| gaagctgggc | attcggtcag | tgggattat | atgattaaac | ctgaaaacag | 1350 |
| caatggacca | atgcagttat | ggtgtgaaaa | cagtttggac | cctgggggtt | 1400 |
| ggactgttat | tcagaaaaga | acagacggct | ctgtcaactt | cttcagaaat | 1450 |
| tgggaaaatt | ataagaaagg | gtttggaaac | attgacggag | aatactggct | 1500 |
| tggactggaa | aatatctata | tgcttagcaa | tcaagataat | tacaagttat | 1550 |

-continued

| | |
|---|---|
| tgattgaatt agaagactgg agtgataaaa aagtctatgc agaatacagc | 1600 |
| agctttcgtc tggaacctga aagtgaattc tatagactgc gcctgggaac | 1650 |
| ttaccaggga aatgcagggg attctatgat gtggcataat ggtaaacaat | 1700 |
| tcaccacact ggacagagat aaagatatgt atgcaggaaa ctgcgcccac | 1750 |
| tttcataaag gaggctggtg gtacaatgcc tgtgcacatt ctaacctaaa | 1800 |
| tggagtatgg tacagaggag gccattacag aagcaagcac caagatggaa | 1850 |
| ttttctgggc cgaatacaga ggcgggtcat actccttaag agcagttcag | 1900 |
| atgatgatca agcctattga ctgaagagag acactcgcca atttaaatga | 1950 |
| cacagaactt tgtactttc agctcttaaa aatgtaaatg ttacatgtat | 2000 |
| attacttggc acaatttatt tctacacaga aagtttttaa aatgaatttt | 2050 |
| accgtaacta taaagggaa cctataaatg tagtttcatc tgtcgtcaat | 2100 |
| tactgcagaa aattatgtgt atccacaacc tagttatttt aaaaattatg | 2150 |
| ttgactaaat acaagtttg ttttctaaaa tgtaaatatt tgccacaatg | 2200 |
| taaagcaaat cttagctata ttttaaatca taaataacat gttcaagata | 2250 |
| cttaacaatt tatttaaaat ctaagattgc tctaacgtct agtgaaaaaa | 2300 |
| atatttttta aatttcagcc aaataatgca ttttatttta taaaaataca | 2350 |
| gacagaaaat tagggagaaa cttctagttt tgccaataga aaatgttctt | 2400 |
| ccattgaata aaagttatt caaattgaat tgtgcctttt cacacgtaat | 2450 |
| gattaaatct gaattcttaa taatatatcc tatgctgatt tcccaaaac | 2500 |
| atgacccata gtattaaata catatcattt ttaaaaataa aaaaaaaccc | 2550 |
| aaaaataatg catgcataat ttaaatggtc aatttataaa gacaaatcta | 2600 |
| tgaatgaatt tttcagtgtt atcttcatat gatatgctga acaccaaaat | 2650 |
| ctccagaaat gcattttatg tagttctaaa atcagcaaaa tattggtatt | 2700 |
| acaaaaatgc agaatattta gtgtgctaca gatctgaatt atagttctaa | 2750 |
| tttattatta cttttttct aatttactga tcttactact acaaagaaaa | 2800 |
| aaaaacccaa cccatctgca attcaaatca gaaagtttgg acagctttac | 2850 |
| aagtattagt gcatgctcag aacaggtggg actaaaacaa actcaaggaa | 2900 |
| ctgttggctg ttttcccgat actgagaatt caacagctcc agagcagaag | 2950 |
| ccacaggggc atagcttagt ccaaactgct aatttcattt tacagtgtat | 3000 |
| gtaacgctta gtctcacagt gtctttaact catctttgca atcaacaact | 3050 |
| ttactagtga ctttctggaa caatttcctt tcaggaatac atattcactg | 3100 |
| cttagaggtg accttgcctt aatatatttg tgaagttaaa attttaaaga | 3150 |
| tagctcatga aacttttgct taagcaaaaa gaaaacctcg aattgaaatg | 3200 |
| tgtgaggcaa actatgcatg ggaatagctt aatgtgaaga taatcatttg | 3250 |
| gacaactcaa atccatcaac atgaccaatg ttttcatct gccacatctc | 3300 |
| aaaataaaac ttctggtgaa acaaattaaa caaatatcc aaacctcaaa | 3350 |
| aaaaa | 3355 |

<210> SEQ ID NO 4
<211> LENGTH: 491
<212> TYPE: PRT
<213> ORGANISM: Homo Sapiens -continued

```
<400> SEQUENCE: 4

Met Lys Thr Phe Thr Trp Thr Leu Gly Val Leu Phe Phe Leu Leu
 1               5                  10                  15

Val Asp Thr Gly His Cys Arg Gly Gly Gln Phe Lys Ile Lys Lys
                20                  25                  30

Ile Asn Gln Arg Arg Tyr Pro Arg Ala Thr Asp Gly Lys Glu Glu
                35                  40                  45

Ala Lys Lys Cys Ala Tyr Thr Phe Leu Val Pro Glu Gln Arg Ile
                50                  55                  60

Thr Gly Pro Ile Cys Val Asn Thr Lys Gly Gln Asp Ala Ser Thr
                65                  70                  75

Ile Lys Asp Met Ile Thr Arg Met Asp Leu Glu Asn Leu Lys Asp
                80                  85                  90

Val Leu Ser Arg Gln Lys Arg Glu Ile Asp Val Leu Gln Leu Val
                95                  100                 105

Val Asp Val Asp Gly Asn Ile Val Asn Glu Val Lys Leu Leu Arg
                110                 115                 120

Lys Glu Ser Arg Asn Met Asn Ser Arg Val Thr Gln Leu Tyr Met
                125                 130                 135

Gln Leu Leu His Glu Ile Ile Arg Lys Arg Asp Asn Ser Leu Glu
                140                 145                 150

Leu Ser Gln Leu Glu Asn Lys Ile Leu Asn Val Thr Thr Glu Met
                155                 160                 165

Leu Lys Met Ala Thr Arg Tyr Arg Glu Leu Glu Val Lys Tyr Ala
                170                 175                 180

Ser Leu Thr Asp Leu Val Asn Asn Gln Ser Val Met Ile Thr Leu
                185                 190                 195

Leu Glu Glu Gln Cys Leu Arg Ile Phe Ser Arg Gln Asp Thr His
                200                 205                 210

Val Ser Pro Pro Leu Val Gln Val Val Pro Gln His Ile Pro Asn
                215                 220                 225

Ser Gln Gln Tyr Thr Pro Gly Leu Leu Gly Gly Asn Glu Ile Gln
                230                 235                 240

Arg Asp Pro Gly Tyr Pro Arg Asp Leu Met Pro Pro Asp Leu
                245                 250                 255

Ala Thr Ser Pro Thr Lys Ser Pro Phe Lys Ile Pro Pro Val Thr
                260                 265                 270

Phe Ile Asn Glu Gly Pro Phe Lys Asp Cys Gln Gln Ala Lys Glu
                275                 280                 285

Ala Gly His Ser Val Ser Gly Ile Tyr Met Ile Lys Pro Glu Asn
                290                 295                 300

Ser Asn Gly Pro Met Gln Leu Trp Cys Glu Asn Ser Leu Asp Pro
                305                 310                 315

Gly Gly Trp Thr Val Ile Gln Lys Arg Thr Asp Gly Ser Val Asn
                320                 325                 330

Phe Phe Arg Asn Trp Glu Asn Tyr Lys Lys Gly Phe Gly Asn Ile
                335                 340                 345

Asp Gly Glu Tyr Trp Leu Gly Leu Glu Asn Ile Tyr Met Leu Ser
                350                 355                 360

Asn Gln Asp Asn Tyr Lys Leu Leu Ile Glu Leu Glu Asp Trp Ser
                365                 370                 375

Asp Lys Lys Val Tyr Ala Glu Tyr Ser Ser Phe Arg Leu Glu Pro
                380                 385                 390
```

-continued

```
Glu Ser Glu Phe Tyr Arg Leu Arg Leu Gly Thr Tyr Gln Gly Asn
            395                 400                 405
Ala Gly Asp Ser Met Met Trp His Asn Gly Lys Gln Phe Thr Thr
            410                 415                 420
Leu Asp Arg Asp Lys Asp Met Tyr Ala Gly Asn Cys Ala His Phe
            425                 430                 435
His Lys Gly Gly Trp Trp Tyr Asn Ala Cys His Ser Asn Leu
            440                 445                 450
Asn Gly Val Trp Tyr Arg Gly Gly His Tyr Arg Ser Lys His Gln
            455                 460                 465
Asp Gly Ile Phe Trp Ala Glu Tyr Arg Gly Gly Ser Tyr Ser Leu
            470                 475                 480
Arg Ala Val Gln Met Met Ile Lys Pro Ile Asp
            485                 490
```

<210> SEQ ID NO 5
<211> LENGTH: 1780
<212> TYPE: DNA
<213> ORGANISM: Homo Sapiens

<400> SEQUENCE: 5

| | |
|---|---|
| ggctcagagg ccccactgga ccctcggctc ttccttggac ttcttgtgtg | 50 |
| ttctgtgagc ttcgctggat tcagggtctt gggcatcaga ggtgagaggg | 100 |
| tgggaaggtc cgccgcgatg gggaagccct ggctgcgtgc gctacagctg | 150 |
| ctgctcctgc tgggcgcgtc gtgggcgcgg gcgggcgccc cgcgctgcac | 200 |
| ctacaccttc gtgctgcccc cgcagaagtt cacgggcgct gtgtgctgga | 250 |
| gcggccccgc atccacgcgg gcgacgcccg aggccgccaa cgccagcgag | 300 |
| ctggcggcgc tgcgcatgcg cgtcggccgc acgaggagc tgttacgcga | 350 |
| gctgcagagg ctggcggcgg ccgacggcgc cgtggccggc gaggtgcgcg | 400 |
| cgctgcgcaa ggagagccgc ggcctgagcg cgcgcctggg ccagttgcgc | 450 |
| gcgcagctgc agcacgaggc ggggcccggg gcgggcccgg gggcggatct | 500 |
| gggggcggag cctgccgcgg cgctggcgct gctcggggag cgcgtgctca | 550 |
| acgcgtccgc cgaggctcag cgcgcagccg cccggttcca ccagctggac | 600 |
| gtcaagttcc gcgagctggc gcagctcgtc acccagcaga gcagtctcat | 650 |
| cgcccgcctg gagcgcctgt gcccgggagg cgcgggcggg cagcagcagg | 700 |
| tcctgccgcc acccccactg gtgcctgtgg ttccggtccg tcttgtgggt | 750 |
| agcaccagtg acaccagtag gatgctggac ccagccccag agcccagag | 800 |
| agaccagacc cagagacagc aggagcccat ggcttctccc atgcctgcag | 850 |
| gtcaccctgc ggtccccacc aagcctgtgg gcccgtggca ggattgtgca | 900 |
| gaggcccgcc aggcaggcca tgaacagagt ggagtgtatg aactgcgagt | 950 |
| gggccgtcac gtagtgtcag tatggtgtga gcagcaactg gagggtggag | 1000 |
| gctggactgt gatccagcgg aggcaagatg gttcagtcaa cttcttcact | 1050 |
| acctggcagc actataaggc gggctttggg cggccagacg gagaatactg | 1100 |
| gctgggcctt gaacccgtgt atcagctgac cagccgtggg gaccatgagc | 1150 |
| tgctggttct cctggaggac tgggggggcc gtggagcacg tgcccactat | 1200 |
| gatggcttct ccctggaacc cgagagcgac cactaccgcc tgcggcttgg | 1250 |

-continued

```
ccagtaccat ggtgatgctg gagactctct ttcctggcac aatgacaagc        1300
ccttcagcac cgtggatagg gaccgagact cctattctgg taactgtgcc        1350
ctgtaccagc ggggaggctg gtggtaccat gcctgtgccc actccaacct        1400
caacggtgtg tggcaccacg gcggccacta ccgaagccgc taccaggatg        1450
gtgtctactg ggctgagttt cgtggtgggg catattctct caggaaggcc        1500
gccatgctca ttcggcccct gaagctgtga ctctgtgttc ctctgtcccc        1550
taggccctag aggacattgg tcagcaggag cccaagttgt tctggccaca        1600
ccttctttgt ggctcagtgc caatgtgtcc cacagaactt cccactgtgg        1650
atctgtgacc ctgggcgctg aaaatgggac ccaggaatcc ccccgtcaa         1700 tatcttggcc tcagatggct ccccaaggtc attcatatct cggtttgagc        1750
tcatatctta taataacaca aagtagccac                              1780
```

<210> SEQ ID NO 6
<211> LENGTH: 470
<212> TYPE: PRT
<213> ORGANISM: Homo Sapiens

<400> SEQUENCE: 6

```
Met Gly Lys Pro Trp Leu Arg Ala Leu Gln Leu Leu Leu Leu Leu
 1               5                  10                  15

Gly Ala Ser Trp Ala Arg Ala Gly Ala Pro Arg Cys Thr Tyr Thr
                20                  25                  30

Phe Val Leu Pro Pro Gln Lys Phe Thr Gly Ala Val Cys Trp Ser
                35                  40                  45

Gly Pro Ala Ser Thr Arg Ala Thr Pro Glu Ala Ala Asn Ala Ser
                50                  55                  60

Glu Leu Ala Ala Leu Arg Met Arg Val Gly Arg His Glu Glu Leu
                65                  70                  75

Leu Arg Glu Leu Gln Arg Leu Ala Ala Ala Asp Gly Ala Val Ala
                80                  85                  90

Gly Glu Val Arg Ala Leu Arg Lys Glu Ser Arg Gly Leu Ser Ala
                95                 100                 105

Arg Leu Gly Gln Leu Arg Ala Gln Leu Gln His Glu Ala Gly Pro
               110                 115                 120

Gly Ala Gly Pro Gly Ala Asp Leu Gly Ala Glu Pro Ala Ala Ala
               125                 130                 135

Leu Ala Leu Leu Gly Glu Arg Val Leu Asn Ala Ser Ala Glu Ala
               140                 145                 150

Gln Arg Ala Ala Ala Arg Phe His Gln Leu Asp Val Lys Phe Arg
               155                 160                 165

Glu Leu Ala Gln Leu Val Thr Gln Gln Ser Ser Leu Ile Ala Arg
               170                 175                 180

Leu Glu Arg Leu Cys Pro Gly Gly Ala Gly Gly Gln Gln Gln Val
               185                 190                 195

Leu Pro Pro Pro Leu Val Pro Val Pro Val Arg Leu Val
               200                 205                 210

Gly Ser Thr Ser Asp Thr Ser Arg Met Leu Asp Pro Ala Pro Glu
               215                 220                 225

Pro Gln Arg Asp Gln Thr Gln Arg Gln Gln Glu Pro Met Ala Ser
               230                 235                 240
```

```
Pro Met Pro Ala Gly His Pro Ala Val Pro Thr Lys Pro Val Gly
            245                 250                 255

Pro Trp Gln Asp Cys Ala Glu Ala Arg Gln Ala Gly His Glu Gln
        260                 265                 270

Ser Gly Val Tyr Glu Leu Arg Val Gly Arg His Val Ser Val
        275                 280                 285

Trp Cys Glu Gln Gln Leu Glu Gly Gly Gly Trp Thr Val Ile Gln
            290                 295                 300

Arg Arg Gln Asp Gly Ser Val Asn Phe Phe Thr Thr Trp Gln His
            305                 310                 315

Tyr Lys Ala Gly Phe Gly Arg Pro Asp Gly Glu Tyr Trp Leu Gly
            320                 325                 330

Leu Glu Pro Val Tyr Gln Leu Thr Ser Arg Gly Asp His Glu Leu
            335                 340                 345

Leu Val Leu Leu Glu Asp Trp Gly Gly Arg Gly Ala Arg Ala His
            350                 355                 360

Tyr Asp Gly Phe Ser Leu Glu Pro Glu Ser Asp His Tyr Arg Leu
            365                 370                 375

Arg Leu Gly Gln Tyr His Gly Asp Ala Gly Asp Ser Leu Ser Trp
            380                 385                 390

His Asn Asp Lys Pro Phe Ser Thr Val Asp Arg Asp Arg Asp Ser
            395                 400                 405

Tyr Ser Gly Asn Cys Ala Leu Tyr Gln Arg Gly Gly Trp Trp Tyr
            410                 415                 420

His Ala Cys Ala His Ser Asn Leu Asn Gly Val Trp His His Gly
            425                 430                 435

Gly His Tyr Arg Ser Arg Tyr Gln Asp Gly Val Tyr Trp Ala Glu
            440                 445                 450

Phe Arg Gly Gly Ala Tyr Ser Leu Arg Lys Ala Ala Met Leu Ile
            455                 460                 465

Arg Pro Leu Lys Leu
            470

<210> SEQ ID NO 7
<211> LENGTH: 33
<212> TYPE: DNA
<213> ORGANISM: Artificial Sequence
<220> FEATURE:
<223> OTHER INFORMATION:

<400> SEQUENCE: 7
gctgacgaac caaggcaact acaaactcct ggt                              33

<210> SEQ ID NO 8
<211> LENGTH: 41
<212> TYPE: DNA
<213> ORGANISM: Artificial Sequence
<220> FEATURE:
<223> OTHER INFORMATION:

<400> SEQUENCE: 8
tgcggccgga ccagtcctcc atggtcacca ggagtttgta g                     41

<210> SEQ ID NO 9
<211> LENGTH: 33
<212> TYPE: DNA
<213> ORGANISM: Artificial Sequence
<220> FEATURE:
<223> OTHER INFORMATION:
```

```
<400> SEQUENCE: 9
ggtggtgaac tgcttgccgt tgtgccatgt aaa                    33

<210> SEQ ID NO 10
<211> LENGTH: 29
<212> TYPE: DNA
<213> ORGANISM: Artificial Sequence
<220> FEATURE:
<223> OTHER INFORMATION:

<400> SEQUENCE: 10
caggttatcc cagagattta atgccacca                         29

<210> SEQ ID NO 11
<211> LENGTH: 34
<212> TYPE: DNA
<213> ORGANISM: Artificial Sequence
<220> FEATURE:
<223> OTHER INFORMATION:

<400> SEQUENCE: 11
ttggtgggag aagttgccag atcaggtggt ggca                   34

<210> SEQ ID NO 12
<211> LENGTH: 25
<212> TYPE: DNA
<213> ORGANISM: Artificial Sequence
<220> FEATURE:
<223> OTHER INFORMATION:

<400> SEQUENCE: 12
ttcacaccat aactgcattg gtcca                             25

<210> SEQ ID NO 13
<211> LENGTH: 34
<212> TYPE: DNA
<213> ORGANISM: Artificial Sequence
<220> FEATURE:
<223> OTHER INFORMATION:

<400> SEQUENCE: 13
acgtagttcc agtatggtgt gagcagcaac tgga                   34

<210> SEQ ID NO 14
<211> LENGTH: 26
<212> TYPE: DNA
<213> ORGANISM: Artificial Sequence
<220> FEATURE:
<223> OTHER INFORMATION:

<400> SEQUENCE: 14
agtccagcct ccaccctcca gttgct                            26

<210> SEQ ID NO 15
<211> LENGTH: 25
<212> TYPE: DNA
<213> ORGANISM: Artificial Sequence
<220> FEATURE:
<223> OTHER INFORMATION:

<400> SEQUENCE: 15
ccccagtcct ccaggagaac cagca                             25

<210> SEQ ID NO 16
<211> LENGTH: 2042
```

<212> TYPE: DNA
<213> ORGANISM: Homo Sapiens

<400> SEQUENCE: 16

| | | | |
|---|---|---|---|
| gcggacgcgt gggtgaaatt gaaaatcaag ataaaaatgt tcacaattaa | 50 |
| gctccttctt tttattgttc ctctagttat ttcctccaga attgatcaag | 100 |
| acaattcatc atttgattct ctatctccag agccaaaatc aagatttgct | 150 |
| atgttagacg atgtaaaaat tttagccaat ggcctccttc agttgggaca | 200 |
| tggtcttaaa gactttgtcc ataagacgaa gggccaaatt aatgacatat | 250 |
| ttcaaaaact caacatattt gatcagtctt tttatgatct atcgctgcaa | 300 |
| accagtgaaa tcaagaaga agaaaaggaa ctgagaagaa ctacatataa | 350 |
| actacaagtc aaaaatgaag aggtaaagaa tatgtcactt gaactcaact | 400 |
| caaaacttga aagcctccta gaagaaaaaa ttctacttca acaaaaagtg | 450 |
| aaatatttag aagagcaact aactaactta attcaaaatc aacctgaaac | 500 |
| tccagaacac ccagagtaa cttcacttaa aacttttgta gaaaaacaag | 550 |
| ataatagcat caaagacctt ctccagaccg tggaagacca atataaacaa | 600 |
| ttaaaccaac agcatagtca aataaaagaa atagaaaatc agctcagaag | 650 |
| gactagtatt caagaaccca cagaaatttc tctatcttcc aagccaagag | 700 |
| caccaagaac tactcccttt cttcagttga atgaaataag aaatgtaaaa | 750 |
| catgatggca ttcctgctga atgtaccacc atttataaca gaggtgaaca | 800 |
| tacaagtggc atgtatgcca tcagacccag caactctcaa gtttttcatg | 850 |
| tctactgtga tgttatatca ggtagtccat ggacattaat tcaacatcga | 900 |
| atagatggat cacaaaactt caatgaaacg tgggagaact acaaatatgg | 950 |
| ttttgggagg cttgatggag aattttggtt gggcctagag aagatatact | 1000 |
| ccatagtgaa gcaatctaat tatgttttac gaattgagtt ggaagactgg | 1050 |
| aaagacaaca acattatat tgaatattct ttttacttgg gaaatcacga | 1100 |
| aaccaactat acgctacatc tagttgcgat tactggcaat gtccccaatg | 1150 |
| caatcccgga aaacaaagat ttggtgtttt ctacttggga tcacaaagca | 1200 |
| aaaggacact tcaactgtcc agagggttat tcaggaggct ggtggtggca | 1250 |
| tgatgagtgt ggagaaaaca acctaaatgg taaatataac aaaccaagag | 1300 |
| caaaatctaa gccagagagg agaagaggat tatcttggaa gtctcaaaat | 1350 |
| ggaaggttat actctataaa atcaaccaaa atgttgatcc atccaacaga | 1400 |
| ttcagaaagc tttgaatgaa ctgaggcaat ttaaaggcat atttaaccat | 1450 |
| taactcattc caagttaatg tggtctaata atctggtata aatccttaag | 1500 |
| agaaagcttg agaaatagat ttttttatc ttaaagtcac tgtctattta | 1550 |
| agattaaaca tacaatcaca taaccttaaa gaataccgtt tacatttctc | 1600 |
| aatcaaaatt cttataatac tatttgtttt aaattttgtg atgtgggaat | 1650 |
| caatttaga tggtcacaat ctagattata atcaataggt gaacttatta | 1700 |
| ataacttttt ctaaataaaa aatttagaga cttttatttt aaaaggcatc | 1750 |
| atatgagcta atatcacaac tttcccagtt taaaaaacta gtactcttgt | 1800 |
| taaaactcta aacttgacta aatacagagg actggtaatt gtacagttct | 1850 |

-continued

```
taaatgttgt agtattaatt tcaaaactaa aaatcgtcag cacagagtat       1900
gtgtaaaaat ctgtaataca aattttaaa ctgatgcttc attttgctac        1950
aaaataattt ggagtaaatg tttgatatga tttatttatg aaacctaatg       2000
aagcagaatt aaatactgta ttaaaataag ttcgctgtct tt               2042
```

<210> SEQ ID NO 17
<211> LENGTH: 460
<212> TYPE: PRT
<213> ORGANISM: Homo Sapiens

<400> SEQUENCE: 17

```
Met Phe Thr Ile Lys Leu Leu Leu Phe Ile Val Pro Leu Val Ile
 1               5                  10                  15

Ser Ser Arg Ile Asp Gln Asp Asn Ser Ser Phe Asp Ser Leu Ser
                20                  25                  30

Pro Glu Pro Lys Ser Arg Phe Ala Met Leu Asp Asp Val Lys Ile
                35                  40                  45

Leu Ala Asn Gly Leu Leu Gln Leu Gly His Gly Leu Lys Asp Phe
                50                  55                  60

Val His Lys Thr Lys Gly Gln Ile Asn Asp Ile Phe Gln Lys Leu
                65                  70                  75

Asn Ile Phe Asp Gln Ser Phe Tyr Asp Leu Ser Leu Gln Thr Ser
                80                  85                  90

Glu Ile Lys Glu Glu Lys Glu Leu Arg Arg Thr Thr Tyr Lys
                95                  100                 105

Leu Gln Val Lys Asn Glu Glu Val Lys Asn Met Ser Leu Glu Leu
                110                 115                 120

Asn Ser Lys Leu Glu Ser Leu Leu Glu Glu Lys Ile Leu Leu Gln
                125                 130                 135

Gln Lys Val Lys Tyr Leu Glu Glu Gln Leu Thr Asn Leu Ile Gln
                140                 145                 150

Asn Gln Pro Glu Thr Pro Glu His Pro Glu Val Thr Ser Leu Lys
                155                 160                 165

Thr Phe Val Glu Lys Gln Asp Asn Ser Ile Lys Asp Leu Leu Gln
                170                 175                 180

Thr Val Glu Asp Gln Tyr Lys Gln Leu Asn Gln His Ser Gln
                185                 190                 195

Ile Lys Glu Ile Glu Asn Gln Leu Arg Arg Thr Ser Ile Gln Glu
                200                 205                 210

Pro Thr Glu Ile Ser Leu Ser Ser Lys Pro Arg Ala Pro Arg Thr
                215                 220                 225

Thr Pro Phe Leu Gln Leu Asn Glu Ile Arg Asn Val Lys His Asp
                230                 235                 240

Gly Ile Pro Ala Glu Cys Thr Thr Ile Tyr Asn Arg Gly Glu His
                245                 250                 255

Thr Ser Gly Met Tyr Ala Ile Arg Pro Ser Asn Ser Gln Val Phe
                260                 265                 270

His Val Tyr Cys Asp Val Ile Ser Gly Ser Pro Trp Thr Leu Ile
                275                 280                 285

Gln His Arg Ile Asp Gly Ser Gln Asn Phe Asn Glu Thr Trp Glu
                290                 295                 300

Asn Tyr Lys Tyr Gly Phe Gly Arg Leu Asp Gly Glu Phe Trp Leu
                305                 310                 315
```

```
Gly Leu Glu Lys Ile Tyr Ser Ile Val Lys Gln Ser Asn Tyr Val
            320                 325                 330
Leu Arg Ile Glu Leu Glu Asp Trp Lys Asp Asn Lys His Tyr Ile
            335                 340                 345
Glu Tyr Ser Phe Tyr Leu Gly Asn His Glu Thr Asn Tyr Thr Leu
            350                 355                 360
His Leu Val Ala Ile Thr Gly Asn Val Pro Asn Ala Ile Pro Glu
            365                 370                 375
Asn Lys Asp Leu Val Phe Ser Thr Trp Asp His Lys Ala Lys Gly
            380                 385                 390
His Phe Asn Cys Pro Glu Gly Tyr Ser Gly Gly Trp Trp Trp His
            395                 400                 405
Asp Glu Cys Gly Glu Asn Asn Leu Asn Gly Lys Tyr Asn Lys Pro
            410                 415                 420
Arg Ala Lys Ser Lys Pro Glu Arg Arg Arg Gly Leu Ser Trp Lys
            425                 430                 435
Ser Gln Asn Gly Arg Leu Tyr Ser Ile Lys Ser Thr Lys Met Leu
            440                 445                 450
Ile His Pro Thr Asp Ser Glu Ser Phe Glu
            455                 460

<210> SEQ ID NO 18
<211> LENGTH: 2212
<212> TYPE: DNA
<213> ORGANISM: Homo Sapiens

<400> SEQUENCE: 18
gaaagctata ggctacccat tcagctcccc tgtcagagac tcaagctttg              50
agaaaggcta gcaaagagca aggaaagaga gaaaacaaca agtggcgag              100 gccctcagag tgaaagcgta aggttcagtc agcctgctgc agctttgcag             150
acctcagctg ggcatctcca gactcccctg aaggaagagc cttcctcacc             200
caaacccaca aaagatgctg aaaaagcctc tctcagctgt gacctggctc             250
tgcattttca tcgtggcctt tgtcagccac ccagcgtggc tgcagaagct             300
ctctaagcac aagacaccag cacagccaca gctcaaagcg ccaactgct              350 gtgaggaggt gaaggagctc aaggcccaag ttgccaacct tagcagcctg             400
ctgagtgaac tgaacaagaa gcaggagagg gactgggtca gcgtggtcat             450
gcaggtgatg gagctggaga gcaacagcaa gcgcatggag tcgcggctca             500
cagatgctga gagcaagtac tccgagatga caaccaaat tgacatcatg              550 cagctgcagg cagcacagac ggtcactcag acctccgcag atgccatcta             600
cgactgctct tccctctacc agaagaacta ccgcatctct ggagtgtata             650
agcttcctcc tgatgacttc ctgggcagcc ctgaactgga ggtgttctgt             700
gacatggaga cttcaggcgg aggctggacc atcatccaga acgaaaaag              750 tggccttgtc tccttctacc gggactggaa gcagtacaag cagggctttg             800
gcagcatccg tggggacttc tggctgggga cgaacacat ccaccggctc               850 tccagacagc caacccggct gcgtgtagag atggaggact gggagggcaa             900
cctgcgctac gctgagtata gccactttgt tttgggcaat gaactcaaca             950
gctatcgcct cttcctgggg aactacactg gcaatgtggg gaacgacgcc             1000
ctccagtatc ataacaacac agccttcagc accaaggaca ggacaatga              1050
```

-continued

```
caactgcttg  gacaagtgtg  cacagctccg  caaaggtggc  tactggtaca              1100
actgctgcac  agactccaac  ctcaatggag  tgtactaccg  cctgggtgag              1150
cacaataagc  acctggatgg  catcacctgg  tatggctggc  atggatctac              1200
ctactccctc  aaacgggtgg  agatgaaaat  ccgcccagaa  gacttcaagc              1250
cttaaaagga  ggctgccgtg  gagcacggat  acagaaactg  agacacgtgg              1300
agactggatg  agggcagatg  aggacaggaa  gagagtgtta  gaaagggtag              1350
gactgagaaa  cagcctataa  tctccaaaga  aagaataagt  ctccaaggag              1400
cacaaaaaaa  tcatatgtac  caaggatgtt  acagtaaaca  ggatgaacta              1450
tttaaaccca  ctgggtcctg  ccacatcctt  ctcaaggtgg  tagactgagt              1500
ggggtctctc  tgcccaagat  ccctgacata  gcagtagctt  gtcttttcca              1550
catgatttgt  ctgtgaaaga  aaataatttt  gagatcgttt  tatctattttt              1600 ctctacggct  taggctatgt  gagggcaaaa  cacaaatccc  tttgctaaaa              1650
agaaccatat  tattttgatt  ctcaaaggat  aggcctttga  gtgttagaga              1700
aaggagtgaa  ggaggcaggt  gggaaatggt  atttctattt  ttaaatccag              1750
tgaaattatc  ttgagtctac  acattatttt  taaaacacaa  aaattgttcg              1800
gctggaactg  acccaggctg  gacttgcggg  gaggaaactc  cagggcactg              1850
catctggcga  tcagactctg  agcactgccc  ctgctcgcct  tggtcatgta              1900
cagcactgaa  aggaatgaag  caccagcagg  aggtggacag  agtctctcat              1950
ggatgccggc  acaaaactgc  cttaaaatat  tcatagttaa  tacaggtata              2000 tctatttttta  tttactttgt  aagaaacaag  ctcaaggagc  ttccttttaa              2050
attttgtctg  taggaaatgg  ttgaaaactg  aaggtagatg  gtgttatagt              2100
taataataaa  tgctgtaaat  aagcatctca  ctttgtaaaa  ataaaatatt              2150
gtggttttgt  tttaaacatt  caacgtttct  tttccttcta  caataaacac              2200
tttcaaaatg  tt                                                          2212
```

<210> SEQ ID NO 19
<211> LENGTH: 346
<212> TYPE: PRT
<213> ORGANISM: Homo Sapiens

<400> SEQUENCE: 19

```
Met Leu Lys Lys Pro Leu Ser Ala Val Thr Trp Leu Cys Ile Phe
  1               5                  10                  15

Ile Val Ala Phe Val Ser His Pro Ala Trp Leu Gln Lys Leu Ser
                 20                  25                  30

Lys His Lys Thr Pro Ala Gln Pro Gln Leu Lys Ala Ala Asn Cys
                 35                  40                  45

Cys Glu Glu Val Lys Glu Leu Lys Ala Gln Val Ala Asn Leu Ser
                 50                  55                  60

Ser Leu Leu Ser Glu Leu Asn Lys Lys Gln Glu Arg Asp Trp Val
                 65                  70                  75

Ser Val Val Met Gln Val Met Glu Leu Glu Ser Asn Ser Lys Arg
                 80                  85                  90

Met Glu Ser Arg Leu Thr Asp Ala Glu Ser Lys Tyr Ser Glu Met
                 95                 100                 105

Asn Asn Gln Ile Asp Ile Met Gln Leu Gln Ala Ala Gln Thr Val
                110                 115                 120
```

-continued

```
Thr Gln Thr Ser Ala Asp Ala Ile Tyr Asp Cys Ser Ser Leu Tyr
            125                 130                 135

Gln Lys Asn Tyr Arg Ile Ser Gly Val Tyr Lys Leu Pro Pro Asp
            140                 145                 150

Asp Phe Leu Gly Ser Pro Glu Leu Glu Val Phe Cys Asp Met Glu
            155                 160                 165

Thr Ser Gly Gly Gly Trp Thr Ile Ile Gln Arg Arg Lys Ser Gly
            170                 175                 180

Leu Val Ser Phe Tyr Arg Asp Trp Lys Gln Tyr Lys Gln Gly Phe
            185                 190                 195

Gly Ser Ile Arg Gly Asp Phe Trp Leu Gly Asn Glu His Ile His
            200                 205                 210

Arg Leu Ser Arg Gln Pro Thr Arg Leu Arg Val Glu Met Glu Asp
            215                 220                 225

Trp Glu Gly Asn Leu Arg Tyr Ala Glu Tyr Ser His Phe Val Leu
            230                 235                 240

Gly Asn Glu Leu Asn Ser Tyr Arg Leu Phe Leu Gly Asn Tyr Thr
            245                 250                 255

Gly Asn Val Gly Asn Asp Ala Leu Gln Tyr His Asn Asn Thr Ala
            260                 265                 270

Phe Ser Thr Lys Asp Lys Asp Asn Asp Asn Cys Leu Asp Lys Cys
            275                 280                 285

Ala Gln Leu Arg Lys Gly Gly Tyr Trp Tyr Asn Cys Cys Thr Asp
            290                 295                 300

Ser Asn Leu Asn Gly Val Tyr Tyr Arg Leu Gly Glu His Asn Lys
            305                 310                 315

His Leu Asp Gly Ile Thr Trp Tyr Gly Trp His Gly Ser Thr Tyr
            320                 325                 330

Ser Leu Lys Arg Val Glu Met Lys Ile Arg Pro Glu Asp Phe Lys
            335                 340                 345

Pro

<210> SEQ ID NO 20
<211> LENGTH: 286
<212> TYPE: PRT
<213> ORGANISM: Homo Sapiens

<400> SEQUENCE: 20

Glu Glu Lys Asp Gln Leu Gln Val Leu Val Ser Lys Gln Asn Ser
 1               5                  10                  15

Ile Ile Glu Glu Leu Glu Lys Lys Ile Val Thr Ala Thr Val Asn
            20                  25                  30

Asn Ser Val Leu Gln Lys Gln Gln His Asp Leu Met Glu Thr Val
            35                  40                  45

Asn Asn Leu Leu Thr Met Met Ser Thr Ser Asn Ser Ala Lys Asp
            50                  55                  60

Pro Thr Val Ala Lys Glu Glu Gln Ile Ser Phe Arg Asp Cys Ala
            65                  70                  75

Glu Val Phe Lys Ser Gly His Thr Thr Asn Gly Ile Tyr Thr Leu
            80                  85                  90

Thr Phe Pro Asn Ser Thr Glu Glu Ile Lys Ala Tyr Cys Asp Met
            95                 100                 105

Glu Ala Gly Gly Gly Gly Trp Thr Ile Ile Gln Arg Arg Glu Asp
           110                 115                 120
```

```
Gly Ser Val Asp Phe Gln Arg Thr Trp Lys Glu Tyr Lys Val Gly
            125                 130                 135

Phe Gly Asn Pro Ser Gly Glu Tyr Trp Leu Gly Asn Glu Phe Val
            140                 145                 150

Ser Gln Leu Thr Asn Gln Gln Arg Tyr Val Leu Lys Ile His Leu
            155                 160                 165

Lys Asp Trp Glu Gly Asn Glu Ala Tyr Ser Leu Tyr Glu His Phe
            170                 175                 180

Tyr Leu Ser Ser Glu Glu Leu Asn Tyr Arg Ile His Leu Lys Gly
            185                 190                 195

Leu Thr Gly Thr Ala Gly Lys Ile Ser Ser Ile Ser Gln Pro Gly
            200                 205                 210

Asn Asp Phe Ser Thr Lys Asp Gly Asp Asn Asp Lys Cys Ile Cys
            215                 220                 225

Lys Cys Ser Gln Met Leu Thr Gly Gly Trp Trp Phe Asp Ala Cys
            230                 235                 240

Gly Pro Ser Asn Leu Asn Gly Met Tyr Tyr Pro Gln Arg Gln Asn
            245                 250                 255

Thr Asn Lys Phe Asn Gly Ile Lys Trp Tyr Tyr Trp Lys Gly Ser
            260                 265                 270

Gly Tyr Ser Leu Lys Ala Thr Thr Met Met Ile Arg Pro Ala Asp
            275                 280                 285

Phe

<210> SEQ ID NO 21
<211> LENGTH: 214
<212> TYPE: PRT
<213> ORGANISM: Homo Sapiens

<400> SEQUENCE: 21

Asp Cys Ala Asp Val Tyr Gln Ala Gly Phe Asn Lys Ser Gly Ile
 1               5                  10                  15

Tyr Thr Ile Tyr Ile Asn Asn Met Pro Glu Pro Lys Lys Val Phe
             20                  25                  30

Cys Asn Met Asp Val Asn Gly Gly Gly Trp Thr Val Ile Gln His
             35                  40                  45

Arg Glu Asp Gly Ser Leu Asp Phe Gln Arg Gly Trp Lys Glu Tyr
             50                  55                  60

Lys Met Gly Phe Gly Asn Pro Ser Gly Glu Tyr Trp Leu Gly Asn
             65                  70                  75

Glu Phe Ile Phe Ala Ile Thr Ser Gln Arg Gln Tyr Met Leu Arg
             80                  85                  90

Ile Glu Leu Met Asp Trp Glu Gly Asn Arg Ala Tyr Ser Gln Tyr
             95                 100                 105

Asp Arg Phe His Ile Gly Asn Glu Lys Gln Asn Tyr Arg Leu Tyr
            110                 115                 120

Leu Lys Gly His Thr Gly Thr Ala Gly Lys Gln Ser Ser Leu Ile
            125                 130                 135

Leu His Gly Ala Asp Phe Ser Thr Lys Asp Ala Asp Asn Asp Asn
            140                 145                 150

Cys Met Cys Lys Cys Ala Leu Met Leu Thr Gly Gly Trp Trp Phe
            155                 160                 165

Asp Ala Cys Gly Pro Ser Asn Leu Asn Gly Met Phe Tyr Thr Ala
            170                 175                 180
```

```
Gly Gln Asn His Gly Lys Leu Asn Gly Ile Lys Trp His Tyr Phe
            185                 190                 195

Lys Gly Pro Ser Tyr Ser Leu Arg Ser Thr Thr Met Met Ile Arg
            200                 205                 210

Pro Leu Asp Phe

<210> SEQ ID NO 22
<211> LENGTH: 31
<212> TYPE: DNA
<213> ORGANISM: Artificial Sequence
<220> FEATURE:
<223> OTHER INFORMATION:

<400> SEQUENCE: 22
ttcagcacca aggacaagga caatgacaac t                             31

<210> SEQ ID NO 23
<211> LENGTH: 32
<212> TYPE: DNA
<213> ORGANISM: Artificial Sequence
<220> FEATURE:
<223> OTHER INFORMATION:

<400> SEQUENCE: 23
tgtgcacact tgtccaagca gttgtcattg tc                            32

<210> SEQ ID NO 24
<211> LENGTH: 23
<212> TYPE: DNA
<213> ORGANISM: Artificial Sequence
<220> FEATURE:
<223> OTHER INFORMATION:

<400> SEQUENCE: 24
gtagtacact ccattgaggt tgg                                      23

<210> SEQ ID NO 25
<211> LENGTH: 46
<212> TYPE: DNA
<213> ORGANISM: Artificial Sequence
<220> FEATURE:
<223> OTHER INFORMATION:

<400> SEQUENCE: 25
ggattctaat acgactcact atagggccgg gttcacggtg ccatct             46

<210> SEQ ID NO 26
<211> LENGTH: 48
<212> TYPE: DNA
<213> ORGANISM: Artificial Sequence
<220> FEATURE:
<223> OTHER INFORMATION:

<400> SEQUENCE: 26
ctatgaaatt aaccctcact aaagggatgc ggttgtaggt gggtggtt           48

<210> SEQ ID NO 27
<211> LENGTH: 47
<212> TYPE: DNA
<213> ORGANISM: Artificial Sequence
<220> FEATURE:
<223> OTHER INFORMATION:

<400> SEQUENCE: 27
ggattctaat acgactcact atagggccaa caccaagggg caagatg            47
```

<210> SEQ ID NO 28
<211> LENGTH: 48
<212> TYPE: DNA
<213> ORGANISM: Artificial Sequence
<220> FEATURE:
<223> OTHER INFORMATION:

<400> SEQUENCE: 28
ctatgaaatt aaccctcact aaagggaggg cttttggtgg gagaagtt             48

<210> SEQ ID NO 29
<211> LENGTH: 48
<212> TYPE: DNA
<213> ORGANISM: Artificial Sequence
<220> FEATURE:
<223> OTHER INFORMATION:

<400> SEQUENCE: 29
ggattctaat acgactcact atagggcgct ccgcaaaggt ggctactg             48

<210> SEQ ID NO 30
<211> LENGTH: 47
<212> TYPE: DNA
<213> ORGANISM: Artificial Sequence
<220> FEATURE:
<223> OTHER INFORMATION:

<400> SEQUENCE: 30
ctatgaaatt aaccctcact aaagggattt cctccccgca agtccag              47

<210> SEQ ID NO 31
<211> LENGTH: 48
<212> TYPE: DNA
<213> ORGANISM: Artificial Sequence
<220> FEATURE:
<223> OTHER INFORMATION:

<400> SEQUENCE: 31
ggattctaat acgactcact atagggcggc cgccacgagg agctgtta             48

<210> SEQ ID NO 32
<211> LENGTH: 46
<212> TYPE: DNA
<213> ORGANISM: Artificial Sequence
<220> FEATURE:
<223> OTHER INFORMATION:

<400> SEQUENCE: 32
ctatgaaatt aaccctcact aaagggaggg gctctggggc tgggtc               46

<210> SEQ ID NO 33
<211> LENGTH: 20
<212> TYPE: DNA
<213> ORGANISM: Artificial Sequence
<220> FEATURE:
<223> OTHER INFORMATION:

<400> SEQUENCE: 33
gtcagcagga gcccaagttg                                            20

<210> SEQ ID NO 34
<211> LENGTH: 20
<212> TYPE: DNA
<213> ORGANISM: Artificial Sequence
<220> FEATURE:
<223> OTHER INFORMATION:

-continued

```
<400> SEQUENCE: 34
acggttacac agggtgtctt                                                    20

<210> SEQ ID NO 35
<211> LENGTH: 25
<212> TYPE: DNA
<213> ORGANISM: Artificial Sequence
<220> FEATURE:
<223> OTHER INFORMATION:

<400> SEQUENCE: 35
tctggccaca ccttctttgt ggctc                                              25
```